(12) United States Patent
Yamaguchi et al.

(10) Patent No.: US 12,415,812 B2
(45) Date of Patent: Sep. 16, 2025

(54) ORGANIC COMPOUND, LIGHT-EMITTING DEVICE MATERIAL, LIGHT-EMITTING DEVICE, LIGHT-EMITTING APPARATUS, LIGHT-EMITTING MODULE, ELECTRONIC DEVICE, AND LIGHTING DEVICE

(71) Applicant: Semiconductor Energy Laboratory Co., Ltd., Kanagawa-ken (JP)

(72) Inventors: Tomoya Yamaguchi, Kanagawa (JP); Hiromitsu Kido, Kanagawa (JP); Hideko Yoshizumi, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 974 days.

(21) Appl. No.: 17/285,251

(22) PCT Filed: Oct. 7, 2019

(86) PCT No.: PCT/IB2019/058508
§ 371 (c)(1),
(2) Date: Apr. 14, 2021

(87) PCT Pub. No.: WO2020/079524
PCT Pub. Date: Apr. 23, 2020

(65) Prior Publication Data
US 2021/0371427 A1    Dec. 2, 2021

(30) Foreign Application Priority Data
Oct. 19, 2018   (JP) .................................. 2018-197429

(51) Int. Cl.
*C07D 495/00*    (2006.01)
*H10K 50/11*    (2023.01)
(Continued)

(52) U.S. Cl.
CPC ....... *C07D 495/00* (2013.01); *H10K 85/6576* (2023.02); *H10K 50/11* (2023.02); *H10K 50/15* (2023.02); *H10K 2101/10* (2023.02)

(58) Field of Classification Search
None
See application file for complete search history.

(56) References Cited

U.S. PATENT DOCUMENTS

| 2,669,517 A | 2/1954 | Mueller |
| 8,994,263 B2 | 3/2015 | Shitagaki et al. |

(Continued)

FOREIGN PATENT DOCUMENTS

| CN | 104292241 A | 1/2015 |
| CN | 105283977 A | 1/2016 |

(Continued)

OTHER PUBLICATIONS

International Search Report (Application No. PCT/IB2019/058508) Dated Dec. 24, 2019.

(Continued)

*Primary Examiner* — Jeffrey D Washville
(74) *Attorney, Agent, or Firm* — Husch Blackwell LLP

(57) ABSTRACT

An organic compound with high heat resistance is provided. A novel organic compound that can be used for a light-emitting device that emits red light or near-infrared light is provided. An organic compound represented by General Formula (G0) is provided. In General Formula (G0), Q represents oxygen or sulfur, Ar1 represents a substituted or unsubstituted fused aromatic ring, R1 and R2 each independently represent hydrogen or a group with 1 to 100, inclusive, carbon atoms in total, and at least one of R1 and R2 has a hole-transport skeleton or a fused ring.

(Continued)

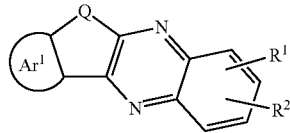

9 Claims, 21 Drawing Sheets

(51) Int. Cl.
*H10K 50/15* (2023.01)
*H10K 85/60* (2023.01)
*H10K 101/10* (2023.01)

(56) References Cited

U.S. PATENT DOCUMENTS

| | | | |
|---|---|---|---|
| 9,538,607 B2 | 1/2017 | Shitagaki et al. | |
| 9,553,274 B2 | 1/2017 | Xia et al. | |
| 9,604,928 B2 | 3/2017 | Shitagaki et al. | |
| 9,806,269 B2 | 10/2017 | Noh et al. | |
| 9,917,257 B2 | 3/2018 | Lee et al. | |
| 10,496,476 B2 | 12/2019 | Chae | |
| 10,680,190 B2 | 6/2020 | Kim et al. | |
| 10,734,589 B2 | 8/2020 | Suzuki et al. | |
| 2015/0021556 A1 | 1/2015 | Xia et al. | |
| 2015/0333271 A1 | 11/2015 | Chung et al. | |
| 2016/0141515 A1* | 5/2016 | Hayama | C07D 491/048 544/215 |
| 2017/0047537 A1 | 2/2017 | Shitagaki et al. | |
| 2017/0141331 A1 | 5/2017 | Kim et al. | |
| 2017/0179411 A1 | 6/2017 | Shitagaki et al. | |
| 2018/0053903 A1 | 2/2018 | Suzuki et al. | |
| 2018/0102486 A1 | 4/2018 | Lee et al. | |
| 2019/0031673 A1 | 1/2019 | Yamaguchi et al. | |
| 2019/0131540 A1 | 5/2019 | Sim et al. | |
| 2020/0152887 A1 | 5/2020 | Yamaguchi et al. | |
| 2020/0358003 A1 | 11/2020 | Suzuki et al. | |
| 2021/0143337 A1 | 5/2021 | Kim et al. | |

FOREIGN PATENT DOCUMENTS

| | | |
|---|---|---|
| CN | 110073510 A | 7/2019 |
| EP | 2 826 781 A1 | 1/2015 |
| EP | 3 010 055 A1 | 4/2016 |
| EP | 3029125 A | 6/2016 |
| GB | 736849 | 9/1955 |
| JP | 2007-137872 A | 6/2007 |
| JP | 2015-021007 A | 2/2015 |
| JP | 2018-110223 A | 7/2018 |
| JP | 2018-127402 A | 8/2018 |
| JP | 2018-188418 A | 11/2018 |
| JP | 2019-069965 A | 5/2019 |
| KR | 2015-0009462 A | 1/2015 |
| KR | 2016-0018458 A | 2/2016 |
| KR | 2016-0068641 A | 6/2016 |
| KR | 2019-0049958 A | 5/2019 |
| KR | 2019-0099508 A | 8/2019 |
| KR | 2020-0015495 A | 2/2020 |
| TW | 201829413 | 8/2018 |
| TW | 201831650 | 9/2018 |
| WO | WO 2014/199637 A1 | 12/2014 |
| WO | WO 2018/033820 A1 | 2/2018 |
| WO | WO 2018/122664 A1 | 7/2018 |

OTHER PUBLICATIONS

Written Opinion (Application No. PCT/IB2019/058508) Dated Dec. 24, 2019.

* cited by examiner

9700

ORGANIC COMPOUND, LIGHT-EMITTING DEVICE MATERIAL, LIGHT-EMITTING DEVICE, LIGHT-EMITTING APPARATUS, LIGHT-EMITTING MODULE, ELECTRONIC DEVICE, AND LIGHTING DEVICE

This application is a 371 of international application PCT/IB2019/058508 filed on Oct. 7, 2019 which is incorporated herein by reference.

TECHNICAL FIELD

One embodiment of the present invention relates to an organic compound, a light-emitting device material (also referred to as a light-emitting element material), a light-emitting device (also referred to as a light-emitting element), a light-emitting apparatus, a light-emitting module, an electronic device, and a lighting device.

Note that one embodiment of the present invention is not limited to the above technical field. Examples of the technical field of one embodiment of the present invention include a semiconductor device, a display device, a light-emitting apparatus, a power storage device, a memory device, an electronic device, a lighting device, an input device (e.g., a touch sensor), an input/output device (e.g., a touch panel), a driving method thereof, and a manufacturing method thereof.

BACKGROUND ART

Research and development has been actively conducted on light-emitting devices using organic electroluminescence (EL) phenomenon (also referred to as organic EL devices or organic EL elements). In a basic structure of an organic EL device, a layer including a light-emitting organic compound (hereinafter also referred to as a light-emitting layer) is sandwiched between a pair of electrodes. By application of voltage to the organic EL device, light emitted from the light-emitting organic compound can be obtained.

Examples of the light-emitting organic compound are a compound capable of converting a singlet excited state into light emission (also referred to as a fluorescent compound or a fluorescent material) and a compound capable of converting a triplet excited state into light emission (also referred to as a phosphorescent compound or a phosphorescent material). An organometallic complex that contains iridium or the like as a central metal is disclosed as a phosphorescent compound in Patent Document 1.

When a phosphorescent compound is used to form a light-emitting layer of a light-emitting device, the phosphorescent compound is usually dispersed in a matrix of another compound to form the light-emitting layer so that concentration quenching or quenching due to triplet-triplet annihilation of the phosphorescent compound can be inhibited. Here, the compound serving as the matrix is called host material, and the compound dispersed in the matrix, such as a phosphorescent compound, is called guest material.

The properties necessary for a host material in the case where a phosphorescent compound is a guest material are to have higher triplet excitation energy (an energy difference between a ground state and a triplet excited state) than that of the phosphorescent compound.

Furthermore, since singlet excitation energy (energy difference between a ground state and a singlet excited state) is higher than triplet excitation energy, a substance that has high triplet excitation energy also has high singlet excitation energy. Thus, the substance that has high triplet excitation energy as described above is also effective in a light-emitting device using a fluorescent compound as a light-emitting substance.

An organic EL device is suitable for a display device because it has features such as ease of thinning and lightening, high-speed response to an input signal, and driving with a direct-current low voltage source.

An organic EL device can be formed in a film form and thus can provide planar light emission. Accordingly, a large-area light-emitting device can be easily formed. This feature is difficult to obtain with a point light source typified by an LED (light-emitting diode) or a linear light source typified by a fluorescent lamp. Thus, an organic EL device also has great potential as a planar light source applicable to a lighting device and the like.

Image sensors have been used in a variety of applications such as personal authentication, defect analysis, medical diagnosis, and security. The wavelength of light sources used for image sensors is different depending on applications. Light having a variety of wavelengths, for example, light having a short wavelength, such as visible light and X-rays, and light having a long wavelength, such as near-infrared light, is used for image sensors.

Light-emitting devices have been considered to be applied to light sources of image sensors such as the above in addition to display devices and lighting devices.

REFERENCE

[Patent Document]
[Patent Document 1] Japanese Published Patent Application No. 2007-137872

SUMMARY OF THE INVENTION

Problems to be Solved by the Invention

An object of one embodiment of the present invention is to provide a novel organic compound. Another object of one embodiment of the present invention is to provide an organic compound with high heat resistance. Another object of one embodiment of the present invention is to provide a novel organic compound that can be used for a light-emitting device. Another object of one embodiment of the present invention is to provide a novel organic compound that can be used for a light-emitting device that emits red light or near-infrared light. Another object of one embodiment of the present invention is to provide a novel organic compound that can be used as a host material, in which a light-emitting substance is dispersed, in a light-emitting device.

Another object of one embodiment of the present invention is to provide a light-emitting device having high emission efficiency. Another object of one embodiment of the present invention is to provide a light-emitting device with a low driving voltage. Another object of one embodiment of the present invention is to provide a light-emitting device with a long lifetime. Another object of one embodiment of the present invention is to provide a light-emitting device with high heat resistance. Another embodiment of the present invention is to provide a novel light-emitting device that emits red light or near-infrared light.

Note that the description of these objects does not preclude the existence of other objects. One embodiment of the present invention does not need to achieve all these objects. Other objects can be derived from the descriptions of the specification, the drawings, and the claims.

Means for Solving the Problems

One embodiment of the present invention is an organic compound represented by General Formula (G0).

[Chemical Formula 1]

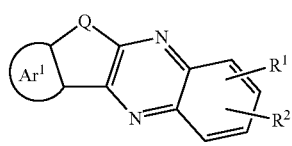

(G0)

In General Formula (G0), Q represents oxygen or sulfur, $Ar^1$ represents a substituted or unsubstituted fused aromatic ring, $R^1$ and $R^2$ each independently represent hydrogen or a group with 1 to 100, inclusive, carbon atoms in total, and at least one of $R^1$ and $R^2$ has a hole-transport skeleton.

Another embodiment of the present invention is an organic compound represented by General Formula (G0).

[Chemical Formula 2]

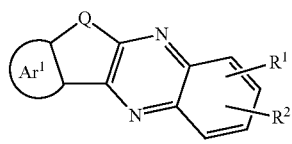

(G0)

In General Formula (G0), Q represents oxygen or sulfur, $Ar^1$ represents any one of a substituted or unsubstituted naphthalene ring, a substituted or unsubstituted phenanthrene ring, and a substituted or unsubstituted chrysene ring, $R^1$ and $R^2$ each independently represent hydrogen or a group with 1 to 100, inclusive, carbon atoms in total, and at least one of $R^1$ and $R^2$ has a hole-transport skeleton.

Preferably, the hole-transport skeleton is any one of a substituted or unsubstituted diarylamino group, a substituted or unsubstituted fused aromatic hydrocarbon ring, and a substituted or unsubstituted π rich fused heteroaromatic ring.

Another embodiment of the present invention is an organic compound represented by General Formula (G0).

[Chemical Formula 3]

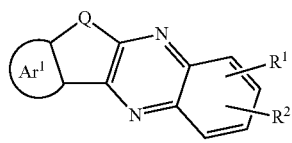

(G0)

In General Formula (G0), Q represents oxygen or sulfur, $Ar^1$ represents a substituted or unsubstituted fused aromatic ring, $R^1$ and $R^2$ each independently represent hydrogen or a group with 1 to 100, inclusive, carbon atoms in total, and at least one of $R^1$ and $R^2$ comprises a fused ring.

Another embodiment of the present invention is an organic compound represented by General Formula (G0).

[Chemical Formula 4]

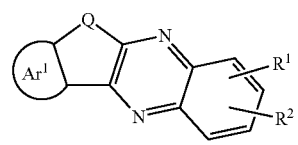

(G0)

In General Formula (G0), Q represents oxygen or sulfur, $Ar^1$ represents any one of a substituted or unsubstituted naphthalene ring, a substituted or unsubstituted phenanthrene ring, and a substituted or unsubstituted chrysene ring, $R^1$ and $R^2$ each independently represent hydrogen or a group with 1 to 100, inclusive, carbon atoms in total, and at least one of $R^1$ and $R^2$ has a fused ring.

The fused ring is preferably any one of a substituted or unsubstituted fused aromatic hydrocarbon ring and a substituted or unsubstituted 7c rich fused heteroaromatic ring.

The fused ring is preferably a substituted or unsubstituted fused heteroaromatic ring including any one of a dibenzothiophene skeleton, a dibenzofuran skeleton, and a carbazole skeleton.

The fused ring is preferably a substituted or unsubstituted fused aromatic hydrocarbon ring including any one of a naphthalene skeleton, a fluorene skeleton, a triphenylene skeleton, and a phenanthrene skeleton.

Another embodiment of the present invention is an organic compound represented by General Formula (G0).

[Chemical Formula 5]

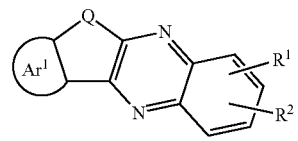

(G0)

$A^1$—$(\alpha)_n$—* (u1)

In General Formula (G0), Q represents oxygen or sulfur, $Ar^1$ represents a substituted or unsubstituted fused aromatic ring, $R^1$ and $R^2$ each independently represent hydrogen or a group with 1 to 100, inclusive, carbon atoms in total, at least one of $R^1$ and $R^2$ has a hole-transport skeleton, and at least one of $R^1$ and $R^2$ represents a structure represented by General Formula (u1). In General Formula (u1), α represents a substituted or unsubstituted arylene group with 6 to 25, inclusive, carbon atoms, n represents an integer greater than or equal to 0 and less than or equal to 4, $A^1$ represents any one of a substituted or unsubstituted aryl group with 6 to 30, inclusive, carbon atoms and a substituted or unsubstituted heteroaryl group with 3 to 30, inclusive, carbon atoms, and * represents a connection portion in General Formula (G0).

Another embodiment of the present invention is an organic compound represented by General Formula (G0).

[Chemical Formula 6]

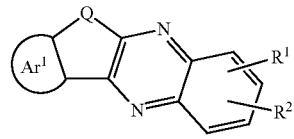
(G0)

$A^1—(α)_n—*$ (u1)

In General Formula (G0), Q represents oxygen or sulfur, $Ar^1$ represents any one of a substituted or unsubstituted naphthalene ring, a substituted or unsubstituted phenanthrene ring, and a substituted or unsubstituted chrysene ring, $R^1$ and $R^2$ each independently represent hydrogen or a group with 1 to 100, inclusive, carbon atoms in total, at least one of $R^1$ and $R^2$ has a hole-transport skeleton, and at least one of $R^1$ and $R^2$ represents a structure represented by General Formula (u1). In General Formula (u1), α represents a substituted or unsubstituted arylene group with 6 to 25, inclusive, carbon atoms, n represents an integer greater than or equal to 0 and less than or equal to 4, $A^1$ represents any one of a substituted or unsubstituted aryl group with 6 to 30, inclusive, carbon atoms and a substituted or unsubstituted heteroaryl group with 3 to 30, inclusive, carbon atoms, and * represents a connection portion in General Formula (G0).

In General Formula (u1), $A^1$ represents any one of General Formula ($A^1$-1) to General Formula ($A^1$-17).

[Chemical Formula 7]

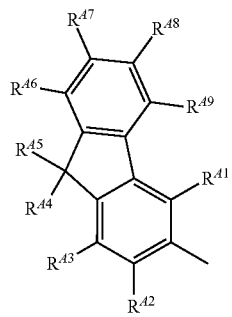
($A^1$-1)

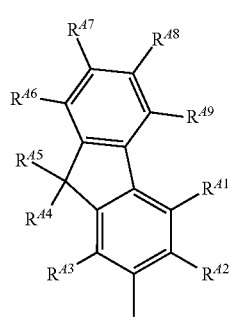
($A^1$-2)

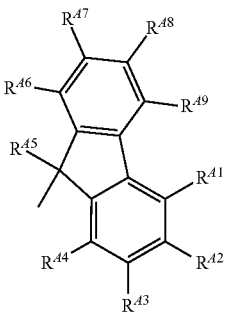
($A^1$-3)

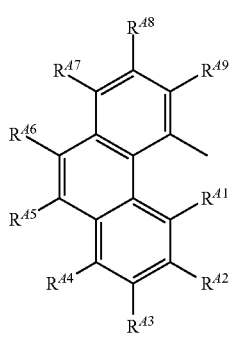
($A^1$-4)

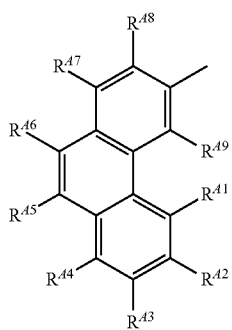
($A^1$-5)

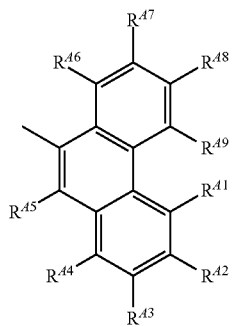
($A^1$-6)

-continued
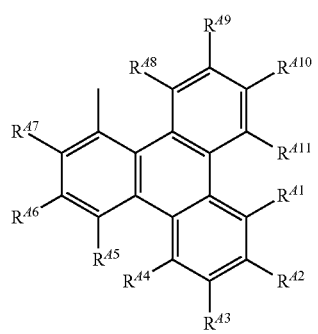 (A¹-7)
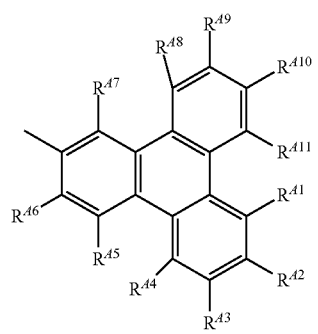 (A¹-8)
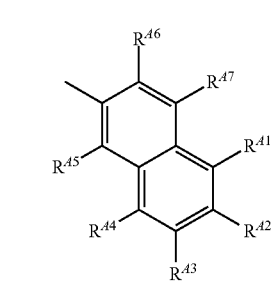 (A¹-9)
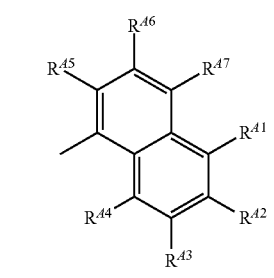 (A¹-10)
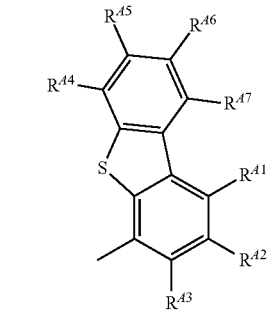 (A¹-11)
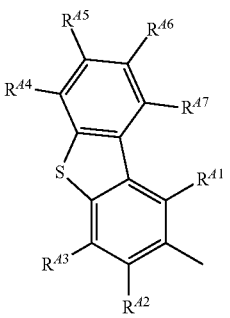 (A¹-12)
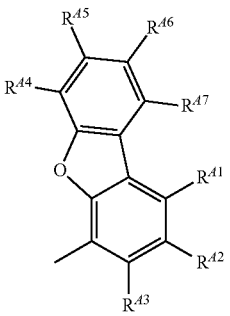 (A¹-13)
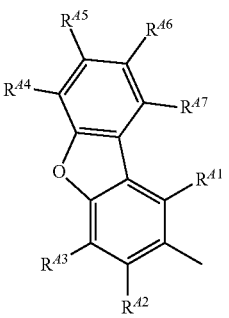 (A¹-14)
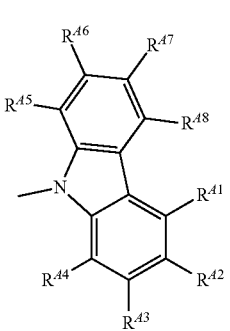 (A¹-15)
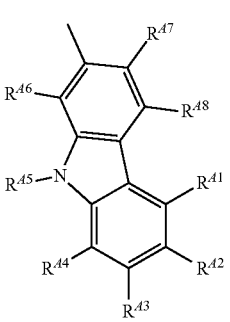 (A¹-16)

(A¹-17)

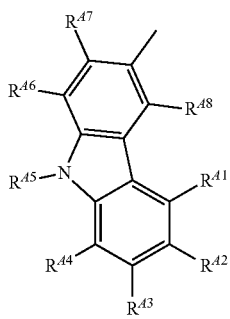

(Ar-5)

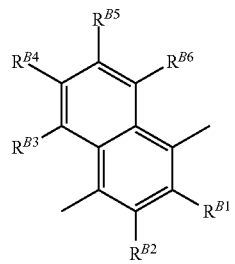

In General Formula (A¹-1) to General Formula (A¹-17), $R^{A1}$ to $R^{A11}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, and a substituted or unsubstituted aryl group with 6 to 30, inclusive, carbon atoms.

In General Formula (u1), α preferably represents any one of General Formula (Ar-1) to General Formula (Ar-14).

[Chemical Formula 8]

(Ar-6)

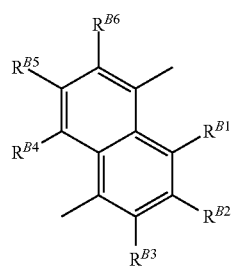

(Ar-1)

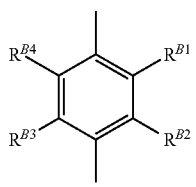

(Ar-7)

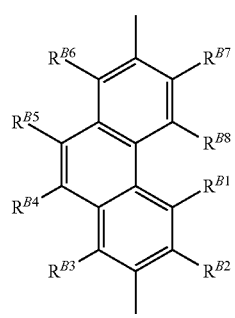

(Ar-2)

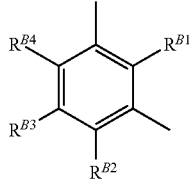

(Ar-3)

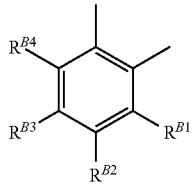

(Ar-8)

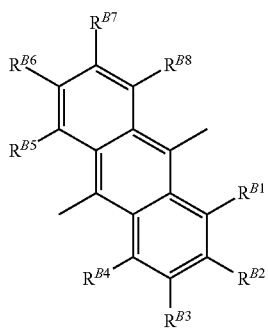

(Ar-4)

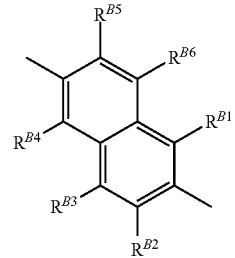

(Ar-9)

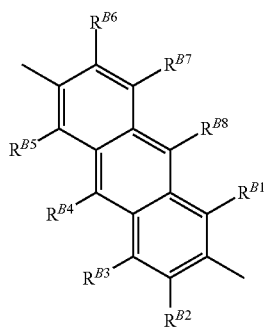

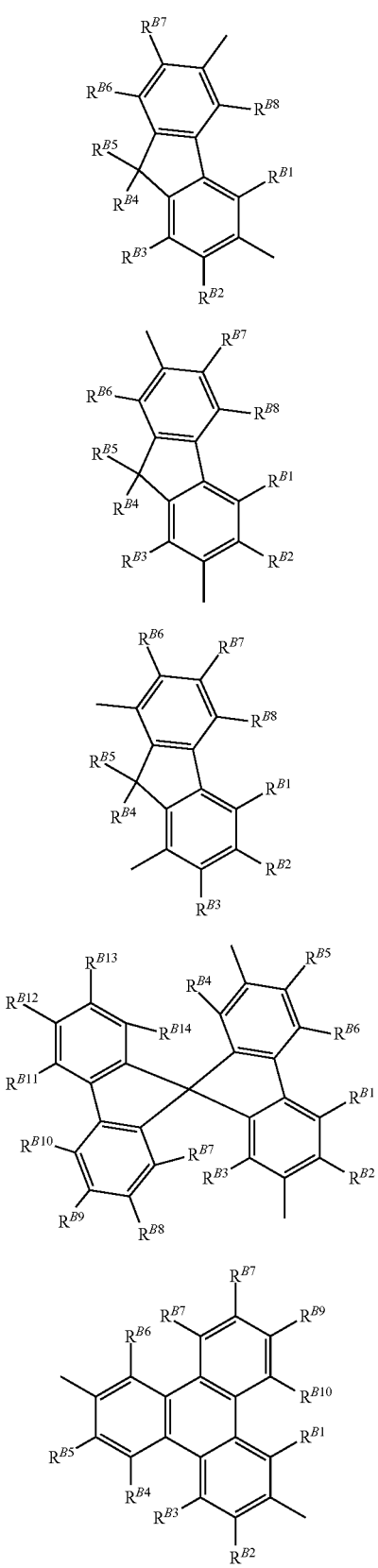

(Ar-10)
(Ar-11)
(Ar-12)
(Ar-13)
(Ar-14)

In General Formula (A$^1$-1) to General Formula (A$^1$-17), R$^{B1}$ to R$^{B14}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, and a substituted or unsubstituted aryl group with 6 to 30, inclusive, carbon atoms.

In each of the organic compounds of one embodiment of the present invention, Ar$^1$ in General Formula (G0) represents any one of General Formula (t1) to General Formula (t3).

[Chemical Formula 9]

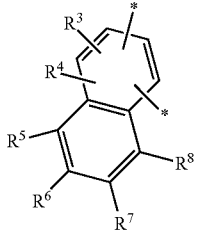

(t1)

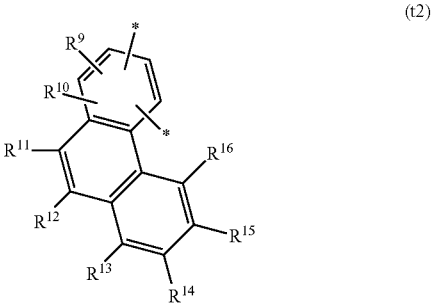

(t2)

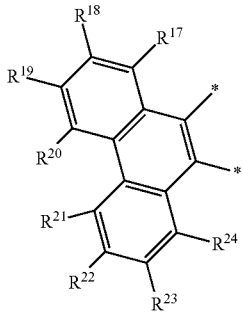

(t3)

In General Formula (t1) to General Formula (t3), R$^3$ to R$^{24}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, a substituted or unsubstituted aryl group with 6 to 30, inclusive, carbon atoms, and * represents a connection portion in General Formula (G0).

An organic compound of one embodiment of the present invention is preferably represented by General Formula (G1).

[Chemical Formula 10]

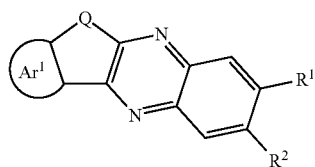

(G1)

In General Formula (G1), Q represents oxygen or sulfur, Ar¹ represents a substituted or unsubstituted fused aromatic ring (or any one of a substituted or unsubstituted naphthalene ring, a substituted or unsubstituted phenanthrene ring, and a substituted or unsubstituted chrysene ring), le and $R^2$ each independently represent hydrogen or a group with 1 to 100, inclusive, carbon atoms in total, and at least one of $R^1$ and $R^2$ has a hole-transport skeleton or a fused ring, The organic compound of one embodiment of the present invention is preferably represented by any one of General Formula (G1-1) to General Formula (G1-4).

[Chemical Formula 11]

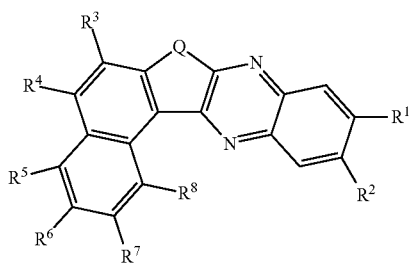

(G1-1)

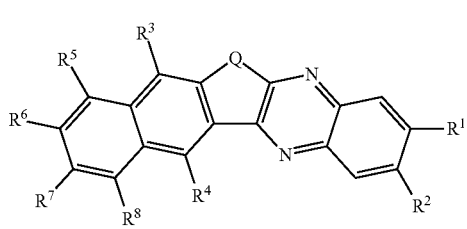

(G1-2)

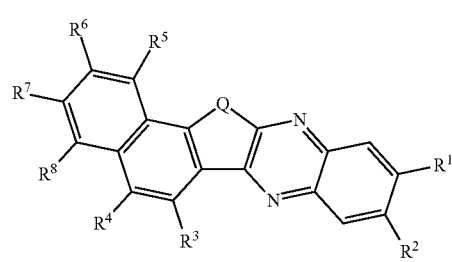

(G1-3)

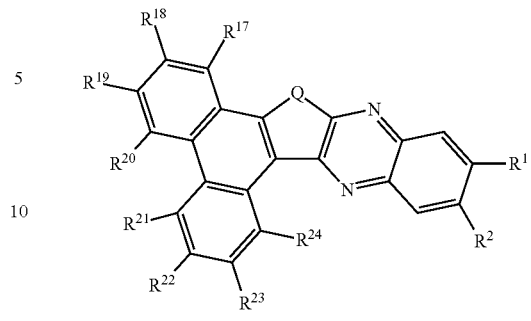

(G1-4)

In General Formula (G1-1) to General Formula (G1-4), Q represents oxygen or sulfur, $R^1$ and $R^2$ each independently represent hydrogen or a group with 1 to 100, inclusive, carbon atoms in total, at least one of $R^1$ and $R^2$ has a hole-transport skeleton or a fused ring, and $R^3$ to $R^8$ and $R^{17}$ to $R^{24}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, and a substituted or unsubstituted aryl group with 6 to 30, inclusive, carbon atoms.

Another embodiment of the present invention is a light-emitting device material including a furoquinoxaline skeleton to which a fused aromatic ring is fused. Another embodiment of the present invention is a light-emitting device material including a structure in which a fused aromatic ring is fused to a furan ring of a furoquinoxaline skeleton. The light-emitting device material of one embodiment of the present invention is preferably a light-emitting device material emitting red or near-infrared light. The light-emitting device material of one embodiment of the present invention is preferably a host material for a light-emitting device. The light-emitting device material of one embodiment of the present invention is preferably an electron-transport material for a light-emitting device.

One embodiment of the present invention is a light-emitting device including the organic compound or the light-emitting device material that has any of the above-described structures.

One embodiment of the present invention is a light-emitting device that includes a layer including an organic compound between a pair of electrodes, and the layer including an organic compound includes the organic compound or light-emitting device material with any of the above structures.

One embodiment of the present invention is a light-emitting device that includes a layer including an organic compound between a pair of electrodes, the layer including an organic compound includes a light-emitting layer, and the light-emitting layer includes the organic compound or light-emitting device material with any of the above structures.

One embodiment of the present invention is a light-emitting device which includes a layer including an organic compound between a pair of electrodes, the layer including an organic compound includes an electron-transport layer, and the at least one of the light-emitting layer and the electron-transport layer includes the organic compound or light-emitting device material with any of the above structures.

One embodiment of the present invention is a light-emitting apparatus that includes the light-emitting device having any of the above-described structures, and one or both of a transistor and a substrate.

One embodiment of the present invention is a light-emitting module including the above-described light-emitting apparatus, where a connector such as a flexible printed circuit (hereinafter referred to as FPC) or a TCP (Tape Carrier Package) is attached or an integrated circuit (IC) is mounted by a COG (Chip On Glass) method, a COF (Chip On Film) method, or the like. Note that the light-emitting module of one embodiment of the present invention may include only one of a connector and an IC or may include both of them.

One embodiment of the present invention is an electronic device including the above-described light-emitting module and at least one of an antenna, a battery, a housing, a camera, a speaker, a microphone, and an operation button.

One embodiment of the present invention is a lighting device including the above-described light-emitting device and at least one of a housing, a cover, and a support.

Effect of the Invention

One embodiment of the present invention can provide a novel organic compound. One embodiment of the present invention can provide an organic compound with high heat resistance. One embodiment of the present invention can provide an organic compound with high sublimability. One embodiment of the present invention can provide a novel organic compound that can be used for a light-emitting device. One embodiment of the present invention can provide an organic compound that can be used for a light-emitting device that emits red light or near-infrared light. One embodiment of the present invention can provide a novel organic compound that can be used as a host material, in which a light-emitting substance is dispersed, in a light-emitting device.

One embodiment of the present invention can provide a light-emitting device with high emission efficiency. One embodiment of the present invention can provide a light-emitting device with low driving voltage. One embodiment of the present invention can provide a light-emitting device with a long lifetime. One embodiment of the present invention can provide a light-emitting device with high heat resistance. One embodiment of the present invention can provide a novel light-emitting device that emits red light or near-infrared light.

Note that the description of these effects does not preclude the existence of other effects. One embodiment of the present invention does not need to have all these effects. Other effects can be derived from the descriptions of the specification, the drawings, and the claims.

MODE FOR CARRYING OUT THE INVENTION

Figure 1A:
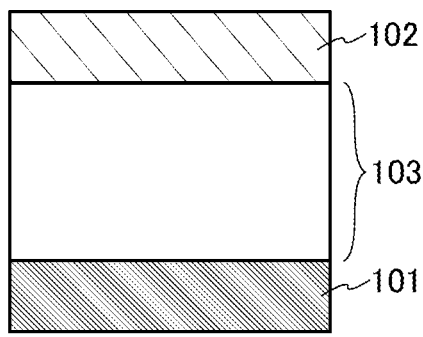
FIG. 1A, FIG. 1B, FIG. 1C, and FIG. 1D are cross-sectional views illustrating examples of light-emitting devices.

Embodiments will be described in detail with reference to the drawings. Note that the present invention is not limited to the following description, and it will be readily appreciated by those skilled in the art that modes and details of the present invention can be modified in various ways without departing from the spirit and scope of the present invention. Thus, the present invention should not be construed as being limited to the description in the following embodiments.

Note that in the structures of the present invention described below, the same portions or portions having similar functions are denoted by the same reference numerals in different drawings, and description thereof is not repeated. Furthermore, the same hatch pattern is used for portions having similar functions, and the portions are not especially denoted by reference numerals in some cases.

The position, size, range, or the like of each component illustrated in drawings does not represent the actual position, size, range, or the like in some cases for easy understanding. Therefore, the disclosed invention is not necessarily limited to the position, size, range, or the like disclosed in the drawings.

Note that the term "film" and the term "layer" can be interchanged with each other depending on the case or circumstances. For example, the term "conductive layer" can be changed into the term "conductive film". As another example, the term "insulating film" can be changed into the term "insulating layer".

Embodiment 1

In this embodiment, an organic compound of one embodiment of the present invention will be described below.

[Structure of Organic Compound of One Embodiment of Present Invention]

One embodiment of the present invention is an organic compound having a structure in which a fused aromatic ring is fused to a furoquinoxaline skeleton or a thienoquinoxaline skeleton. Another embodiment of the present invention is a light-emitting device material having a structure in which a fused aromatic ring is fused to a furoquinoxaline skeleton or a thienoquinoxaline skeleton.

The light-emitting device material is preferably a material particularly for a light-emitting device that emits red or near-infrared light.

The light-emitting device material is preferably a host material or an electron-transport material for a light-emitting device.

A quinoxaline skeleton has a structure in which a benzene ring is fused to a pyrazine ring. Thus, when a furoquinoxaline skeleton or a thienoquinoxaline skeleton is used, a π-conjugated system can extend, the lowest unoccupied molecular orbital (LUMO level) can be made deep, and the organic compound can be energetically stabilized, as compared with when a furopyrazine skeleton or a thienopyrazine skeleton is used. In addition, since the LUMO level is made deep, the triplet excited level ($T_1$ level) can be made low. As compared with when a fused aromatic ring is not included or when a monocyclic aromatic ring is fused, a π-conjugated system can extend, the LUMO level can be made deep, the organic compound can be energetically stabilized, and the $T_1$ level can be made low when a fused aromatic ring is fused to a furoquinoxaline skeleton or a thienoquinoxaline skeleton. For these reasons, the organic compound of one embodiment of the present invention can be favorably used for a light-emitting device in which the emission wavelength is a long (e.g., red to near-infrared) wavelength.

A light-emitting substance whose emission wavelength is a long wavelength tends to have a low $T_1$ level and a deep LUMO level. Thus, the organic compound of one embodiment of the present invention is preferably used in combination with a light-emitting substance whose emission wavelength is a long wavelength. When a light-emitting substance whose emission wavelength is a long wavelength is used as a guest material and the organic compound of one embodiment of the present invention is used as a host material, the light-emitting device can have increased emission efficiency and reduced driving voltage.

An organic compound including a pyrazine ring features a higher glass transition temperature and higher heat resistance than an organic compound including a pyrimidine skeleton. Since the organic compound of one embodiment of the present invention has a structure in which a fused aromatic ring is fused to a furoquinoxaline skeleton or a thienoquinoxaline skeleton (i.e., a skeleton with a pyrazine ring), the organic compound has higher heat resistance and is more suitable for a light-emitting substance whose emission wavelength is a long wavelength than a structure in which the fused aromatic ring is fused to a furopyrimidine skeleton or a thienopyrimidine skeleton.

A light-emitting device used in a high-temperature environment, for example, in a car, is required to have high heat resistance. Also in the case where high temperature is applied during a product manufacturing process, for example, in a sealing step using glass frit, the light-emitting device is required to have high heat resistance. For these reasons, a material used for the light-emitting device needs to have a glass transition temperature (Tg) of 100° C. or higher, furthermore, 120° C. or higher in some cases. In one embodiment of the present invention, the Tg of the organic compound can be 100° C. or higher, furthermore, 120° C. or higher; accordingly, a material suitable for a light-emitting device that is required to have high heat resistance can be provided.

The organic compound of one embodiment of the present invention can be used as a host material, in which a light-emitting substance is dispersed, in a light-emitting device, for example.

The organic compound of one embodiment of the present invention has a high electron-transport property and thus can be used as an electron-transport material in a light-emitting device.

Specifically, one embodiment of the present invention is an organic compound represented by General Formula (G0). Note that not only organic compounds with the structures represented by the following general formulae, but also light-emitting device materials with the structures are each one embodiment of the present invention.

[Chemical Formula 12]

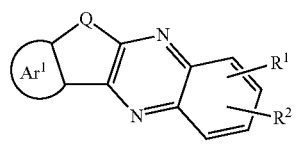

(G0)

In General Formula (G0), Q represents oxygen or sulfur, $Ar^1$ represents a substituted or unsubstituted fused aromatic ring, $R^1$ and $R^2$ each independently represent hydrogen or a group with 1 to 100, inclusive, carbon atoms in total, and at least one of $R^1$ and $R^2$ has a hole-transport skeleton.

Another embodiment of the present invention is an organic compound represented by General Formula (G0).

[Chemical Formula 13]

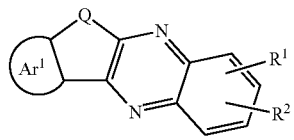

(G0)

In General Formula (G0), Q represents oxygen or sulfur, $Ar^1$ represents any one of a substituted or unsubstituted naphthalene ring, a substituted or unsubstituted phenanthrene ring, and a substituted or unsubstituted chrysene ring, $R^1$ and $R^2$ each independently represent hydrogen or a group with 1 to 100, inclusive, carbon atoms in total, and at least one of $R^1$ and $R^2$ has a hole-transport skeleton.

Preferably, the hole-transport skeleton included in at least one of $R^1$ and $R^2$ is any one of a substituted or unsubstituted diarylamino group, a substituted or unsubstituted fused aromatic hydrocarbon ring, and a substituted or unsubstituted π rich fused heteroaromatic ring.

The fused aromatic hydrocarbon ring preferably includes any one of a naphthalene skeleton, a fluorene skeleton, a triphenylene skeleton, and a phenanthrene skeleton.

The π rich fused heteroaromatic ring is preferably a fused heteroaromatic ring having any one of a dibenzothiophene skeleton, a dibenzofuran skeleton, and a carbazole skeleton. The reliability of a light-emitting device including a dibenzofuran skeleton or a dibenzothiophene skeleton can be more increased than that of one including a carbazole skeleton. The emission efficiency of a light-emitting device including a carbazole skeleton can be more increased than that of one including a dibenzofuran skeleton or a dibenzofuran skeleton.

In this specification and the like, the fused heteroaromatic ring in this specification and the like includes not only a carbazole ring, a dibenzothiophene ring, and a dibenzofuran ring but also a fused ring having a carbazole skeleton, a dibenzothiophene skeleton, or a dibenzofuran skeleton in a ring structure (i.e., a fused ring in which a ring is further fused to a carbazole skeleton, a dibenzothiophene skeleton, or a dibenzofuran skeleton), such as a benzocarbazole ring, a dibenzocarbazole ring, an indolocarbazole ring, a benzindolocarbazole ring, a dibenzindolocarbazole ring, a benzindolobenzocarbazole ring, a benzonaphthothiophene ring, or a benzonaphthofuran ring.

Another embodiment of the present invention is an organic compound represented by General Formula (G0).

[Chemical Formula 14]

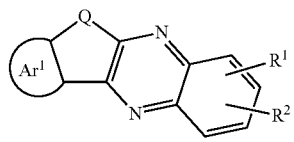

(G0)

In General Formula (G0), Q represents oxygen or sulfur, $Ar^1$ represents a substituted or unsubstituted fused aromatic ring, $R^1$ and $R^2$ each independently represent hydrogen or a group with 1 to 100, inclusive, carbon atoms in total, and at least one of $R^1$ and $R^2$ comprises a fused ring.

Another embodiment of the present invention is an organic compound represented by General Formula (G0).

[Chemical Formula 15]

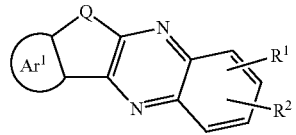

(G0)

In General Formula (G0), Q represents oxygen or sulfur, $Ar^1$ represents any one of a substituted or unsubstituted naphthalene ring, a substituted or unsubstituted phenanthrene ring, and a substituted or unsubstituted chrysene ring, $R^1$ and $R^2$ each independently represent hydrogen or a group with 1 to 100, inclusive, carbon atoms in total, and at least one of $R^1$ and $R^2$ has a fused ring.

Preferably, the fused ring included in at least one of $R^1$ and $R^2$ is any one of a substituted or unsubstituted fused aromatic hydrocarbon ring and a substituted or unsubstituted π rich fused heteroaromatic ring.

The fused ring is preferably a substituted or unsubstituted fused heteroaromatic ring including any one of a dibenzothiophene skeleton, a dibenzofuran skeleton, and a carbazole skeleton.

Note that as described above, the fused heteroaromatic ring in this specification and the like includes not only a carbazole ring, a dibenzothiophene ring, and a dibenzofuran ring but also a fused ring in which a ring is further fused to a carbazole skeleton, a dibenzothiophene skeleton, or a dibenzofuran skeleton.

The fused ring is preferably a substituted or unsubstituted fused aromatic hydrocarbon ring including any one of a naphthalene skeleton, a fluorene skeleton, a triphenylene skeleton, and a phenanthrene skeleton.

Another embodiment of the present invention is an organic compound represented by General Formula (G0).

[Chemical Formula 16]

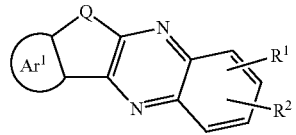

(G0)

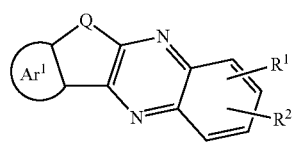

(u1)

$A^1$—$(\alpha)_n$—*

In General Formula (G0), Q represents oxygen or sulfur, $Ar^1$ represents a substituted or unsubstituted fused aromatic ring, $R^1$ and $R^2$ each independently represent hydrogen or a group with 1 to 100, inclusive, carbon atoms in total, at least one of $R^1$ and $R^2$ has a hole-transport skeleton, and at least one of $R^1$ and $R^2$ represents a structure represented by General Formula (u1). In General Formula (u1), α represents a substituted or unsubstituted arylene group with 6 to 25, inclusive, carbon atoms, n represents an integer greater than or equal to 0 and less than or equal to 4, $A^1$ represents any one of a substituted or unsubstituted aryl group with 6 to 30, inclusive, carbon atoms and a substituted or unsubstituted heteroaryl group with 3 to 30, inclusive, carbon atoms, and * represents a connection portion in General Formula (G0).

Another embodiment of the present invention is an organic compound represented by General Formula (G0).

[Chemical Formula 17]

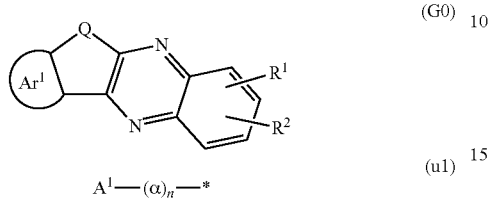

(G0)

(u1)

In General Formula (G0), Q represents oxygen or sulfur, $Ar^1$ represents any one of a substituted or unsubstituted naphthalene ring, a substituted or unsubstituted phenanthrene ring, and a substituted or unsubstituted chrysene ring, $R^1$ and $R^2$ each independently represent hydrogen or a group with 1 to 100, inclusive, carbon atoms in total, at least one of $R^1$ and $R^2$ has a hole-transport skeleton, and at least one of $R^1$ and $R^2$ represents a structure represented by General Formula (u1). In General Formula (u1), α represents a substituted or unsubstituted arylene group with 6 to 25, inclusive, carbon atoms, n represents an integer greater than or equal to 0 and less than or equal to 4, $A^1$ represents any one of a substituted or unsubstituted aryl group with 6 to 30, inclusive, carbon atoms and a substituted or unsubstituted heteroaryl group with 3 to 30, inclusive, carbon atoms, and * represents a connection portion in General Formula (G0).

In General Formula (u1), $A^1$ represents any one of General Formula ($A^1$-1) to General Formula ($A^1$-17).

[Chemical Formula 18]

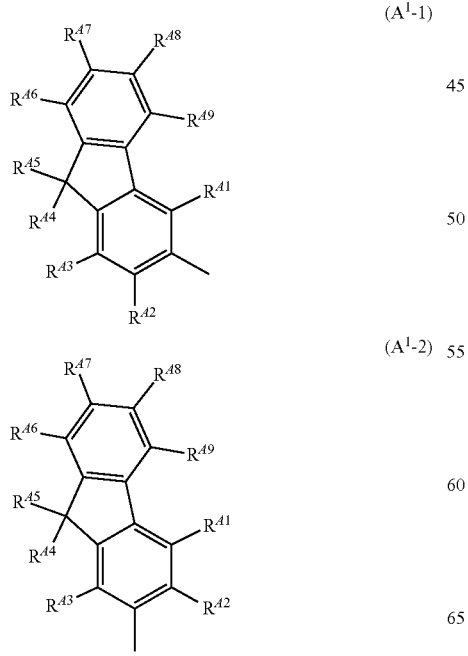

($A^1$-1)

($A^1$-2)

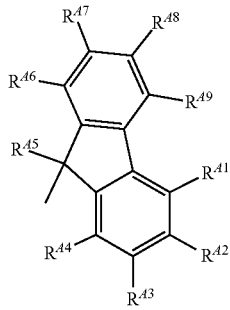

($A^1$-3)

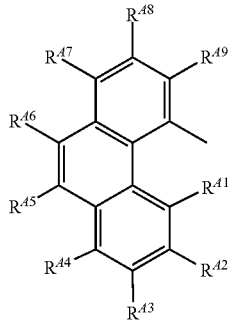

($A^1$-4)

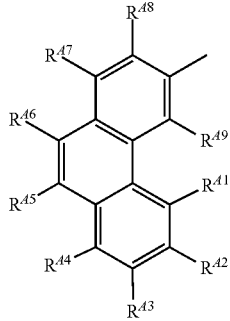

($A^1$-5)

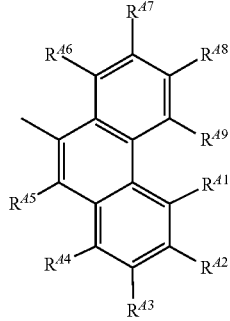

($A^1$-6)

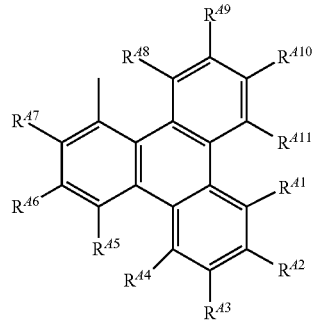

($A^1$-7)

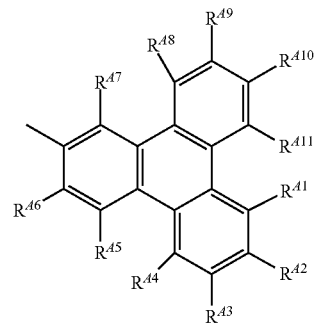
(A¹-8)
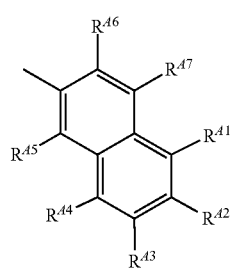
(A¹-9)
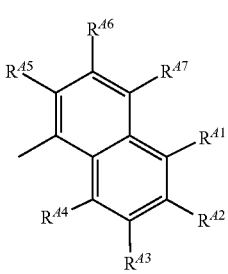
(A¹-10)
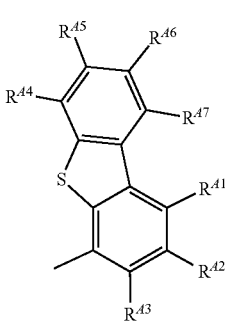
(A¹-11)
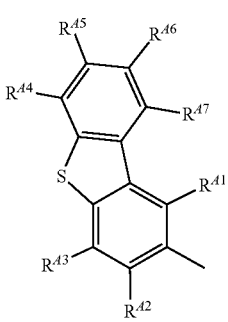
(A¹-12)
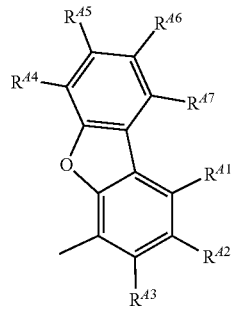
(A¹-13)
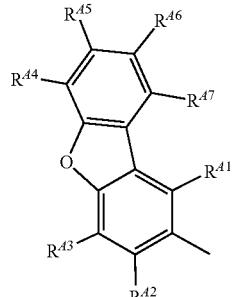
(A¹-14)
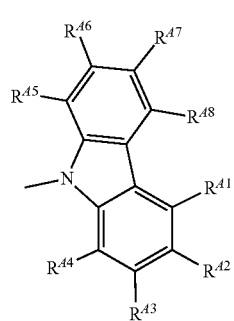
(A¹-15)
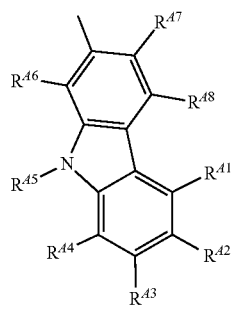
(A¹-16)
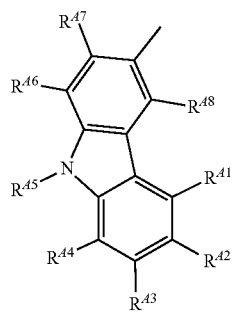
(A¹-17)
In General Formula (A¹-1) to General Formula (A¹-17) $R^{A1}$ to $R^{A11}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, and a substituted or unsubstituted aryl group with 6 to 30, inclusive, carbon atoms.

As the arylene group with 6 to 25, inclusive, carbon atoms in General Formula (u1), a phenylene group, a naphthalenediyl group, a biphenyldiyl group, an anthracenediyl group, a phenanthrenediyl group, a triphenylenediyl group, a 9H-fluorendiyl group, a 9,9-dimethylfluorendiyl group, a 9,9'-spirobifluorendiyl group, and the like can be given.

In General Formula (u1), a preferably represents any one of General Formula (Ar-1) to General Formula (Ar-14).

[Chemical Formula 19]

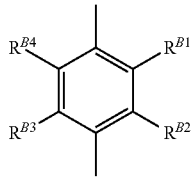
(Ar-1)

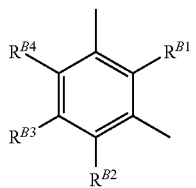
(Ar-2)

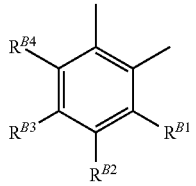
(Ar-3)

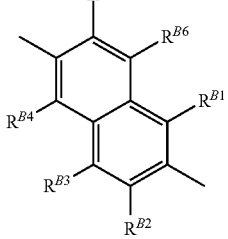
(Ar-4)

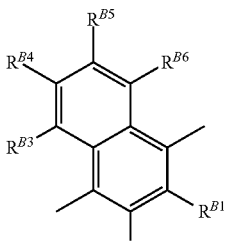
(Ar-5)

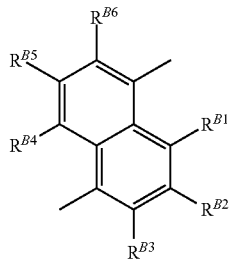
(Ar-6)

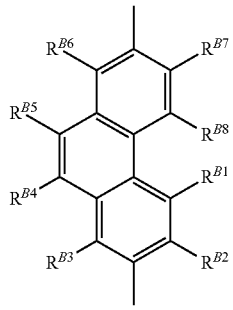
(Ar-7)

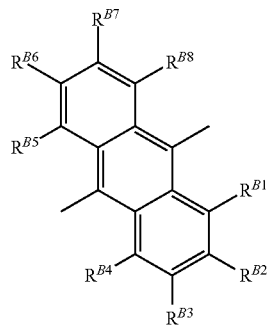
(Ar-8)

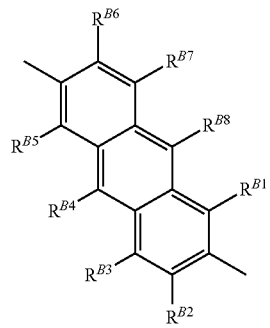
(Ar-9)

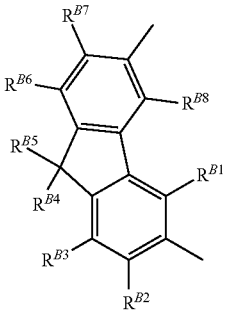
(Ar-10)

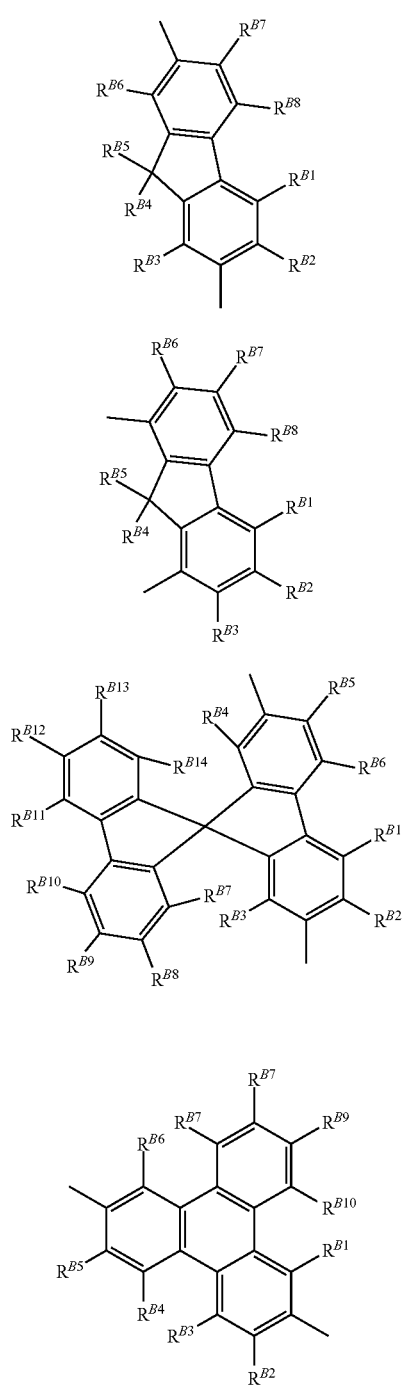

(Ar-11)

(Ar-12)

(Ar-13)

(Ar-14)

In General Formula (A¹-1) to General Formula (A¹-17), $R^{B1}$ to $R^{B14}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, and a substituted or unsubstituted aryl group with 6 to 30, inclusive, carbon atoms.

In each of the organic compounds of one embodiment of the present invention, $Ar^1$ in General Formula (G0) represents any one of General Formula (t1) to General Formula (t3).

[Chemical Formula 20]

(t1)

(t2)

(t3)

In General Formula (t1) to General Formula (t3), $R^3$ to $R^{24}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, a substituted or unsubstituted aryl group with 6 to 30, inclusive, carbon atoms, and * represents a connection portion in General Formula (G0).

As the organic compound represented by General Formula (G0), the organic compound represented by General Formula (G1) is preferred. This can further reduce the $T_1$ level of the organic compound.

[Chemical Formula 21]

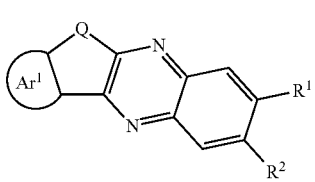

(G1)

In General Formula (G1), Q represents oxygen or sulfur, $Ar^1$ represents a substituted or unsubstituted fused aromatic ring (or any one of a substituted or unsubstituted naphthalene ring, a substituted or unsubstituted phenanthrene ring, and a substituted or unsubstituted chrysene ring), $R^1$ and $R^2$ each independently represent hydrogen or a group with 1 to 100, inclusive, carbon atoms in total, and at least one of $R^1$ and $R^2$ has a hole-transport skeleton or a fused ring, Any one of the organic compounds represented by General Formula (G1-1) to General Formula (G1-4) is particularly preferred among the organic compounds represented by General Formula (G0).

[Chemical Formula 22]

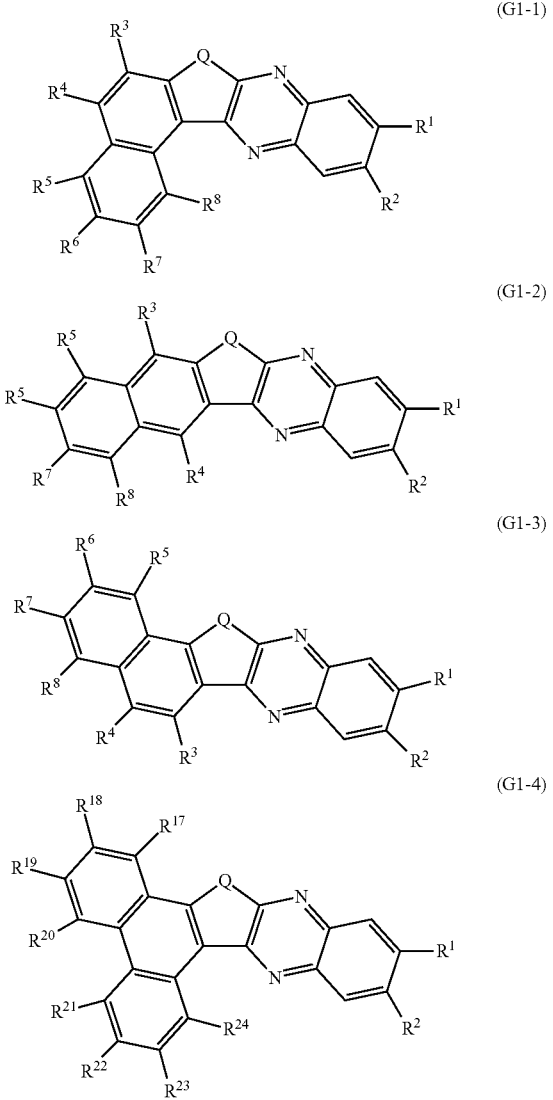

In General Formula (G1-1) to General Formula (G1-4), Q represents oxygen or sulfur, $R^1$ and $R^2$ each independently represent hydrogen or a group with 1 to 100, inclusive, carbon atoms in total, at least one of $R^1$ and $R^2$ has a hole-transport skeleton or a fused ring, and $R^3$ to $R^8$ and $R^{17}$ to $R^{24}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, and a substituted or unsubstituted aryl group with 6 to 30, inclusive, carbon atoms.

Note that as the group with 1 to 100, inclusive, carbon atoms in total, which is included in $R^1$ and $R^2$ in General Formula (G0), General Formula (G1), and General Formula (G1-1) to General Formula (G1-4), a substituted or unsubstituted alkyl group with 1 to 6, inclusive, carbon atoms, a substituted or unsubstituted cycloalkyl group with 3 to 7, inclusive, carbon atoms, a substituted or unsubstituted aryl group with 6 to 30, inclusive, carbon atoms, a substituted or unsubstituted heteroaryl group with 3 to 30, inclusive, carbon atoms, and the like can be given. Note that at least one of $R^1$ and $R^2$ has the hole-transport skeleton or the fused ring.

When X has a substituent in "substituted or unsubstituted X" (X refers to any of a variety of rings, skeletons, groups, and the like) in General Formula (G0), General Formula (G1), General Formula (t1) to General Formula (t3), General Formula (G1-1) to General Formula (G1-4), General Formula (u1), General Formula ($A^1$-1) to General Formula ($A^1$-17), and General Formula (Ar-1) to General Formula (Ar-14), the following can be given as the substituent: an alkyl group with 1 to 7, inclusive, carbon atoms, such as a methyl group, an ethyl group, a propyl group, an isopropyl group, a butyl group, an isobutyl group, a sec-butyl group, a tert-butyl group, a pentyl group, or a hexyl group; a cycloalkyl group with 5 to 7, inclusive, carbon atoms, such as a cyclopentyl group, a cyclohexyl group, a cycloheptyl group, or a 8,9,10-trinorbornanyl group; an aryl group with 6 to 12, inclusive, carbon atoms, such as a phenyl group, a naphthyl group, or a biphenyl group; and the like.

As the alkyl group with 1 to 6, inclusive, carbon atoms in General Formula (t1) to General Formula (t3), General Formula (G1-1) to General Formula (G1-4), General Formula ($A^1$-1) to General Formula ($A^1$-17), and General Formula (Ar-1) to General Formula (Ar-14), the following can be given: a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, a 2,3-dimethylbutyl group, an n-heptyl group, and the like.

As the cycloalkyl group with 3 to 7, inclusive, carbon atoms in General Formula (t1) to General Formula (t3), General Formula (G1-1) to General Formula (G1-4), General Formula ($A^1$-1) to General Formula ($A^1$-17), and General Formula (Ar-1) to General Formula (Ar-14), the following can be given: a cyclopropyl group, a cyclobutyl group, a cyclopentyl group, a cyclohexyl group, a 1-methylcyclohexyl group, a 2,6-dimethylcyclohexyl group, a cycloheptyl group, a cyclooctyl group, and the like.

As the aryl group with 6 to 30, inclusive, carbon atoms in General Formula (t1) to General Formula (t3), General Formula (G1-1) to General Formula (G1-4), General Formula (u1), General Formula ($A^1$-1) to General Formula ($A^1$-17), and General Formula (Ar-1) to General Formula (Ar-14), the following can be given: a phenyl group, an o-tolyl group, an m-tolyl group, ap-tolyl group, a mesityl group, an o-biphenyl group, an m-biphenyl group, a p-biphenyl group, a 1-naphthyl group, a 2-naphthyl group, a fluorenyl group, a 9,9-dimethylfluorenyl group, a spirofluorenyl group, a phenanthrenyl group, an anthracenyl group, a fluoranthenyl group, and the like.

The above description can be referred to for specific examples of the alkyl group with 1 to 6, inclusive, carbon atoms, the cycloalkyl group with 3 to 7, inclusive, carbon atoms, and the aryl group with 6 to 30, inclusive, carbon atoms in the group with 1 to 100, inclusive, carbon atoms in total included in $R^1$ and $R^2$ in General Formula (G0), General Formula (G1), and General Formula (G1-1) to General Formula (G1-4). As the heteroaryl group with 3 to 30, inclusive, carbon atoms in the group with 1 to 100, inclusive, carbon atoms in total and in General Formula (u1), the following can be given: monovalent groups such as a carbazolyl group, a benzocarbazolyl group, a dibenzocarbazolyl group, an indolocarbazolyl group, a benzoindolocarbazolyl group, a dibenzoindolocarbazolyl group, a benzindolobenzcarbazolyl group, a dibenzothienyl group, a benzonaphthothienyl group, a dibenzofuranyl group, and a benzonaphthofuranyl group.

Specific examples of the organic compound of one embodiment of the present invention include organic compounds represented by Structural Formula (100) to Structural Formula (117). Note that the present invention is not limited thereto.

[Chemical Formula 23]

(100)

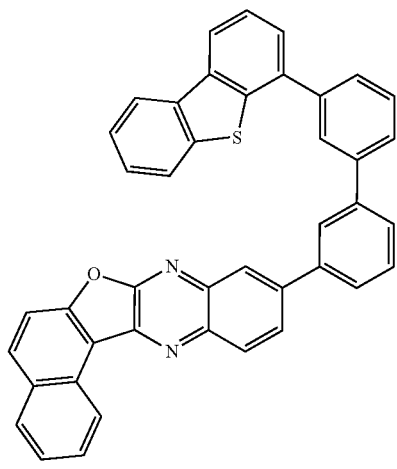

(101)

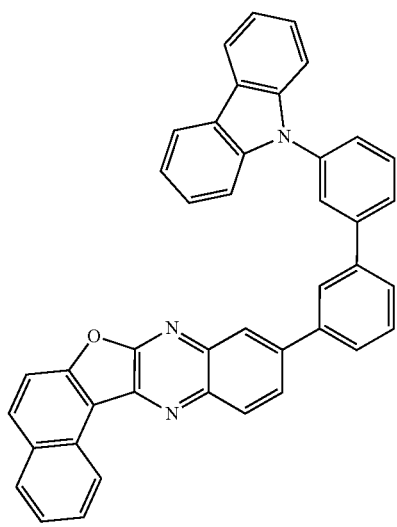

(102)

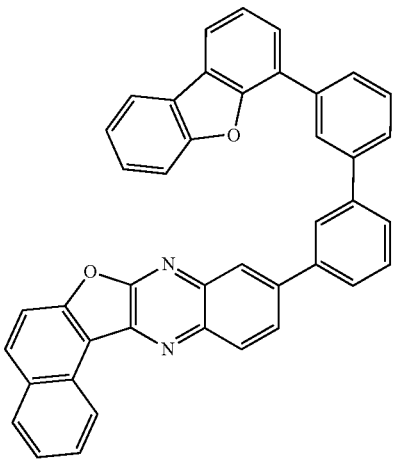

(103)

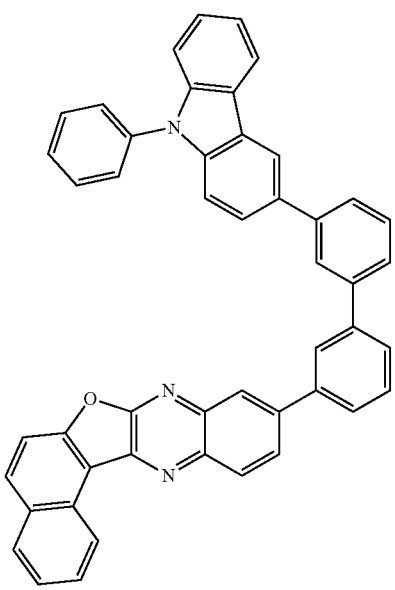

(104)

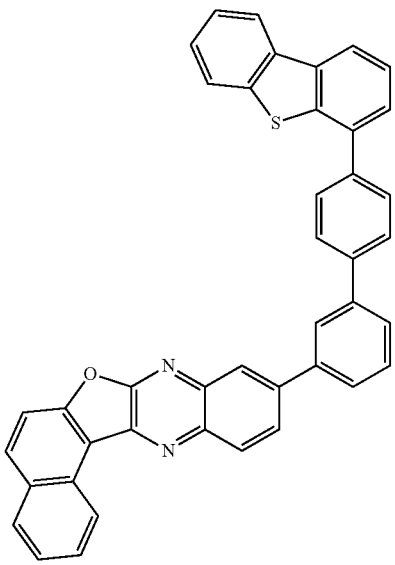

(105)
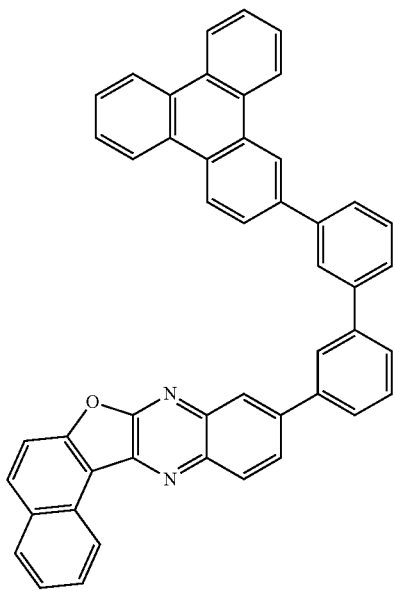
(106)
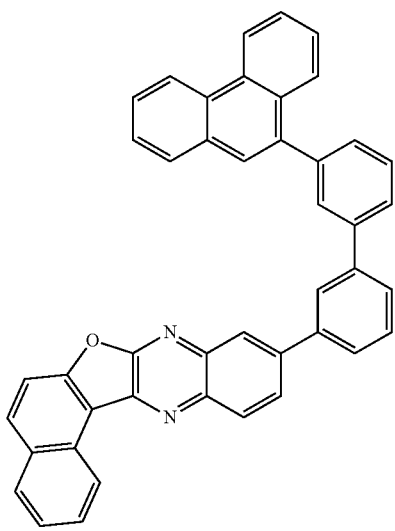
(107)
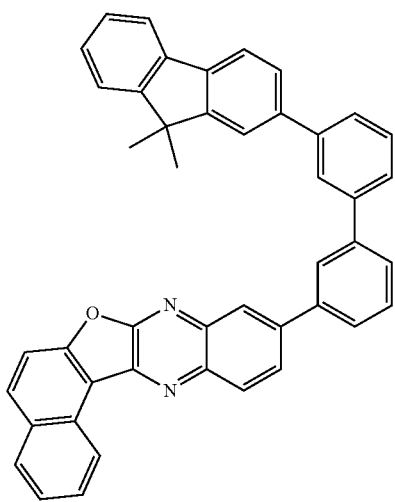
(108)
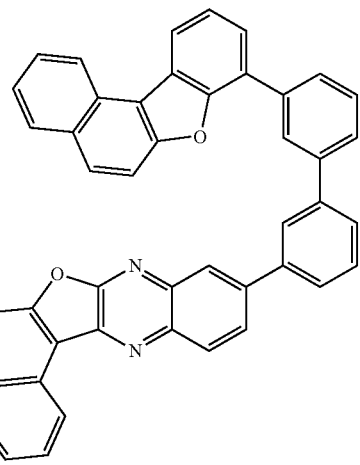
[Chemical Formula 24]
(109)
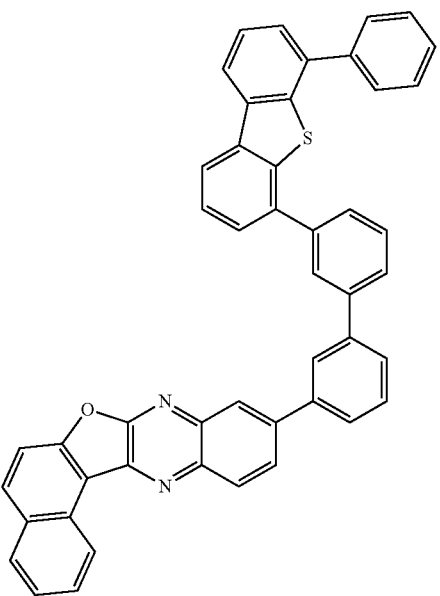

-continued
(110)
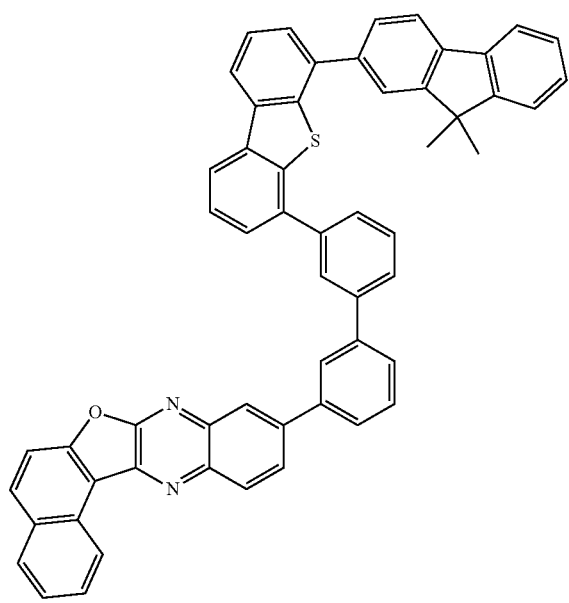
(111)
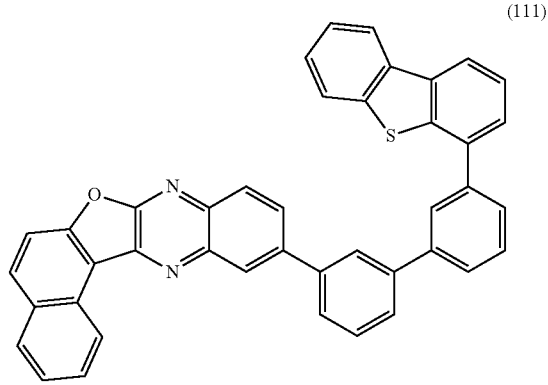
(112)
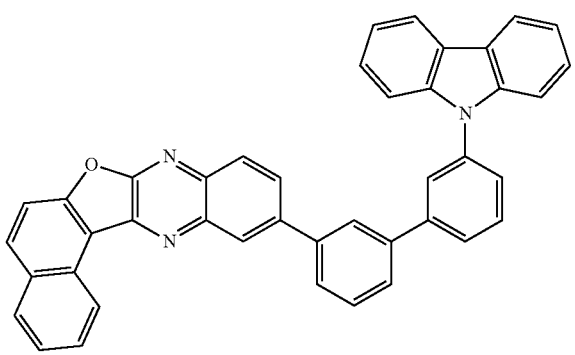
(113)
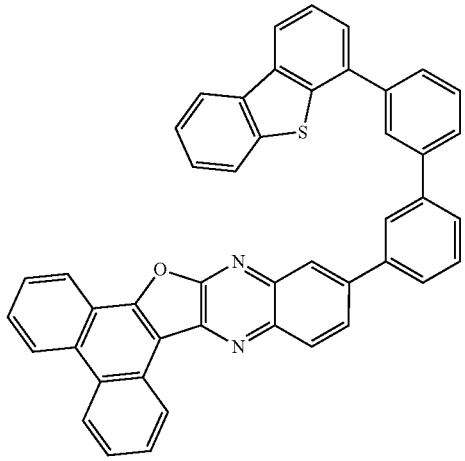
(114)
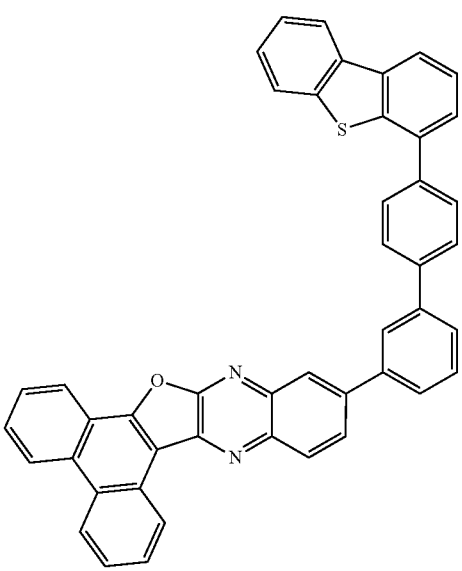
(115)
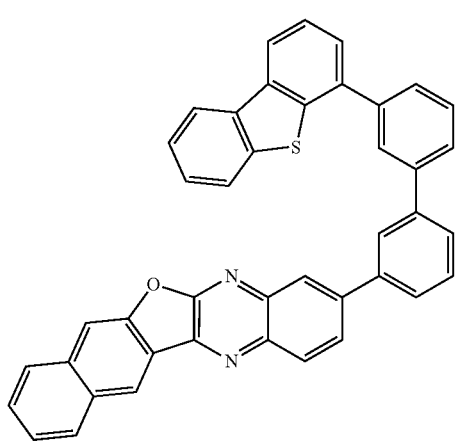

-continued (116)

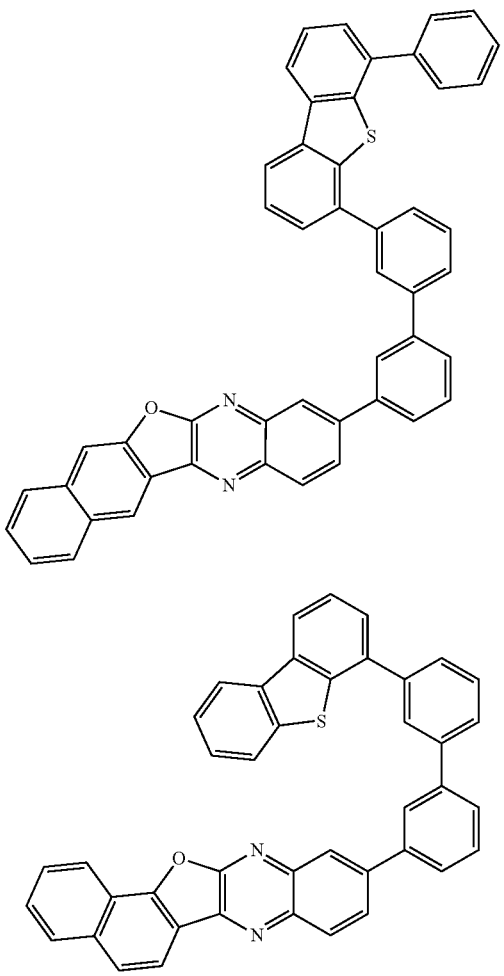

(117)

[Synthesis Method of Organic Compound of One Embodiment of Present Invention]

A variety of reactions can be employed as a method of synthesizing the organic compound of one embodiment of the present invention. A method of synthesizing the organic compound represented by General Formula (G0) is described below. First, an example of a method of synthesizing the organic compound represented by General Formula (G0') is described. Note that the organic compound represented by General Formula (G0') is a furoquinoxaline derivative to which a fused aromatic ring is fused or a thienoquinoxaline derivative to which a fused aromatic ring is fused, and is one embodiment of the organic compound represented by General Formula (G0).

[Chemical Formula 25]

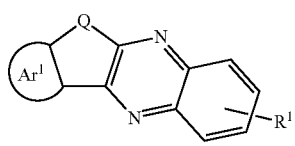

(G0')

In General Formula (G0'), Q represents oxygen or sulfur, $Ar^1$ represents a substituted or unsubstituted fused aromatic ring, $R^1$ represents a group with 1 to 100, inclusive, carbon atoms in total, and $R^1$ represents a hole-transport skeleton or a fused ring.

<<Example of Method of Synthesizing Organic Compound Represented by General Formula (G0')>>

First, as shown in Synthesis Scheme (A-1), a methyloxy group-substituted or methylthio group-substituted aryl boronic acid (a1) is coupled with an amino group-and-halogen-substituted quinoxaline derivative (a2) to give an intermediate (a3), and then the intermediate (a3) is reacted with tert-butyl nitrite and cyclized to give a furoquinoxaline derivative to which a fused aromatic ring is fused or a thienoquinoxaline derivative to which a fused aromatic ring is fused (a4). Note that when $Y^1$ in Synthesis Scheme (A-1) is a halogen, an intermediate (a5), which is obtained by further coupling with a boronic acid of an aromatic ring with a halogen $(Y^3-(\alpha)_n-B^2)$, can also be used in the subsequent reaction, like the quinoxaline derivative (a4).

[Chemical Formula 26]

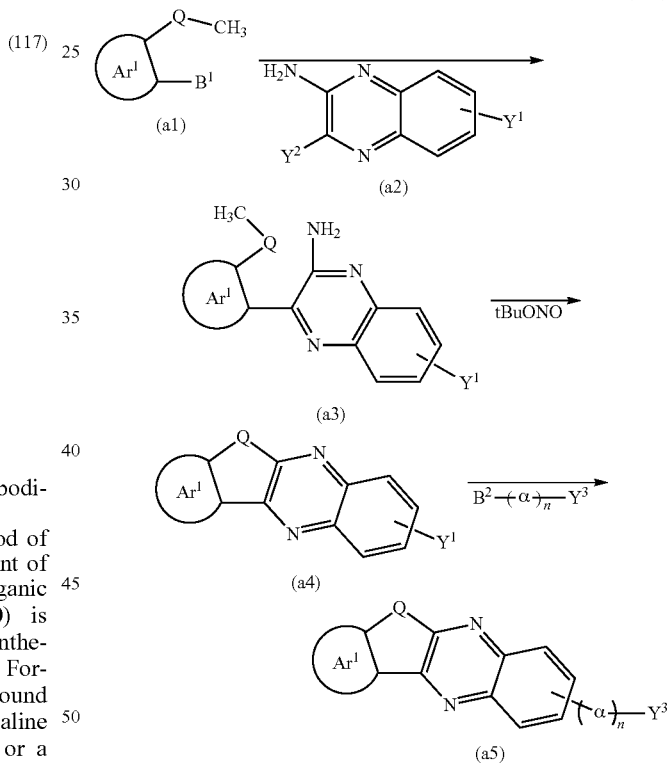

(A-1)

In Synthesis Scheme (A-1), Q represents oxygen or sulfur, $Ar^1$ represents a substituted or unsubstituted fused aromatic ring, $Y^1$ represents a halogen or an aromatic ring with a halogen, the number of $Y^1$ is one or two, $Y^2$ represents a halogen, $Y^3$ represents an aromatic ring with a halogen, the number of $Y^3$ is one or two, α represents a substituted or unsubstituted arylene group with 6 to 25, inclusive, carbon atoms, n represents an integer greater than or equal to 0 and less than or equal to 4, and $B^1$ and $B^2$ each represent a boronic acid, a boronic ester, a cyclic-triolborate salt, or the like. Note that as the cyclic-triolborate salt, a lithium salt, a potassium salt, or a sodium salt may be used.

The organic compounds represented by General Formula (a4) and General Formula (a5) in Synthesis Scheme (A-1)

are raw materials of the organic compound of one embodiment of the present invention, as shown below in Synthesis Scheme (A-2).

Next, as shown in Synthesis Scheme (A-2), the furoquinoxaline derivative to which a fused aromatic ring is fused or the thienoquinoxaline derivative to which a fused aromatic ring is fused (a4) obtained in Synthesis Scheme (A-1) is coupled with a boronic acid compound (b1) to give the organic compound represented by General Formula (G0').

[Chemical Formula 27]

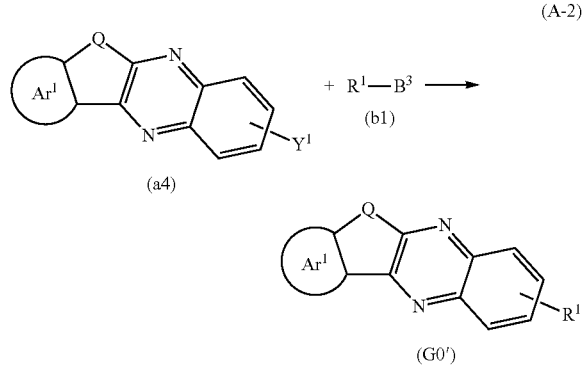

(A-2)

In Synthesis Scheme (A-2), Q represents oxygen or sulfur, $Ar^1$ represents a substituted or unsubstituted fused aromatic ring, $R^1$ represents a group with 1 to 10, inclusive, carbon atoms, $R^1$ includes a hole-transport skeleton, $Y^1$ represents one or two halogens, and $B^3$ represents a boronic acid, a boronic ester, a cyclic-triolborate salt, or the like. Note that as the cyclic-triolborate salt, a lithium salt, a potassium salt, or a sodium salt may be used.

Since various kinds of the methyloxy group-substituted or methylthio group-substituted aryl boronic acid (a1), the amino group-and-halogen-substituted quinoxaline derivative (a2), and the boronic acid compound (b1), which are used in Synthesis Schemes (A-1) and (A-2), are commercially available or can be synthesized, a great variety of the furoquinoxaline derivative to which a fused aromatic ring is fused or the thienoquinoxaline derivative to which a fused aromatic ring is fused, which is represented above by General Formula (G0'), can be synthesized. Thus, the organic compound of one embodiment of the present invention is characterized by having numerous variations.

Although the method of synthesizing the organic compound complex of one embodiment of the present invention is described above, the present invention is not limited thereto and synthesis may be performed by any other synthesis method.

As described above, the organic compound of one embodiment of the present invention has high heat resistance and is suitable as a light-emitting device material (particularly, a host material or an electron-transport material) which emits red light to near-infrared light. The use of the organic compound of one embodiment of the present invention can increase the emission efficiency of a light-emitting device that emits red light to near-infrared light. The use of the organic compound of one embodiment of the present invention can increase the lifetime of a light-emitting device that emits red light to near-infrared light. The use of the organic compound of one embodiment of the present invention can increase the heat resistance of a light-emitting device that emits red light to near-infrared light. The use of the organic compound of one embodiment of the present invention can increase the reliability of a light-emitting device that emits red light to near-infrared light.

This embodiment can be combined with the other embodiments as appropriate. In this specification, in the case where a plurality of structure examples are shown in one embodiment, the structure examples can be combined as appropriate.

Embodiment 2

In this embodiment, a light-emitting device of one embodiment of the present invention is described below with reference to FIG. 1. In this embodiment, a light-emitting device having a function of emitting visible light or near-infrared light is described.

[Structure Example of Light-Emitting Device]
<<Basic Structure of Light-Emitting Device>>

FIG. 1A to FIG. 1D illustrate examples of a light-emitting device including an EL layer between a pair of electrodes.

The light-emitting device illustrated in FIG. 1A has a structure in which an EL layer 103 is provided between a first electrode 101 and a second electrode 102 (a single structure). The EL layer 103 includes at least a light-emitting layer.

Figure 1B:
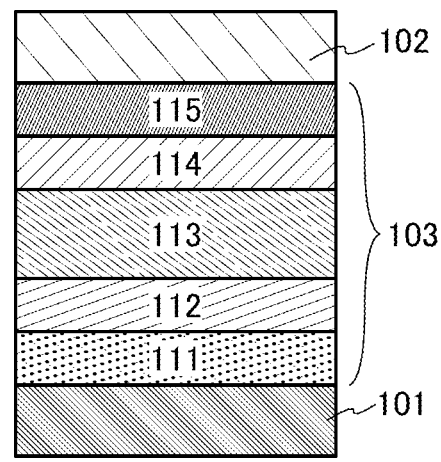

FIG. 1B shows an example of a stacked-layer structure of the EL layer 103. In this embodiment, the case where the first electrode 101 functions as an anode and the second electrode 102 functions as a cathode is described as an example. The EL layer 103 has a structure in which a hole-injection layer 111, a hole-transport layer 112, a light-emitting layer 113, an electron-transport layer 114, and an electron-injection layer 115 are stacked in this order over the first electrode 101. Each of the hole-injection layer 111, the hole-transport layer 112, the light-emitting layer 113, the electron-transport layer 114, and the electron-injection layer 115 may have a single-layer structure or a stacked-layer structure. When the first electrode 101 serves as a cathode and the second electrode 102 serves as an anode, the stacking order is reversed.

A light-emitting device may include a plurality of EL layers between a pair of electrodes. For example, it is preferable that the light-emitting device include n EL layers (n is an integer greater than or equal to 2) and a charge-generation layer 104 be provided between an (n−1)th EL layer and an n-th EL layer.

Figure 1C:
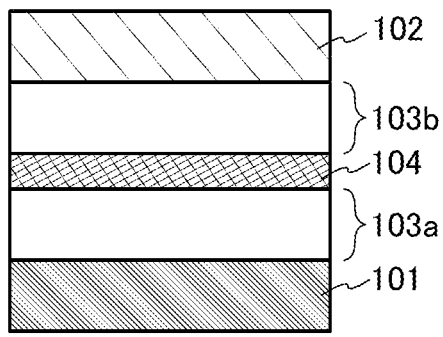
Figure 1D:
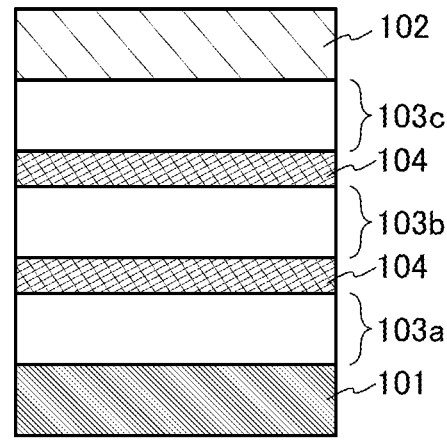

FIG. 1C illustrates a light-emitting device with a tandem structure in which two EL layers (EL layers 103a and 103b) are provided between a pair of electrodes. FIG. 1D illustrates a light-emitting device with a tandem structure in which three EL layers (EL layers 103a, 103b, and 103c) are provided.

Each of the EL layers 103a, 103b, and 103c includes at least a light-emitting layer. Note that in the case where a plurality of EL layers are provided as in the tandem structure illustrated in FIG. 1C and FIG. 1D, each of the EL layers can have a stacked-layer structure similar to that of the EL layer 103 illustrated in FIG. 1B. Each of the EL layers 103a, 103b, and 103c can include one or more kinds of the hole-injection layer 111, the hole-transport layer 112, the electron-transport layer 114, and the electron-injection layer 115.

The charge-generation layer 104 illustrated in FIG. 1C has a function of injecting electrons into one of the EL layer 103a and the EL layer 103b and injecting holes into the other of the EL layers when voltage is applied to the first electrode 101 and the second electrode 102. Thus, when voltage is applied in FIG. 1C such that the potential of the first electrode 101 is higher than that of the second electrode 102, the charge-generation layer 104 injects electrons into the EL layer 103a and injects holes into the EL layer 103b.

Note that in terms of light extraction efficiency, the charge-generation layer 104 preferably transmits visible light or near-infrared light (specifically, the transmittance of visible light or near-infrared light of the charge-generation layer 104 is preferably 40% or higher). The charge-generation layer 104 functions even when having lower conductivity than the first electrode 101 and the second electrode 102.

When the EL layers are provided in contact with each other and this shapes the same structure as a charge-generation layer 104, the EL layers can be provided in contact with each other without the charge-generation layer therebetween. For example, when a charge-generation region is formed over a surface of the EL layer, an EL layer can be provided in contact with the surface.

A tandem-structured light-emitting device has higher current efficiency than a single-structured light-emitting device, and needs a smaller amount of current when the devices emit light with the same luminance. Accordingly, the lifetime of the light-emitting device is long, and the display apparatus and the electronic device can have high reliability.

The light-emitting layer 113 contains a light-emitting substance and a plurality of substances in appropriate combination, whereby fluorescence or phosphorescence with a desired wavelength can be obtained. The light-emitting layer 113 may be a stack of layers having different emission wavelengths. In this case, different materials may be used for the light-emitting substance and other substances used in each of the light-emitting layers that are stacked. The EL layers 103a, 103b, and 103c illustrated in FIG. 1C and FIG. 1D may be configured to exhibit light with different wavelengths. Also in that case, the light-emitting substance and other substances are different between the light-emitting layers. For example, in the structure of FIG. 1C, when the EL layer 103a emits red light and green light and the EL layer 103b emits blue light, the light-emitting device can emit white light as a whole. In one light-emitting device, a plurality of light-emitting layers or a plurality of EL layers may emit light of the same color. For example, in the structure of FIG. 1D, when the EL layer 103a emits first blue light, the EL layer 103b emits yellow light or yellowish green light and red light, and the EL layer 103c emits second blue light, the light-emitting device can emit white light as a whole.

The light-emitting device of one embodiment of the present invention may be configured such that light obtained from the EL layer is resonated between the pair of electrodes in order to intensify the light. For example, when the first electrode 101 is formed as a reflective electrode and the second electrode 102 is formed as a transflective electrode in FIG. 1B to form a micro optical resonator (microcavity) structure, light obtained from the EL layer 103 can be intensified.

With the use of the microcavity structure for the light-emitting device, light with different wavelengths (monochromatic light) can be extracted even if the same EL layer is used. Thus, formation of functional layers for respective pixels (what is called separate coloring) is not necessary for obtaining different emission colors. Therefore, high definition can be easily achieved. A combination with coloring layers (color filters) is also possible. Furthermore, the emission intensity of light with a specific wavelength in the front direction can be increased, whereby power consumption can be reduced.

Note that in the case where the first electrode 101 of the light-emitting device is a reflective electrode having a stacked-layer structure of a conductive film having a property of reflecting visible light or near-infrared light and a conductive film having a property of transmitting visible light or near-infrared light, optical adjustment can be performed by controlling the thicknesses of the conductive film having the transmitting property. Specifically, when the wavelength of light obtained from the light-emitting layer 113 is $\lambda$, the distance between the first electrode 101 and the second electrode 102 is preferably adjusted to around $m\lambda/2$ (m is a natural number).

To amplify desired light (wavelength: $\lambda$) obtained from the light-emitting layer 113, the optical distance from the first electrode 101 to a region where the desired light is obtained in the light-emitting layer 113 (a light-emitting region) and the optical distance from the second electrode 102 to the region where the desired light is obtained in the light-emitting layer 113 (the light-emitting region) are preferably adjusted to around $(2m'+1)\lambda/4$ (m' is a natural number). Here, the light-emitting region refers to a region where holes and electrons are recombined in the light-emitting layer 113.

By performing such optical adjustment, the spectrum of light obtained from the light-emitting layer 113 can be narrowed, and light emission with high color purity can be obtained.

Note that in the above case, the optical distance between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained with given positions in the first electrode 101 and the second electrode 102 being supposed to be reflective regions. Furthermore, the optical distance between the first electrode 101 and the light-emitting layer from which the desired light is obtained is, to be exact, the optical distance between the reflective region in the first electrode 101 and the light-emitting region in the light-emitting layer from which the desired light is obtained. However, it is difficult to precisely determine the reflective region in the first electrode 101 and the light-emitting region in the light-emitting layer from which the desired light is obtained; thus, it is assumed that the above effect can be sufficiently obtained with a given position in the first electrode 101 being supposed to be the reflective region and a given position in the light-emitting layer from which the desired light is obtained being supposed to be the light-emitting region.

At least one of the first electrode 101 and the second electrode 102 has a property of transmitting visible light or near-infrared light. The transmissivity of visible light or near-infrared light of the electrode having a property of transmitting visible light or near-infrared light is higher than or equal to 40%. In the case where the electrode having a transmitting property with respect to visible light or near-infrared light is the above-described transflective electrode, the reflectance of visible light or near-infrared light of the electrode is higher than or equal to 20% and lower than or equal to 80%, preferably higher than or equal to 40% and lower than or equal to 70%. These electrodes preferably have a resistivity less than or equal to $1\times10^{-2}$ $\Omega$cm.

When the first electrode 101 or the second electrode 102 is an electrode having a property of reflecting visible light or near-infrared light (a reflective electrode), the reflectance of visible light or near-infrared light of the reflective electrode is higher than or equal to 40% and lower than or equal to 100%, preferably higher than or equal to 70% and lower than or equal to 100%. This electrode preferably has a resistivity less than or equal to $1\times10^{-2}$ Ωcm.

<<Specific Structure of Light-Emitting Device>>

Next, a specific structure of the light-emitting device will be described. Here, the light-emitting device having the single structure illustrated in FIG. 1B is used for the description.

<First Electrode and Second Electrode>

As materials for forming the first electrode 101 and the second electrode 102, any of the following materials can be used in an appropriate combination as long as the functions of the electrodes described above can be fulfilled. For example, a metal, an alloy, an electrically conductive compound, a mixture of these, and the like can be used as appropriate. Specific examples include In—Sn oxide (also referred to as ITO), In—Si—Sn oxide (also referred to as ITSO), In—Zn oxide, and In—W—Zn oxide. In addition, it is possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use a Group 1 element or a Group 2 element in the periodic table, which is not described above (e.g., lithium (Li), cesium (Cs), calcium (Ca), or strontium (Sr)), a rare earth metal such as europium (Eu) or ytterbium (Yb), an alloy containing an appropriate combination of any of these, graphene, or the like.

Note that when a light-emitting device having a microcavity structure is formed, the first electrode 101 is formed as a reflective electrode and the second electrode 102 is formed as a transflective electrode. Thus, a single layer or stacked layers can be formed using one or more desired conductive materials. Note that the second electrode 102 is formed after formation of the EL layer 103, with the use of a material selected as described above. For fabrication of these electrodes, a sputtering method or a vacuum evaporation method can be used.

<Hole-Injection Layer and Hole-Transport Layer>

The hole-injection layer 111 is a layer injecting holes from the first electrode 101 serving as the anode to the EL layer 103, and is a layer including a material with a high hole-injection property.

As the material with a high hole-injection property, a transition metal oxide such as molybdenum oxide, vanadium oxide, ruthenium oxide, tungsten oxide, or manganese oxide or a phthalocyanine-based compound such as phthalocyanine (abbreviation: H$_2$Pc) or copper phthalocyanine (abbreviation: CuPc) can be used, for example.

As the material with a high hole-injection property, it is possible to use, for example, an aromatic amine compound such as 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), or 3-[N-(1-naphthyl)-N-(9-phenylcarbazol-3-yl)amino]-9-phenylcarbazole (abbreviation: PCzPCN1).

As the material with a high hole-injection property, it is possible to use, for example, poly(N-vinylcarbazole) (abbreviation: PVK), poly(-vinyltriphenylamine) (abbreviation: PVTPA), poly[N-(4-{N'-[4-(4-diphenylamino)phenyl]phenyl-N-phenylamino}phenyl)methacrylamide] (abbreviation: PTPDMA), or poly[N,N'-bis(4-butylphenyl)-N,N'-bis(phenyl)benzidine](abbreviation: Poly-TPD); or it is also possible to use, for example, a high molecular compound to which acid is added, such as poly(3,4-ethylenedioxythiophene)/poly(styrenesulfonic acid) (abbreviation: PEDOT/PSS) or polyaniline/poly(styrenesulfonic acid) (PAni/PSS).

As the material with a high hole-injection property, a composite material containing a hole-transport material and an acceptor material (an electron-accepting material) can also be used. In this case, the acceptor material extracts electrons from the hole-transport material, so that holes are generated in the hole-injection layer 111 and the holes are injected into the light-emitting layer 113 through the hole-transport layer 112. Note that the hole-injection layer 111 may be formed using a single layer of a composite material containing a hole-transport material and an acceptor material, or may be formed using a stack including a layer of a hole-transport material and a layer of an acceptor material.

The hole-transport layer 112 is a layer transporting holes, which are injected from the first electrode 101 by the hole-injection layer 111, to the light-emitting layer 113. The hole-transport layer 112 is a layer including a hole-transport material. It is particularly preferable that the highest occupied molecular orbital level (HOMO level) of the hole-transport material used in the hole-transport layer 112 be the same as or close to the HOMO level of the hole-injection layer 111.

As the acceptor material used for the hole-injection layer 111, an oxide of a metal belonging to any of Group 4 to Group 8 of the periodic table can be used. Specific examples include molybdenum oxide, vanadium oxide, niobium oxide, tantalum oxide, chromium oxide, tungsten oxide, manganese oxide, and rhenium oxide. Among these, molybdenum oxide is particularly preferable since it is stable in the air, has a low hygroscopic property, and is easy to handle; or organic acceptors such as a quinodimethane derivative, a chloranil derivative, and a hexaazatriphenylene derivative can be used. Examples of compounds having an electron-withdrawing group (halogen group or cyano group) include 7,7,8,8-tetracyano-2,3,5,6-tetrafluoroquinodimethane (abbreviation: F$_4$-TCNQ), chloranil, 2,3,6,7,10,11-hexacyano-1,4,5,8,9,12-hexaazatriphenylene (abbreviation: HAT-CN), and 1,3,4,5,7,8-hexafluorotetracyano-naphthoquinodimethane (abbreviation: F6-TCNNQ). A compound in which electron-withdrawing groups are bonded to a fused aromatic ring having a plurality of hetero atoms, such as HAT-CN, is particularly preferable because it is thermally stable. A [3]radialene derivative including an electron-withdrawing group (in particular, a cyano group or a halogen group such as a fluoro group) has a very high electron-accepting property and thus is preferred; specific examples include α,α,α''-1,2,3-cyclopropanetriylidenetris[4-cyano-2,3,5,6-tetrafluorobenzeneacetonitrile], α,α,α''-1,2,3-cyclopropanetriylidenetris[2,6-dichloro-3,5-difluoro-4-(trifluoromethyl)benzeneacetonitrile], and α,α,α''-1,2,3-cyclopropanetriylidenetris[2,3,4,5,6-pentafluorobenzeneacetonitrile].

The hole-transport materials used for the hole-injection layer 111 and the hole-transport layer 112 are preferably substances with a hole mobility greater than or equal to $10^{-6}$ cm$^2$/Vs. Note that other substances can also be used as long as they have a property of transporting more holes than electrons.

As the hole-transport material, materials having a high hole-transport property, such as a π-electron-rich heteroaromatic compound (e.g., a carbazole derivative, a thiophene derivative, and a furan derivative) and an aromatic amine (a compound having an aromatic amine skeleton), are preferable.

Examples of the carbazole derivative (a compound having a carbazole skeleton) include a bicarbazole derivative (e.g., a 3,3'-bicarbazole derivative) and an aromatic amine having a carbazolyl group.

Specific examples of the bicarbazole derivative (e.g., a 3,3'-bicarbazole derivative) include 3,3'-bis(9-phenyl-9H-carbazole) (abbreviation: PCCP), 9,9'-bis(1,1'-biphenyl-4-yl)-3,3'-bi-9H-carbazole, 9,9'-bis(1,1'-biphenyl-3-yl)-3,3'-bi-9H-carbazole, 9-(1,1'-biphenyl-3-yl)-9'-(1,1'-biphenyl-4-yl)-9H,9'H-3,3'-bicarbazole (abbreviation: mBPCCBP), and 9-(2-naphthyl)-9'-phenyl-9H,9'H-3,3'-bicarbazole (abbreviation: βNCCP).

Specific examples of the aromatic amine having a carbazolyl group include 4-phenyl-4'-(9-phenyl-9H-carbazol-3-yl)triphenylamine (abbreviation: PCBA1BP), N-(4-biphenyl)-N-(9,9-dimethyl-9H-fluoren-2-yl)-9-phenyl-9H-carbazol-3-amine (abbreviation: PCBiF), N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 4-phenyldiphenyl-(9-phenyl-9H-carbazol-3-yl)amine (abbreviation: PCA1BP), N,N'-bis(9-phenylcarbazol-3-yl)-N,N'-diphenylbenzene-1,3-diamine (abbreviation: PCA2B), N,N',N"-triphenyl-N,N',N"-tris(9-phenylcarbazol-3-yl)benzene-1,3,5-triamine (abbreviation: PCA3B), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), PCzPCA1, PCzPCA2, PCzPCN1, 3[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 3,6-bis[N-(4-diphenylaminophenyl)-N-(1-naphthyl)amino]-9-phenylcarbazole (abbreviation: PCzTPN2), 2[N-(9-phenylcarbazol-3-yl)-N-phenylamino]spiro-9,9'-bifluorene (abbreviation: PCASF), N-[4-(9H-carbazol-9-yl)phenyl]-N-(4-phenyl)phenylaniline (abbreviation: YGA1BP), N,N'-bis[4-(carbazol-9-yl)phenyl]-N,N'-diphenyl-9,9-dimethylfluorene-2,7-diamine (abbreviation: YGA2F), and 4,4',4"-tris(carbazol-9-yl)triphenylamine (abbreviation: TCTA).

In addition to the above, other examples of the carbazole derivative include 3-[4-(9-phenanthryl)-phenyl]-9-phenyl-9H-carbazole (abbreviation: PCPPn), 3-[4-(1-naphthyl)-phenyl]-9-phenyl-9H-carbazole (abbreviation: PCPN), 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA).

Specific examples of the thiophene derivative (a compound having a thiophene skeleton) and the furan derivative (a compound having a furan skeleton) include compounds having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV), 4,4',4"-(benzene-1,3,5-triyl)tri(dibenzofuran) (abbreviation: DBF3P-II), and 4-{3-[3-(9-phenyl-9H-fluoren-9-yl)phenyl]phenyl}dibenzofuran (abbreviation: mmDBFFLBi-II).

Specific examples of the aromatic amine include 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), N-(9,9-dimethyl-9H-fluoren-2-yl)-N-{9,9-dimethyl-2-[N'-phenyl-N'-(9,9-dimethyl-9H-fluoren-2-yl) amino]-9H-fluoren-7-yl}phenylamine (abbreviation: DFLADFL), N-(9,9-dimethyl-2-diphenylamino-9H-fluoren-7-yl)diphenylamine (abbreviation: DPNF), 2-[N-(4-diphenylaminophenyl)-N-phenylamino]spiro-9,9'-bifluorene (abbreviation: DPASF), 2,7-bis[N-(4-diphenylaminophenyl)-N-phenylamino]spiro-9,9'-bifluorene (abbreviation: DPA2SF), 4,4',4"-tris[N-(1-naphthyl)-N-phenylamino]triphenylamine (abbreviation: 1'-TNATA), TDATA, m-MTDATA, N,N'-di(p-tolyl)-N,N'-diphenyl-p-phenylenediamine (abbreviation: DTDPPA), DPAB, DNTPD, and DPA3B.

As the hole-transport material, a high molecular compound such as PVK, PVTPA, PTPDMA, or Poly-TPD can also be used.

The hole-transport material is not limited to the above examples, and one of or a combination of various known materials can be used as the hole-transport material in the hole-injection layer 111 and the hole-transport layer 112.

<Light-Emitting Layer>

The light-emitting layer 113 is a layer including a light-emitting substance. The light-emitting layer 113 can include one or more kinds of light-emitting substances. As the light-emitting substance, a substance that exhibits an emission color of blue, purple, bluish purple, green, yellowish green, yellow, orange, red, or the like is appropriately used. As the light-emitting substance, a substance that emits near-infrared light can also be used. When different light-emitting substances are used for a plurality of light-emitting layers, different emission colors can be exhibited (for example, complementary emission colors are combined to obtain white light emission). Furthermore, a stacked-layer structure in which one light-emitting layer includes different light-emitting substances may be employed.

The light-emitting layer 113 preferably contains one or more kinds of organic compounds (e.g., a host material and an assist material) in addition to the light-emitting substance (guest material). As the one or more kinds of organic compounds, the light-emitting device of one embodiment of the present invention preferably includes the organic compound of one embodiment of the present invention described in Embodiment 1. As the one or more kinds of organic compounds, one or both of the hole-transport material and the electron-transport material described in this embodiment can be used. As the one or more kinds of organic compounds, a bipolar material may be used.

There is no particular limitation on the light-emitting substance that can be used for the light-emitting layer 113, and it is possible to use a light-emitting substance that converts singlet excitation energy into light emission in the visible light range or the near-infrared light range or a light-emitting substance that converts triplet excitation energy into light emission in the visible light range or the near-infrared light range.

As an example of the light-emitting substance that converts singlet excitation energy into light, a substance that exhibits fluorescence (a fluorescent material) can be given; examples include a pyrene derivative, an anthracene derivative, a triphenylene derivative, a fluorene derivative, a carbazole derivative, a dibenzothiophene derivative, a dibenzofuran derivative, a dibenzoquinoxaline derivative, a quinoxaline derivative, a pyridine derivative, a pyrimidine derivative, a phenanthrene derivative, and a naphthalene derivative. A pyrene derivative is particularly preferable because it has a high emission quantum yield. Specific examples of the pyrene derivative include N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-diphenyl-N,N'-bis[4-(9-phenyl-9H-fluoren-9-yl)phenyl]pyrene-1,6-diamine (abbreviation: 1,6FLPAPrn), N,N'-bis(dibenzofuran-2-yl)-N,N'-diphenylpyrene-1,6-diamine (abbreviation: 1,6FrAPrn), N,N'-bis(dibenzothiophen-2-yl)-N,N'-diphenylpyrene-1,6-diamine (abbreviation: 1,6ThAPrn), N,N'-(pyrene-1,6-diyl)bis[(N-phenylbenzo[b]naphtho[1,2-d]furan)-6-amine](abbreviation: 1,6BnfAPrn), N,N'-(pyrene-1,6-diyl)bis[(N-phenylbenzo[b]naphtho[1,2-d]furan)-8-amine](abbreviation: 1,6BnfAPrn-02), and N,N'-(pyrene-1,6-diyl)bis[(6,N-diphenylbenzo[b]naphtho[1,2-d]furan)-8-amine](abbreviation: 1,6BnfAPrn-03).

In addition, it is possible to use 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), 4-(10-phenyl-9-anthryl)-4'-(9-phenyl-9H-carbazol-3-yl)triphenylamine (abbreviation: PCBAPA), 4-[4-(10-phenyl-9-anthryl)phenyl]-4'-(9-phenyl-9H-carbazol-3-yl)triphenylamine (abbreviation: PCBAPBA), perylene, 2,5,8,11-tetra(tert-butyl)perylene (abbreviation: TBP), N,N'-(2-tert-butylanthracene-9,10-diyldi-4,1-phenylene)bis[N,N',N'-triphenyl-1,4-phenylenediamine](abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), or the like.

Examples of the light-emitting substance that converts triplet excitation energy into light include a substance that exhibits phosphorescence (a phosphorescent material) and a thermally activated delayed fluorescence (TADF) material that exhibits thermally activated delayed fluorescence.

Examples of a phosphorescent material include an organometallic complex, a metal complex (platinum complex), and a rare earth metal complex. These substances exhibit different emission colors (emission peaks), and thus are used through appropriate selection as needed.

As a phosphorescent material that exhibits blue or green and whose emission spectrum has a peak wavelength at greater than or equal to 450 nm and less than or equal to 570 nm, the following substances can be given.

The examples include organometallic complexes including a 4H-triazole skeleton, such as tris{2-[5-(2-methylphenyl)-4-(2,6-dimethylphenyl)-4H-1,2,4-triazol-3-yl-κ$N^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), tris[4-(3-biphenyl)-5-isopropyl-3-phenyl-4H-1,2,4-triazolato]iridium(III) (abbreviation: [Ir(iPrptz-3b)$_3$]), and tris[3-(5-biphenyl)-5-isopropyl-4-phenyl-4H-1,2,4-triazolato]iridium(III) (abbreviation: Ir(iPr5btz)$_3$]); organometallic complexes including a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic complexes including an imidazole skeleton, such as fac-tris[1-(2,6-diisopropylphenyl)-2-phenyl-1H-imidazole]iridium(III) (abbreviation: [Ir(iPrpmi)$_3$]), and tris[3-(2,6-dimethylphenyl)-7-methylimidazo[1,2-f]phenanthridinato]iridium(III) (abbreviation: [Ir(dmpimpt-Me)$_3$]); organometallic complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: [Ir(CF$_3$ppy)$_2$(pic)]), and bis[2-(4',6'-difluorophenyl)pyridinato-N,$C^{2'}$]iridium(III) acetylacetonate (abbreviation: FIr(acac)); and the like.

As a phosphorescent material that exhibits green or yellow and whose emission spectrum has a peak wavelength at greater than or equal to 495 nm and less than or equal to 590 nm, the following substances can be given.

The examples include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), (acetylacetonato)bis{4,6-dimethyl-2-[6-(2,6-dimethylphenyl)-4-pyrimidinyl-κ$N^3$]phenyl-κC}iridium(III) (abbreviation: [Ir(dmppm-dmp)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,$C^{2'}$)iridium(III) (abbreviation: [Ir(ppy)$_3$]), bis(2-phenylpyridinato-N,$C^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,$C^{2'}$)iridium(III) (abbreviation: [Ir(pq)$_3$]), bis(2-phenylquinolinato-N,$C^{2'}$)iridium(III) acetylacetonate (abbreviation: [Ir(pq)$_2$(acac)]), [2-(4-phenyl-2-pyridinyl-κN)phenyl-κC]bis[2-(2-pyridinyl-κN)phenyl-κC]iridium(III) (abbreviation: [Ir(ppy)$_2$(4dppy)]), and bis[2-(2-pyridinyl-κN)phenyl-κC][2-(4-methyl-5-phenyl-2-pyridinyl-κN)phenyl-κC]; organometallic complexes such as bis(2,4-diphenyl-1,3-oxazolato-N,C$^{2'}$)iridium(III) acetylacetonate (abbreviation: [Ir(dpo)$_2$(acac)]), bis{2-[4'-(perfluorophenyl)phenyl]pyridinato-N,C$^{2'}$}iridium(III) acetylacetonate (abbreviation: [Ir(p-PF-ph)$_2$(acac)]), and bis(2-phenylbenzothiazolato-N,C$^{2'}$)iridium(III) acetylacetonate (abbreviation: [Ir(bt)$_2$(acac)]); and rare earth metal complexes such as tris(acetylacetonato) (monophenanthroline) terbium(III) (abbreviation: [Tb(acac)$_3$(Phen)]).

As a phosphorescent material that exhibits yellow or red and whose emission spectrum has a peak wavelength at greater than or equal to 570 nm and less than or equal to 750 nm, the following substances can be given.

The examples include organometallic complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), bis[4,6-di(naphthalen-1-yl)pyrimidinato](dipivaloylmethanato)iridium(III) (abbreviation: [Ir(d1npm)$_2$(dpm)]), and tris(4-t-butyl-6-phenylpyrimidinato)iridium(III) (abbreviation: [Ir(tBuppm)$_3$]); organometallic complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), bis{4,6-dimethyl-2-[3-(3,5-dimethylphenyl)-5-phenyl-2-pyrazinyl-κN]phenyl-κC}(2,6-dimethyl-3,5-heptanedionato-κ$^2$O,O')iridium(III) (abbreviation: [Ir(dmdppr-P)$_2$(dibm)]), bis{4,6-dimethyl-2-[5-(4-cyano-2,6-dimethylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-dmCP)$_2$(dpm)]), (acetylacetonato)bis[2-methyl-3-phenylquinoxalinato-N,C$^{2'}$]iridium(III) (abbreviation: [Ir(mpq)$_2$(acac)]), (acetylacetonato)bis(2,3-diphenylquinoxalinato-N,C$^{2'}$)iridium(III) (abbreviation: [Ir(dpq)$_2$(acac)]), (acetylacetonato)bis[2,3-bis(4-fluorophenyl)quinoxalinato]iridium(III) (abbreviation: [Ir(Fdpq)$_2$(acac)]), and bis {4,6-dimethyl-2-[5-(5-cyano-2-methylphenyl)-3-(3,5-dimethylphenyl)-2-pyrazinyl-κN]phenyl-κC}(2,2,6,6-tetramethyl-3,5-heptanedionato-κ$^2$O,O')iridium(III) (abbreviation: [Ir(dmdppr-m5CP)$_2$(dpm)]); organometallic complexes having a pyridine skeleton, such as tris(1-phenylisoquinolinato-N,C$^{2'}$)iridium(III) (abbreviation: [Ir(piq)$_3$]), bis(1-phenylisoquinolinato-N,C$^{2'}$)iridium(III) acetylacetonate (abbreviation: [Ir(piq)$_2$(acac)]), and bis[4,6-dimethyl-2-(2-quinolinyl-κN)phenyl-κC](2,4-pentanedionato-κ$^2$O,O')iridium(III); platinum complexes such as 2,3,7,8,12,13,17,18-octaethyl-21H,23H-porphyrin-platinum(II) (abbreviation: [PtOEP]); and rare earth metal complexes such as tris(1,3-diphenyl-1,3-propanedionato) (monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]).

As the organic compounds (e.g., the host material and the assist material) used in the light-emitting layer 113, one or more kinds of substances having a larger energy gap than the light-emitting substance can be used.

In the case where the light-emitting substance used in the light-emitting layer 113 is a fluorescent material, an organic compound used in combination with the light-emitting substance is preferably an organic compound that has a high energy level in a singlet excited state and has a low energy level in a triplet excited state.

In terms of a preferable combination with the light-emitting substance (the fluorescent material or the phosphorescent material), specific examples of the organic compounds are shown below though some of them overlap the specific examples shown above.

In the case where the light-emitting substance is a fluorescent material, examples of the organic compound that can be used in combination with the light-emitting substance include fused polycyclic aromatic compounds, such as an anthracene derivative, a tetracene derivative, a phenanthrene derivative, a pyrene derivative, a chrysene derivative, and a dibenzo[g,p]chrysene derivative.

Specific examples of the organic compound (the host material) used in combination with the fluorescent material include 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), PCPN, 9,10-diphenylanthracene (abbreviation: DPAnth), N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), 4-(9H-carbazol-9-yl)-4'-(10-phenyl-9-anthryl)triphenylamine (abbreviation: YGAPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 6,12-dimethoxy-5,11-diphenylchrysene, N,N,N',N',N",N",N'",N'"-octaphenyldibenzo[g,p]chrysene-2,7,10,15-tetraamine (abbreviation: DBC1), CzPA, 7-[4-(10-phenyl-9-anthryl) phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)-biphenyl-4'-yl}anthracene (abbreviation: FLPPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl) diphenanthrene (abbreviation: DPNS), 9,9'-(stilbene-4,4'-diyl)diphenanthrene (abbreviation: DPNS2), 1,3,5-tri(1-pyrenyl)benzene (abbreviation: TPB3), 5,12-diphenyltetracene, and 5,12-bis(biphenyl-2-yl)tetracene.

In the case where the light-emitting substance is a phosphorescent material, as the organic compound used in combination with the light-emitting substance, an organic compound that has higher triplet excitation energy (energy difference between a ground state and a triplet excited state) than the light-emitting substance is selected.

In the case where a plurality of organic compounds (e.g., a first host material and a second host material (or an assist material)) are used in combination with the light-emitting substance in order to form an exciplex, the plurality of organic compounds are preferably mixed with a phosphorescent material (particularly an organometallic complex).

Such a structure makes it possible to efficiently obtain light emission utilizing ExTET (Exciplex-Triplet Energy Transfer), which is energy transfer from an exciplex to a light-emitting substance. Note that a combination of a plurality of organic compounds that easily forms an exciplex is preferable, and it is particularly preferable to combine a compound that easily accepts holes (a hole-transport material) and a compound that easily accepts electrons (an electron-transport material). Note that the organic compound of one embodiment of the present invention described in Embodiment 1 is preferably used as a compound that has a low LUMO level and easily accepts electrons. As the hole-transport material and the electron-transport material, specifically, any of the materials described in this embodiment can be used. With this structure, high efficiency, low voltage, and a long lifetime of the light-emitting device can be achieved at the same time.

In the case where the light-emitting substance is a phosphorescent material, examples of the organic compounds that can be used in combination with the light-emitting substance include an aromatic amine, a carbazole derivative, a dibenzothiophene derivative, a dibenzofuran derivative, a zinc- or aluminum-based metal complex, an oxadiazole derivative, a triazole derivative, a benzimidazole derivative, a quinoxaline derivative, a dibenzoquinoxaline derivative, a pyrimidine derivative, a triazine derivative, a pyridine derivative, a bipyridine derivative, and a phenanthroline derivative.

Among the above-described compounds, specific examples of the aromatic amine, (a compound having an aromatic amine skeleton), the carbazole derivative, the dibenzothiophene derivative (thiophene derivative), and the dibenzofuran derivative (furan derivative), which are organic compounds having a high hole-transport property, are the same as the compounds given above as specific examples of the hole-transport material.

Specific examples of the zinc- and aluminum-based metal complexes, which are organic compounds having a high electron-transport property, include metal complexes having a quinoline skeleton or a benzoquinoline skeleton, such as tris(8-quinolinolato)aluminum(III) (abbreviation: Alq), tris (4-methyl-8-quinolinolato)aluminum(III) (abbreviation: Almq$_3$), bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), and bis(8-quinolinolato)zinc(II) (abbreviation: Znq).

A metal complex having an oxazole-based or thiazole-based ligand such as bis[2-(2-benzoxazolyl)phenolato]zinc (II) (abbreviation: ZnPBO) or bis[2-(2-benzothiazolyl)phenolato]zinc(II) (abbreviation: ZnBTZ), or the like can also be used.

Specific examples of the oxadiazole derivative, the triazole derivative, the benzimidazole derivative, the benzimidazole derivative, the benzimidazole derivative, the quinoxaline derivative, the dibenzoquinoxaline derivative, and the phenanthroline derivative, which are organic compounds having a high electron-transport property, include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 3-(4-biphenylyl)-4-phenyl-5-(4-tert-butylphenyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), 2,2',2"-(1,3,5-benzenetriyl)tris(1-phenyl-1H-benzimidazole) (abbreviation: TPBI), 2-[3-(dibenzothiophen-4-yl)phenyl]-1-phenyl-1H-benzimidazole (abbreviation: mDBTBIm-II), 4,4'-bis(5-methylbenzoxazol-2-yl)stilbene (abbreviation: BzOs), bathophenanthroline (abbreviation: Bphen), bathocuproine (abbreviation: BCP), 2,9-bis(naphthalen-2-yl)-4,7-diphenyl-1,10-phenanthroline (abbreviation: NBphen), 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo [f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Specific examples of a heterocyclic compound having a diazine skeleton, a heterocyclic compound having a triazine skeleton, and a heterocyclic compound having a pyridine skeleton, which are organic compounds having a high electron-transport property, include 4,6-bis[3-(phenanthren-9-yl)phenyl]pyrimidine (abbreviation: 4,6mPnP2Pm), 4,6-bis [3-(4-dibenzothienyl)phenyl]pyrimidine (abbreviation: 4,6mDBTP2Pm-II), 4,6-bis[3-(9H-carbazol-9-yl)phenyl] pyrimidine (abbreviation: 4,6mCzP2Pm), 2-{4-[3-(N-phenyl-9H-carbazol-3-yl)-9H-carbazol-9-yl]phenyl}-4,6-diphenyl-1,3,5-triazine (abbreviation: PCCzPTzn), 9-[3-(4,6-diphenyl-1,3,5-triazin-2-yl)phenyl]-9'-phenyl-2,3'-bi-9H-carbazole (abbreviation: mPCCzPTzn-02), 3,5-bis[3-(9H-carbazol-9-yl)phenyl]pyridine (abbreviation: 35DCzPPy), and 1,3,5-tri[3-(3-pyridyl)phenyl]benzene (abbreviation: TmPyPB).

As the organic compound having a high electron-transport property, a high molecular compound such as poly(2,5-pyridinediyl)(abbreviation: PPy), poly[(9,9-dihexylfluorene-2,7-diyl)-co-(pyridine-3,5-diyl)]abbreviation: PF-Py), or poly[(9,9-dioctylfluorene-2,7-diyl)-co-(2,2'-bipyridine-6, 6'-diyl)]abbreviation: PF-BPy) can also be used.

The TADF material is a material that can up-convert a triplet excited state into a singlet excited state (reverse intersystem crossing) using a little thermal energy and efficiently exhibits light emission (fluorescence) from the singlet excited state. Thermally activated delayed fluorescence is efficiently obtained under the condition where the difference in energy between the triplet excited level and the singlet excited level is greater than or equal to 0 eV and less than or equal to 0.2 eV, preferably greater than or equal to 0 eV and less than or equal to 0.1 eV. Delayed fluorescence by the TADF material refers to light emission having a spectrum similar to that of normal fluorescence and an extremely long lifetime. The lifetime is $10^{-6}$ seconds or longer, preferably $10^{-3}$ seconds or longer.

Examples of the TADF material include fullerene, a derivative thereof, an acridine derivative such as proflavine, and eosin. Other examples include a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: SnF$_2$(Proto IX)), a mesoporphyrin-tin fluoride complex (abbreviation: SnF$_2$(Meso IX)), a hematoporphyrin-tin fluoride complex (abbreviation: SnF$_2$(Hemato IX)), a coproporphyrin tetramethyl ester-tin fluoride complex (abbreviation: SnF$_2$(Copro III-4Me)), an octaethylporphyrin-tin fluoride complex (abbreviation: SnF$_2$(OEP)), an etioporphyrin-tin fluoride complex (abbreviation: SnF$_2$(Etio I)), and an octaethylporphyrin-platinum chloride complex (abbreviation: PtCl$_2$OEP).

It is possible to use a heterocyclic compound having a π-electron-rich heteroaromatic ring and a π-electron deficient heteroaromatic ring, such as 2-(biphenyl-4-yl)-4,6-bis (12-phenylindolo[2,3-a]carbazol-11-yl)-1,3,5-triazine (abbreviation: PIC-TRZ), PCCzPTzn, 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl) phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-

10'-one (abbreviation: ACRSA). Note that a substance in which a π-electron-rich heteroaromatic ring is directly bonded to a π-electron deficient heteroaromatic ring is particularly preferable because both the donor property of the π-electron-rich heteroaromatic ring and the acceptor property of the π-electron deficient heteroaromatic ring are improved and the energy difference between the singlet excited state and the triplet excited state becomes small.

Note that the TADF material can also be used in combination with another organic compound. In particular, the TADF material can be used in combination with the host material, the hole-transport material, and the electron-transport material described above.

Furthermore, when used in combination with a low molecular material or a high molecular material, the above materials can be used to form the light-emitting layer 113. For the deposition, a known method (e.g., an evaporation method, a coating method, or a printing method) can be used as appropriate.

<Electron-Transport Layer>

The electron-transport layer 114 is a layer that transports electrons, which are injected from the second electrode 102 by the electron-injection layer 115, to the light-emitting layer 113. Note that the electron-transport layer 114 is a layer including an electron-transport material. As the electron-transport material used in the electron-transport layer 114, a substance having an electron mobility greater than or equal to $1\times10^{-6}$ cm$^2$/Vs is preferable. Note that other substances can also be used as long as they have a property of transporting more electrons than holes. The light-emitting device of one embodiment of the present invention preferably includes the organic compound of one embodiment of the present invention as an electron-transport material that is used for the electron-transport layer 114.

As the electron-transport material, it is possible to use a material having a high electron-transport property, such as a metal complex having a quinoline skeleton, a metal complex having a benzoquinoline skeleton, a metal complex having an oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative having a quinoline ligand a benzoquinoline derivative, a quinoxaline derivative, a dibenzoquinoxaline derivative, a pyridine derivative, a bipyridine derivative, a pyrimidine derivative, or a π-electron deficient heteroaromatic compound such as a nitrogen-containing heteroaromatic compound.

As specific examples of the electron-transport material, the above-described materials can be used.

<Electron-Injection Layer>

The electron-injection layer 115 is a layer that contains a material having a high electron-injection property. For the electron-injection layer 115, an alkali metal, an alkaline earth metal, or a compound thereof such as lithium fluoride (LiF), cesium fluoride (CsF), calcium fluoride (CaF$_2$), or lithium oxide (LiO$_x$) can be used. A rare earth metal compound like erbium fluoride (ErF$_3$) can also be used. In addition, an electride may be used for the electron-injection layer 115. An example of the electride is a substance in which electrons are added at high concentration to calcium oxide-aluminum oxide. Any of the above-described substances for forming the electron-transport layer 114 can also be used.

For the electron-injection layer 115, a composite material containing an electron-transport material and a donor material (an electron-donating material) may be used. Such a composite material is excellent in an electron-injection property and an electron-transport property because electrons are generated in the organic compound by the electron donor. The organic compound here is preferably a material excellent in transporting the generated electrons; specifically, for example, the above-described electron-transport materials used in the electron-transport layer 114 (e.g., a metal complex or a heteroaromatic compound) can be used. As the electron donor, a substance showing an electron-donating property with respect to an organic compound is used. Specifically, an alkali metal, an alkaline earth metal, and a rare earth metal are preferable, and lithium, cesium, magnesium, calcium, erbium, ytterbium, and the like are given. In addition, an alkali metal oxide and an alkaline earth metal oxide are preferable, and lithium oxide, calcium oxide, barium oxide, and the like are given. A Lewis base such as magnesium oxide can be used. An organic compound such as tetrathiafulvalene (abbreviation: TTF) can be used.

<Charge-Generation Layer>

In the light-emitting device illustrated in FIG. 1C, the charge-generation layer 104 has a function of injecting electrons into the EL layer 103a and injecting holes into the EL layer 103b when voltage is applied between the first electrode 101 (the anode) and the second electrode 102 (the cathode).

The charge-generation layer 104 may contain a hole-transport material and an acceptor material (an electron-accepting material) or may contain an electron-transport material and a donor material. Forming the charge-generation layer 104 with such a structure can suppress an increase in the driving voltage that would be caused by stacking EL layers.

As the hole-transport material, the acceptor material, the electron-transport material, and the donor material, the above-described materials can be used.

For fabrication of the light-emitting device in this embodiment, a vacuum process such as an evaporation method or a solution process such as a spin coating method or an ink-jet method can be used. In the case of using an evaporation method, a physical vapor deposition method (PVD method) such as a sputtering method, an ion plating method, an ion beam evaporation method, a molecular beam evaporation method, or a vacuum evaporation method, a chemical vapor deposition method (CVD method), or the like can be used. Specifically, the functional layers (the hole-injection layer, the hole-transport layer, the light-emitting layer, the electron-transport layer, and the electron-injection layer) included in the EL layer and the charge-generation layer can be formed by an evaporation method (e.g., a vacuum evaporation method), a coating method (e.g., a dip coating method, a die coating method, a bar coating method, a spin coating method, or a spray coating method), a printing method (e.g., an ink-jet method, screen printing (stencil), offset printing (planography), flexography (relief printing), gravure printing, or micro-contact printing), or the like.

Materials of the functional layers included in the EL layer 103 and the charge-generation layer are not limited to the above-described corresponding materials. For example, as the materials of the functional layers, a high molecular compound (e.g., an oligomer, a dendrimer, and a polymer), a middle molecular compound (a compound between a low molecular compound and a high molecular compound with a molecular weight of 400 to 4000), or an inorganic compound (e.g., a quantum dot material) may be used. As the quantum dot material, a colloidal quantum dot material, an alloyed quantum dot material, a core-shell quantum dot material, a core quantum dot material, or the like can be used.

This embodiment can be combined with the other embodiments as appropriate.

Embodiment 3

In this embodiment, a light-emitting apparatus of one embodiment of the present invention will be described with reference to FIG. 2 to FIG. 5.

Structure Example 1 of Light-Emitting Apparatus

Figure 2A:
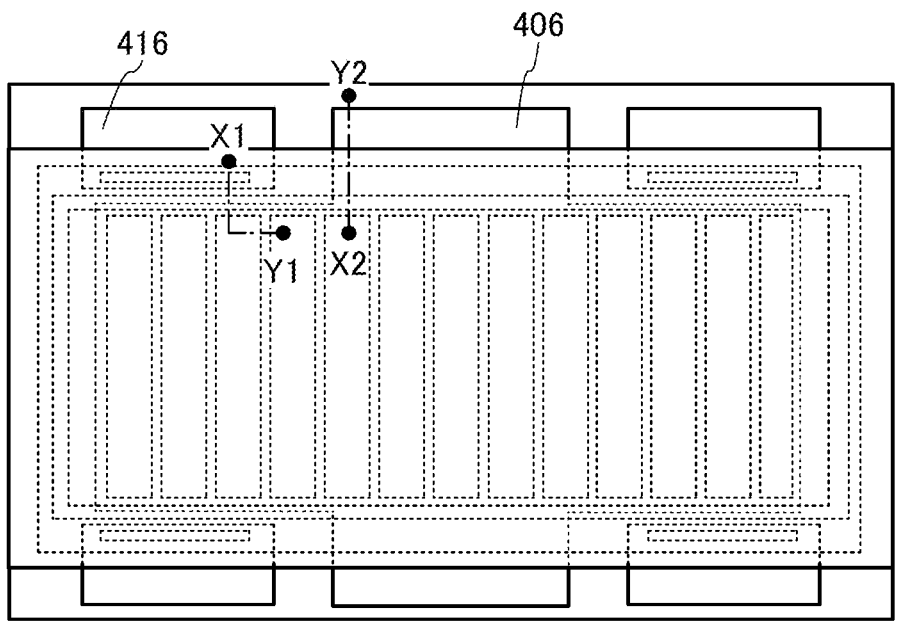
FIG. 2A is a top view illustrating an example of a light-emitting apparatus.
Figure 2B:
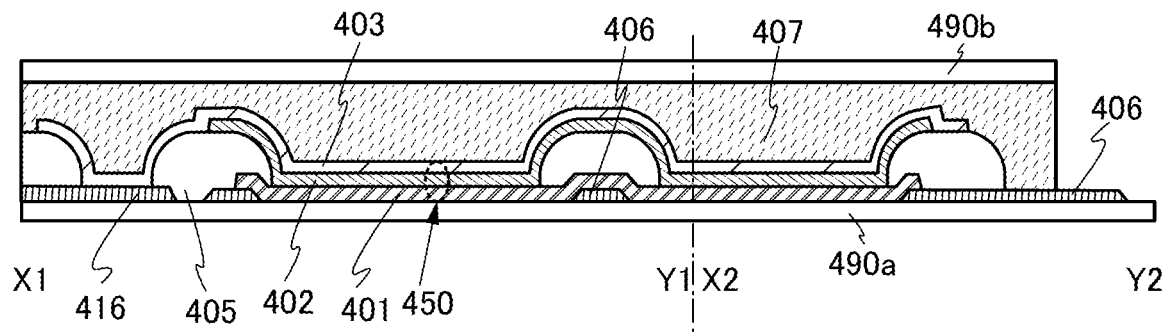
FIG. 2B and FIG. 2C are cross-sectional views illustrating examples of the light-emitting apparatus.
Figure 2C:
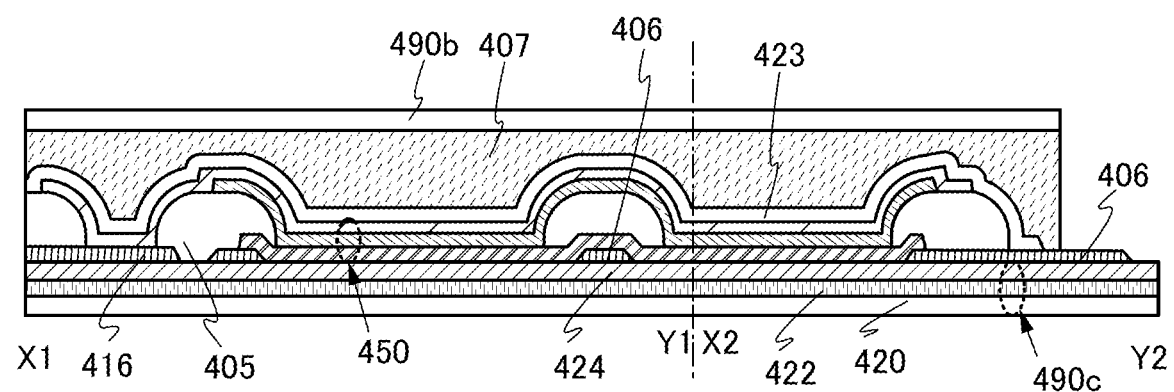

FIG. 2A is a top view of a light-emitting apparatus, and FIG. 2B and FIG. 2C are cross-sectional views along the dashed-dotted lines X1-Y1 and X2-Y2 in FIG. 2A. The light-emitting apparatus illustrated in FIG. 2A to FIG. 2C can be used as a lighting device, for example. The light-emitting apparatus can have a bottom-emission, top-emission, or dual-emission structure.

The light-emitting apparatus illustrated in FIG. 2B includes a substrate 490a, a substrate 490b, a conductive layer 406, a conductive layer 416, an insulating layer 405, an organic EL device 450 (a first electrode 401, an EL layer 402, and a second electrode 403), and an adhesive layer 407. The organic EL device 450 can also be referred to as a light-emitting element, an organic EL element, a light-emitting device, or the like. The EL layer 402 preferably includes the organic compound of one embodiment of the present invention described in Embodiment 1. For example, one or both of the host material of the light-emitting layer and the material of the electron-transport layer preferably include the organic compound.

The organic EL device 450 includes the first electrode 401 over the substrate 490a, the EL layer 402 over the first electrode 401, and the second electrode 403 over the EL layer 402. The organic EL device 450 is sealed by the substrate 490a, the adhesive layer 407, and the substrate 490b.

End portions of the first electrode 401, the conductive layer 406, and the conductive layer 416 are covered with the insulating layer 405. The conductive layer 406 is electrically connected to the first electrode 401, and the conductive layer 416 is electrically connected to the second electrode 403. The conductive layer 406 covered with the insulating layer 405 with the first electrode 401 positioned therebetween functions as an auxiliary wiring and is electrically connected to the first electrode 401. It is preferable that the auxiliary wiring electrically connected to the electrode of the organic EL device 450 be provided, in which case a voltage drop due to the resistance of the electrode can be inhibited. The conductive layer 406 may be provided over the first electrode 401. An auxiliary wiring that is electrically connected to the second electrode 403 may be provided, for example, over the insulating layer 405.

For each of the substrate 490a and the substrate 490b, glass, quartz, ceramic, sapphire, an organic resin, or the like can be used. When a flexible material is used for the substrate 490a and the substrate 490b, the flexibility of the display device can be increased.

A light-emitting surface of the light-emitting apparatus may be provided with a light extraction structure for increasing the light extraction efficiency, an antistatic film preventing the attachment of a foreign substance, a water repellent film suppressing the attachment of stain, a hard coat film suppressing generation of a scratch in use, an impact absorption layer, or the like.

Examples of an insulating material that can be used for the insulating layer 405 include a resin such as an acrylic resin and an epoxy resin, and an inorganic insulating material such as silicon oxide, silicon oxynitride, silicon nitride oxide, silicon nitride, and aluminum oxide.

For the adhesive layer 407, a variety of curable adhesives, e.g., a photocurable adhesive such as an ultraviolet curable adhesive, a reactive curable adhesive, a thermosetting adhesive, and an anaerobic adhesive can be used. Examples of these adhesives include an epoxy resin, an acrylic resin, a silicone resin, a phenol resin, a polyimide resin, an imide resin, a PVC (polyvinyl chloride) resin, a PVB (polyvinyl butyral) resin, and an EVA (ethylene vinyl acetate) resin. In particular, a material with low moisture permeability, such as an epoxy resin, is preferred. A two-component resin may be used. An adhesive sheet or the like may be used.

The light-emitting apparatus illustrated in FIG. 2C includes a barrier layer 490c, the conductive layer 406, the conductive layer 416, the insulating layer 405, the organic EL device 450, the adhesive layer 407, a barrier layer 423, and the substrate 490b.

The barrier layer 490c illustrated in FIG. 2C includes a substrate 420, an adhesive layer 422, and an insulating layer 424 having a high barrier property.

In the light-emitting apparatus illustrated in FIG. 2C, the organic EL device 450 is provided between the insulating layer 424 having a high barrier property and the barrier layer 423. Thus, even when resin films with relatively low water resistance or the like are used as the substrate 420 and the substrate 490b, a reduction in lifetime due to entry of impurities such as water into the organic EL device can be suppressed.

For each of the substrate 420 and the substrate 490b, for example, a polyester resin such as polyethylene terephthalate (PET) or polyethylene naphthalate (PEN), a polyacrylonitrile resin, an acrylic resin, a polyimide resin, a polymethyl methacrylate resin, a polycarbonate (PC) resin, a polyethersulfone (PES) resin, a polyamide resin (e.g., nylon or aramid), a polysiloxane resin, a cycloolefin resin, a polystyrene resin, a polyamide-imide resin, a polyurethane resin, a polyvinyl chloride resin, a polyvinylidene chloride resin, a polypropylene resin, a polytetrafluoroethylene (PTFE) resin, an ABS resin, cellulose nanofiber, or the like can be used. Glass that is thin enough to have flexibility may be used for the substrate 420 and the substrate 490b.

An inorganic insulating film is preferably used as the insulating layer 424 having a high barrier property. As the inorganic insulating film, a silicon nitride film, a silicon oxynitride film, a silicon oxide film, a silicon nitride oxide film, an aluminum oxide film, or an aluminum nitride film can be used, for example. A hafnium oxide film, an yttrium oxide film, a zirconium oxide film, a gallium oxide film, a tantalum oxide film, a magnesium oxide film, a lanthanum oxide film, a cerium oxide film, a neodymium oxide film, or the like may also be used. A stack including two or more of the above insulating films may also be used.

The barrier layer 423 preferably includes at least a single-layer inorganic film. For example, the barrier layer 423 can have a single-layer structure of an inorganic film or a stacked-layer structure of an inorganic film and an organic film. As the inorganic film, the above-described inorganic insulating film is preferable. An example of the stacked-layer structure is a structure in which a silicon oxynitride film, a silicon oxide film, an organic film, a silicon oxide film, and a silicon nitride film are formed in this order. When the protective layer has a stacked-layer structure of an inorganic film and an organic film, entry of impurities that can enter the organic EL device 450 (typically, hydrogen, water, and the like) can be suitably suppressed.

The insulating layer 424 having a high barrier property and the organic EL device 450 can be directly formed on the substrate 420 having flexibility. In that case, the adhesive layer 422 is not necessary. The insulating layer 424 and the organic EL device 450 can be formed over a rigid substrate with a separation layer provided therebetween and then transferred to the substrate 420. For example, the insulating layer 424 and the organic EL device 450 may be transferred to the substrate 420 in the following manner: the insulating layer 424 and the organic EL device 450 are separated from the rigid substrate by applying heat, force, laser light, or the like to the separation layer, and then the insulating layer 424 and the organic EL device 450 are bonded to the substrate 420 with the use of the adhesive layer 422. For the separation layer, a stacked-layer structure of inorganic films including a tungsten film and a silicon oxide film, or an organic resin film of polyimide or the like can be used, for example. In the case where a rigid substrate is used, the insulating layer 424 can be formed at high temperature as compared to the case where a resin substrate or the like is used; thus, the insulating layer 424 can have high density and an excellent barrier property.

Structure Example 2 of Light-Emitting Apparatus

Figure 3A:
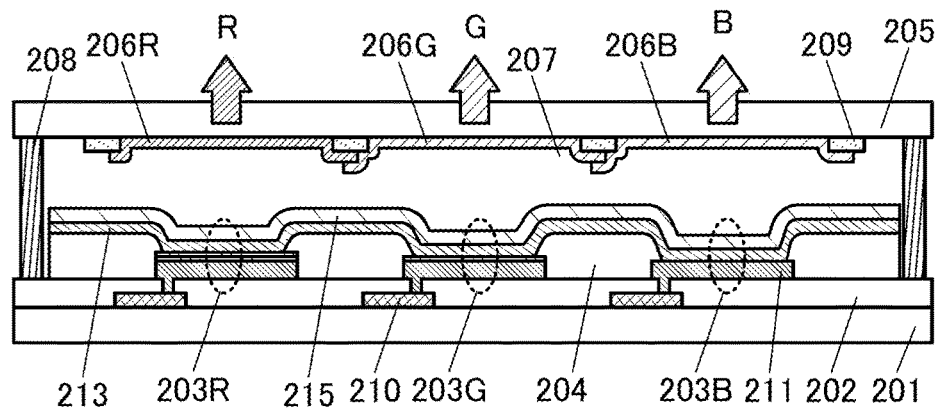
FIG. 3A and FIG. 3C are cross-sectional views illustrating examples of light-emitting apparatuses.

FIG. 3A is a top view of the light-emitting apparatus. The light-emitting apparatus illustrated in FIG. 3A is an active-matrix light-emitting apparatus in which a transistor is electrically connected to a light-emitting device.

The light-emitting apparatus illustrated in FIG. 3A includes a substrate 201, a transistor 210, a light-emitting device 203R, a light-emitting device 203G, a light-emitting device 203B, a color filter 206R, a color filter 206G, a color filter 206B, a substrate 205, and the like.

In FIG. 3A, the transistor 210 is provided over the substrate 201, the insulating layer 202 is provided over the transistor 210, and the light-emitting devices 203R, 203G, and 203B are provided over the insulating layer 202.

The transistor 210 and the light-emitting devices 203R, 203G, and 203B are sealed in a space 207 surrounded by the substrate 201, the substrate 205, and the adhesive layer 208. The space 207 can be filled with, for example, a reduced-pressure atmosphere, an inert atmosphere, or a resin.

In the light-emitting apparatus illustrated in FIG. 3A, one pixel includes a red subpixel (R), a green subpixel (G), and a blue subpixel (B).

The light-emitting apparatus of one embodiment of the present invention includes a plurality of pixels arranged in a matrix. One pixel includes one or more subpixels. One subpixel includes one light-emitting device. For example, the pixel can have a structure including three subpixels (e.g., three colors of R, G, and B or three colors of yellow (Y), cyan (C), and magenta (M)) or four subpixels (e.g., four colors of R, G, B, and white (W) or four colors of R, G, B, and Y).

Figure 3B:
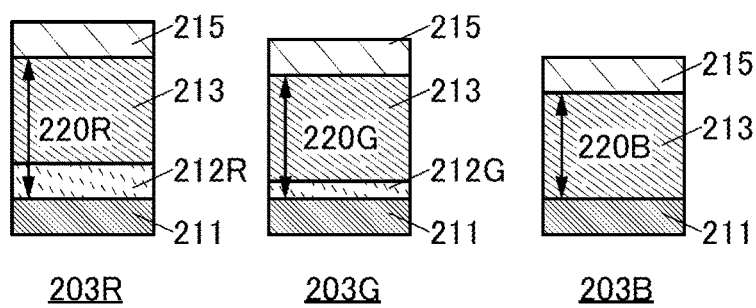
FIG. 3B is a cross-sectional view illustrating an example of a light-emitting device.

FIG. 3B illustrates detailed structures of the light-emitting device 203R, the light-emitting device 203G, and the light-emitting device 203B. The light-emitting devices 203R, 203G, and 203B include the EL layer 213 in common, and have microcavity structures in which the optical path length between electrodes of each light-emitting device is adjusted in accordance with the emission color of the light-emitting device. The EL layer 213 preferably includes the organic compound of one embodiment of the present invention described in Embodiment 1. For example, one or both of the host material of the light-emitting layer and the material of the electron-transport layer preferably include the organic compound.

The first electrode 211 functions as a reflective electrode and the second electrode 215 functions as a transflective electrode.

In the light-emitting device 203R, the optical path length between the first electrode 211 and the second electrode 215 is adjusted to be an optical path length 220R in order to enhance the intensity of red light. Similarly, in the light-emitting device 203G, the optical path length between the first electrode 211 and the second electrode 215 is adjusted to be an optical path length 220G in order to enhance the intensity of green light. In the light-emitting device 203B, the optical path length between the first electrode 211 and the second electrode 215 is adjusted to be an optical path length 220B in order to enhance the intensity of blue light.

Optical adjustment can be performed in such a manner that a conductive layer 212R is formed over the first electrode 211 in the light-emitting device 203R and a conductive layer 212G is formed over the first electrode 211 in the light-emitting device 203G as illustrated in FIG. 3B. Furthermore, in the light-emitting device 203B, the optical path length 220B may be adjusted by forming a conductive layer whose thickness is different from those of the conductive layer 212R and the conductive layer 212G over the first electrode 211. Note that as illustrated in FIG. 3A, end portions of the first electrode 211, the conductive layer 212R, and the conductive layer 212G are covered with an insulating layer 204.

The light-emitting apparatus illustrated in FIG. 3A is a top-emission light-emitting apparatus, which emits light obtained from the light-emitting devices through color filters formed on the substrate 205. The color filter can transmit visible light in a specific wavelength range and block visible light in a specific wavelength range.

In the red subpixel (R), light from the light-emitting device 203R is emitted through the red color filter 206R. As illustrated in FIG. 3A, the color filter 206R that transmits only light in the red wavelength range is provided in a position overlapping with the light-emitting device 203R, whereby red light emission can be obtained from the light-emitting device 203R.

Similarly, in the green subpixel (G), light from the light-emitting device 203G is emitted through the green color filter 206G, and in the blue subpixel (B), light from the light-emitting device 203B is emitted through the blue color filter 206B.

Note that a black matrix 209 (also referred to as a black layer) may be provided at an end portion of one type of color filter. Furthermore, the color filters for the respective colors and the black matrix 209 may be covered with an overcoat layer that transmits visible light.

Figure 3C:
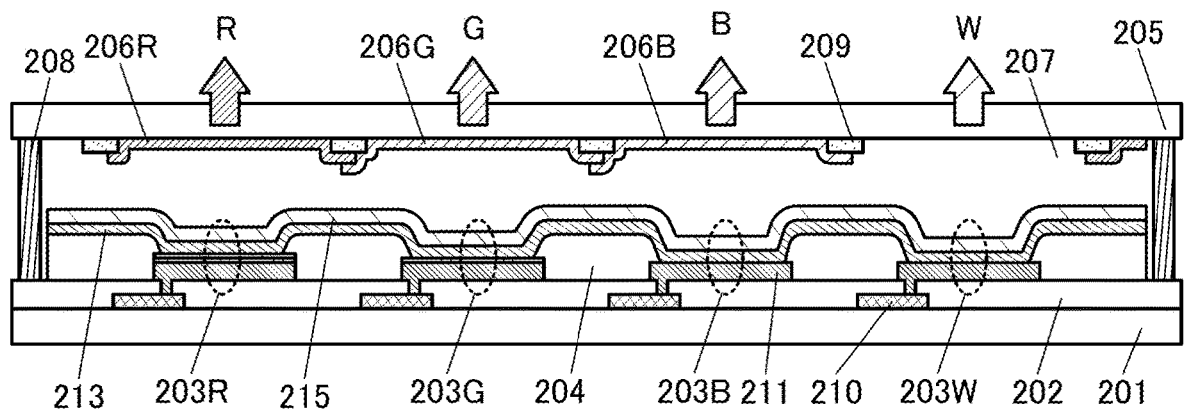

In the light-emitting apparatus illustrated in FIG. 3C, one pixel includes the red subpixel (R), the green subpixel (G), the blue subpixel (B), and a white subpixel (W). In FIG. 3C, light from a light-emitting device 203W included in the white subpixel (W) is emitted to the outside of the light-emitting apparatus without passing through a color filter.

Note that the optical path length between the first electrode 211 and the second electrode 215 in the light-emitting device 203W may be the same as the optical path length in any one of the light-emitting devices 203R, 203G, and 203B or may be different from the optical path lengths in the light-emitting devices 203R, 203G, and 203B.

In the case where the intensity of light with a blue wavelength is desired to be enhanced, for example, in the case where light emitted from the light-emitting device 203W is white light with a low color temperature, the optical path length in the light-emitting device 203W is preferably equal to the optical path length 220B in the light-emitting device 203B, as illustrated in FIG. 3C. Thus, light obtained from the light-emitting device 203W can be made closer to white light with a desired color temperature.

Figure 4A:
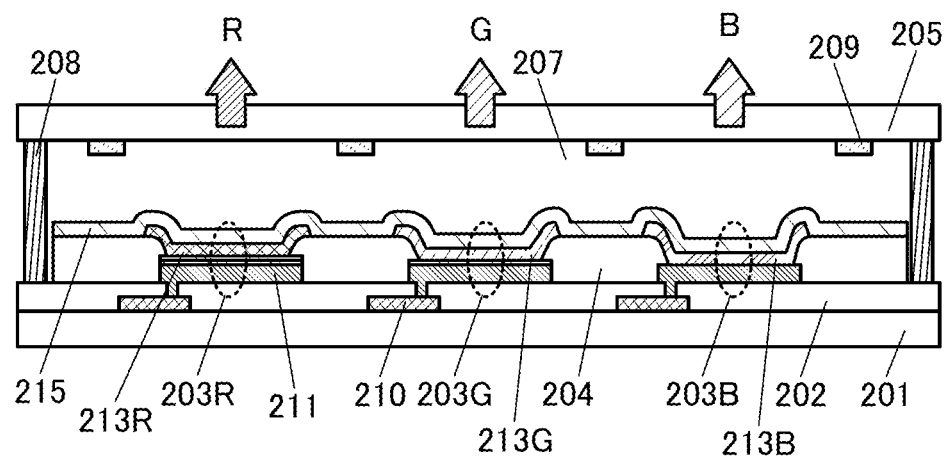
FIG. 4A and FIG. 4B are cross-sectional views illustrating examples of light-emitting apparatuses.

Although FIG. 3A illustrates an example in which the light-emitting devices in the subpixels use the EL layer 213 in common, different EL layers may be used for the light-emitting devices in the subpixels as illustrated in FIG. 4A. The above-described microcavity structure can also be applied to FIG. 4A.

FIG. 4A illustrates an example in which the light-emitting device 203R includes an EL layer 213R, the light-emitting device 203G includes an EL layer 213G, and the light-emitting device 203B includes an EL layer 213B. The EL layers 213R, 213G, and 213B may include a common layer. For example, the EL layers 213R, 213G, and 213B may include light-emitting layers with different structures and a common layer as another layer. In FIG. 4A, light emitted from the light-emitting devices 203R, 203G, and 203B may be emitted through a color filter or without passing through a color filter.

Figure 4B:
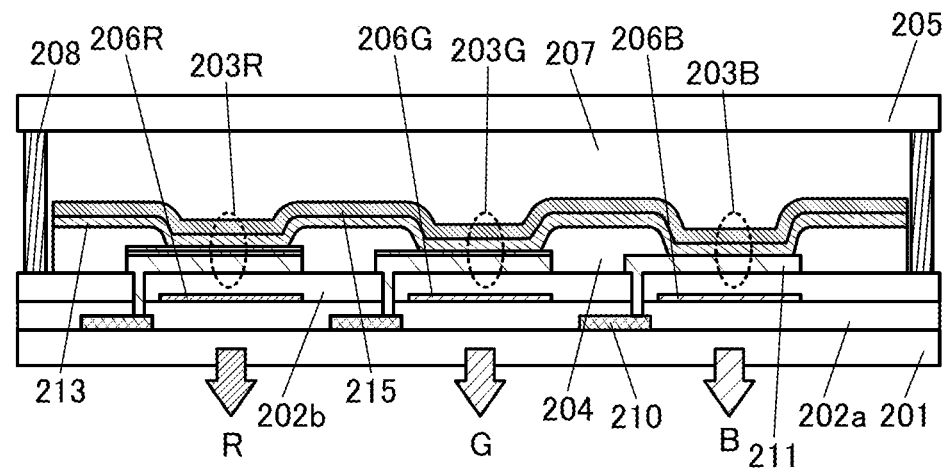

Although FIG. 3A illustrates the top-emission light-emitting apparatus, a light-emitting apparatus with a (bottom emission) structure in which light is extracted to the substrate 201 side where the transistor 210 is formed as illustrated in FIG. 4B is also one embodiment of the present invention.

In the bottom-emission light-emitting apparatus, color filters for the respective colors are preferably provided between the substrate 201 and the light-emitting devices. FIG. 4B illustrates an example in which the transistor 210 is formed over the substrate 201, an insulating layer 202a is formed over the transistor 210, the color filters 206R, 206G, and 206B are formed over the insulating layer 202a, an insulating layer 202b is formed over the color filters 206R, 206G, and 206B, and the light-emitting devices 203R, 203G, and 203B are formed over the insulating layer 202b.

In the case of the top-emission light-emitting apparatus, a light-blocking substrate or a light-transmitting substrate can be used as the substrate 201, and a light-transmitting substrate can be used as the substrate 205.

In the case of the bottom-emission light-emitting apparatus, a light-blocking substrate or a light-transmitting substrate can be used as the substrate 205, and a light-transmitting substrate can be used as the substrate 201.

Structure Example 3 of Light-Emitting Apparatus

The light-emitting apparatus of one embodiment of the present invention can be of passive matrix type or active matrix type. An active-matrix light-emitting apparatus will be described with reference to FIG. 5.

Figure 5A:
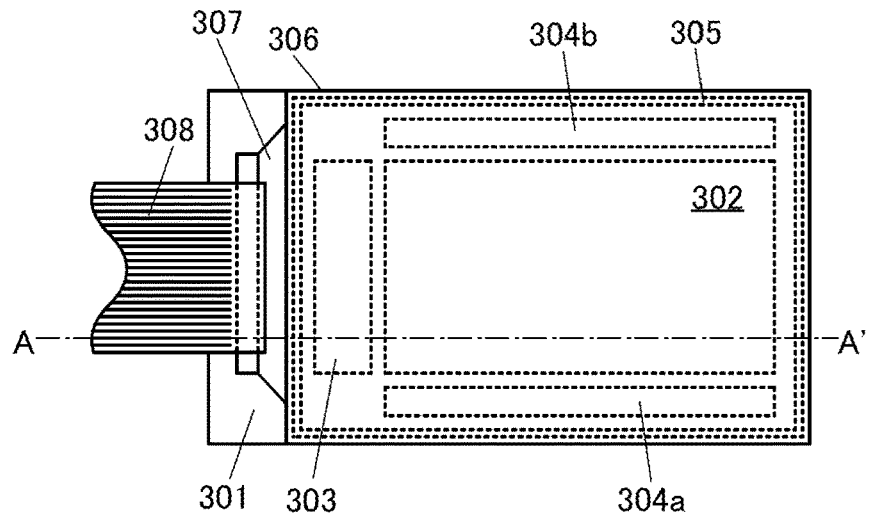
FIG. 5A is a top view illustrating an example of a light-emitting apparatus.
Figure 5B:
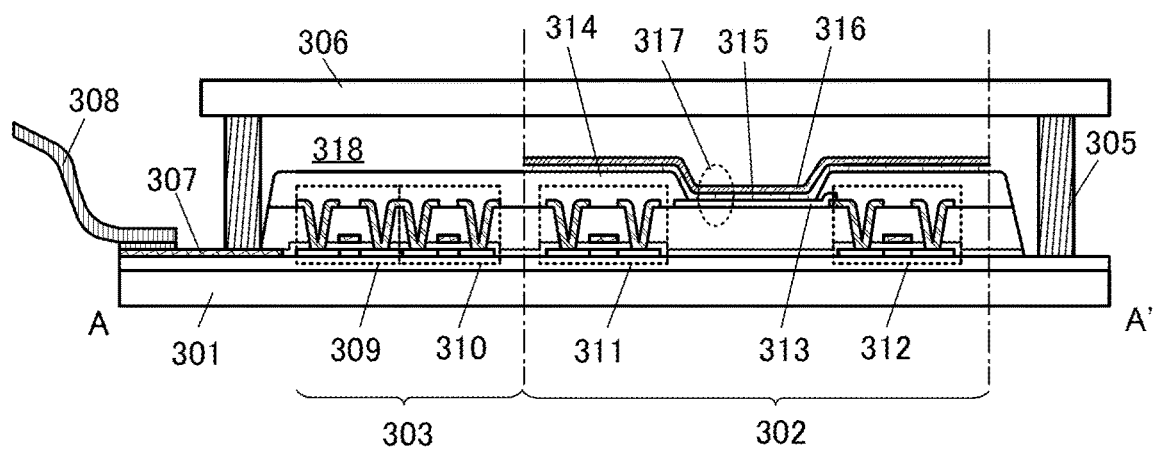
FIG. 5B is a cross-sectional view illustrating an example of a light-emitting apparatus.

FIG. 5A is a top view of the light-emitting apparatus. FIG. 5B is a cross-sectional view along the dashed-dotted line A-A' in FIG. 5A.

The active-matrix light-emitting apparatus illustrated in FIG. 5A and FIG. 5B includes a pixel portion 302, a circuit portion 303, a circuit portion 304a, and a circuit portion 304b.

Each of the circuit portion 303, the circuit portion 304a, and the circuit portion 304b can function as a scan line driver circuit (a gate driver) or a signal line driver circuit (a source driver), or may be a circuit that electrically connects the pixel portion 302 to an external gate driver or source driver.

A lead wiring 307 is provided over a first substrate 301. The lead wiring 307 is electrically connected to an FPC 308 that is an external input terminal. The FPC 308 transmits signals (e.g., a video signal, a clock signal, a start signal, and a reset signal) and a potential from the outside to the circuit portion 303, the circuit portion 304a, and the circuit portion 304b. The FPC 308 may be provided with a printed wiring board (PWB). The structure illustrated in FIG. 5A and FIG. 5B can also be referred to as a light-emitting module including a light-emitting device (or a light-emitting apparatus) and an FPC.

The pixel portion 302 includes a plurality of pixels each including an organic EL device 317, a transistor 311, and a transistor 312. The transistor 312 is electrically connected to a first electrode 313 included in the organic EL device 317. The transistor 311 functions as a switching transistor. The transistor 312 functions as a current control transistor. Note that the number of transistors included in each pixel is not particularly limited and can be set appropriately as needed.

The circuit portion 303 includes a plurality of transistors, such as a transistor 309 and a transistor 310. The circuit portion 303 may be configured with a circuit including transistors having the same conductivity type (either n-channel transistors or p-channel transistors), or may be configured with a CMOS circuit including an n-channel transistor and a p-channel transistor. Furthermore, a driver circuit may be provided outside.

There is no particular limitation on the structure of the transistor included in the light-emitting apparatus of this embodiment. For example, a planar transistor, a staggered transistor, or an inverted staggered transistor can be used. A top-gate or a bottom-gate transistor structure may be used; or gates may be provided above and below a semiconductor layer where a channel is formed.

There is no particular limitation on the crystallinity of a semiconductor material used for the transistor, and an amorphous semiconductor or a semiconductor having crystallinity (a microcrystalline semiconductor, a polycrystalline semiconductor, a single crystal semiconductor, or a semiconductor partly including crystal regions) can be used. A semiconductor having crystallinity is preferably used, in which case deterioration of the transistor characteristics can be suppressed.

It is preferable that the semiconductor layer of the transistor contain a metal oxide (also referred to as an oxide semiconductor); or the semiconductor layer of the transistor may contain silicon. Examples of silicon include amorphous silicon and crystalline silicon (e.g., low-temperature polysilicon and single crystal silicon).

The semiconductor layer preferably contains indium, M (M is one or more kinds selected from gallium, aluminum, silicon, boron, yttrium, tin, copper, vanadium, beryllium, titanium, iron, nickel, germanium, zirconium, molybdenum, lanthanum, cerium, neodymium, hafnium, tantalum, tungsten, and magnesium), and zinc, for example. Specifically, M is preferably one or more kinds selected from aluminum, gallium, yttrium, and tin.

It is particularly preferable to use an oxide containing indium (In), gallium (Ga), and zinc (Zn) (also referred to as IGZO) for the semiconductor layer.

In the case where the semiconductor layer is an In—M—Zn oxide, a sputtering target used for depositing the In—

M—Zn oxide preferably has the atomic proportion of In higher than or equal to the atomic proportion of M. Examples of the atomic ratio of the metal elements in such a sputtering target include In:M:Zn=1:1:1, In:M:Zn=1:1:1.2, In:M:Zn=2:1:3, In:M:Zn=3:1:2, In:M:Zn=4:2:3, In:M:Zn=4:2:4.1, In:M:Zn=5:1:6, In:M:Zn=5:1:7, In:M:Zn=5:1:8, In:M:Zn=6:1:6, and In:M:Zn=5:2:5.

The transistors included in the circuit portion 303, the circuit portion 304a, and the circuit portion 304b and the transistors included in the pixel portion 302 may have the same structure or different structures. A plurality of transistors included in the circuit portion 303, the circuit portion 304a, and the circuit portion 304b may have the same structure or two or more kinds of structures. Similarly, a plurality of transistors included in the pixel portion 302 may have the same structure or two or more kinds of structures.

An end portion of the first electrode 313 is covered with an insulating layer 314. For the insulating layer 314, an organic compound such as a negative photosensitive resin or a positive photosensitive resin (acrylic resin), or an inorganic compound such as silicon oxide, silicon oxynitride, or silicon nitride can be used. An upper end portion or a lower end portion of the insulating layer 314 preferably has a curved surface with curvature. In that case, favorable coverage with a film formed over the insulating layer 314 can be obtained.

An EL layer 315 is provided over the first electrode 313, and a second electrode 316 is provided over the EL layer 315. The EL layer 315 includes a light-emitting layer, a hole-injection layer, a hole-transport layer, an electron-transport layer, an electron-injection layer, a charge-generation layer, and the like. The EL layer 315 preferably includes the organic compound of one embodiment of the present invention described in Embodiment 1. For example, one or both of the host material of the light-emitting layer and the material of the electron-transport layer preferably include the organic compound.

The plurality of transistors and the plurality of organic EL devices 317 are sealed by the first substrate 301, a second substrate 306, and a sealant 305. A space 318 surrounded by the first substrate 301, the second substrate 306, and the sealant 305 may be filled with an inert gas (e.g., nitrogen or argon) or an organic substance (including the sealant 305).

An epoxy resin or glass frit can be used for the sealant 305. A material that transmits moisture and oxygen as little as possible is preferably used for the sealant 305. In the case where glass frit is used for the sealant, the first substrate 301 and the second substrate 306 are preferably glass substrates in terms of adhesion.

Figure 5C:
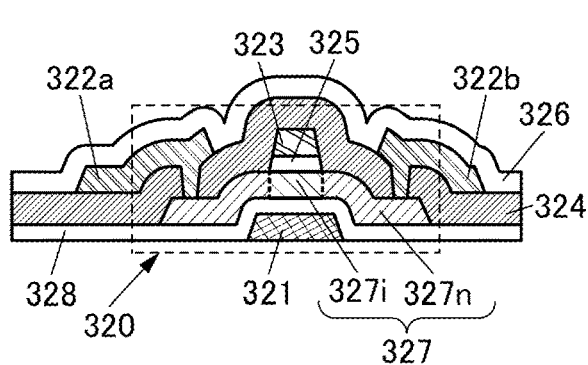
FIG. 5C and FIG. 5D are cross-sectional views illustrating examples of transistors.
Figure 5D:
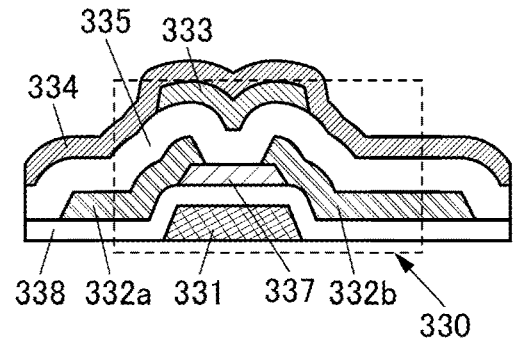

FIG. 5C and FIG. 5D illustrate examples of transistors that can be used in a light-emitting apparatus.

A transistor 320 illustrated in FIG. 5C includes a conductive layer 321 functioning as a gate, an insulating layer 328 functioning as a gate insulating layer, a semiconductor layer 327 including a channel formation region 327i and a pair of low-resistance regions 327n, a conductive layer 322a connected to one of the pair of low-resistance regions 327n, a conductive layer 322b connected to the other of the pair of low-resistance regions 327n, an insulating layer 325 functioning as a gate insulating layer, a conductive layer 323 functioning as a gate, and an insulating layer 324 covering the conductive layer 323. The insulating layer 328 is positioned between the conductive layer 321 and the channel formation region 327i. The insulating layer 325 is positioned between the conductive layer 323 and the channel formation region 327i. The transistor 320 is preferably covered with an insulating layer 326. The insulating layer 326 may be included as a component in the transistor 320.

The conductive layer 322a and the conductive layer 322b are each connected to the low-resistance region 327n through openings in the insulating layer 324. One of the conductive layer 322a and the conductive layer 322b functions as a source and the other functions as a drain.

The insulating layer 325 is provided to overlap with at least the channel formation region 327i of the semiconductor layer. The insulating layer 325 may cover top surfaces and side surfaces of the pair of low-resistance regions 327n.

A transistor 330 illustrated in FIG. 5D includes a conductive layer 331 functioning as a gate, an insulating layer 338 functioning as a gate insulating layer, a conductive layer 332a and a conductive layer 332b which function as a source and a drain, a semiconductor layer 337, an insulating layer 335 functioning as a gate insulating layer, and a conductive layer 333 functioning as a gate. The insulating layer 338 is positioned between the conductive layer 331 and the semiconductor layer 337. The insulating layer 335 is positioned between the conductive layer 333 and the semiconductor layer 337. The transistor 330 is preferably covered with an insulating layer 334. The insulating layer 334 may be included as a component in the transistor 330.

The structure in which the semiconductor layer where a channel is formed is provided between two gates is used for the transistor 320 and the transistor 330. The two gates may be connected to each other and supplied with the same signal to drive the transistor; or a potential for adjusting the threshold voltage may be supplied to one of the two gates and a potential for driving may be supplied to the other to adjust the threshold voltage of the transistor.

A material through which impurities such as water and hydrogen do not easily diffuse is preferably used for at least one of the insulating layers that cover the transistors. Thus, such an insulating layer can function as a barrier layer. Such a structure can effectively inhibit diffusion of impurities into the transistors from the outside and increase the reliability of the light-emitting apparatus.

An inorganic insulating film is preferably used as the insulating layer 325, the insulating layer 326, the insulating layer 328, the insulating layer 334, the insulating layer 335, and the insulating layer 338. As the inorganic insulating film, a silicon nitride film, a silicon oxynitride film, a silicon oxide film, a silicon nitride oxide film, an aluminum oxide film, or an aluminum nitride film can be used, for example. A hafnium oxide film, an yttrium oxide film, a zirconium oxide film, a gallium oxide film, a tantalum oxide film, a magnesium oxide film, a lanthanum oxide film, a cerium oxide film, a neodymium oxide film, or the like may also be used. A stack including two or more of the above insulating films may also be used.

Note that as materials that can be used for the conductive layers included in the light-emitting apparatus, metals such as aluminum, titanium, chromium, nickel, copper, yttrium, zirconium, molybdenum, silver, tantalum, and tungsten, alloys containing these metals as its main component, and the like can be given. A single layer or stacked-layer structure including a film including these materials can be used. For example, a single-layer structure of an aluminum film containing silicon, a two-layer structure in which an aluminum film is stacked over a titanium film, a two-layer structure in which an aluminum film is stacked over a tungsten film, a two-layer structure in which a copper film is stacked over a copper-magnesium-aluminum alloy film, a two-layer structure in which a copper film is stacked over a titanium film, a two-layer structure in which a copper film is stacked over a tungsten film, a three-layer structure in which an aluminum film or a copper film is stacked over a titanium film or a titanium nitride film and a titanium film or a titanium nitride film is formed thereover, a three-layer structure in which an aluminum film or a copper film is stacked over a molybdenum film or a molybdenum nitride film and a molybdenum film or a molybdenum nitride film is formed thereover, and the like can be given. Note that an oxide such as indium oxide, tin oxide, or zinc oxide may be used. Copper containing manganese is preferably used because it increases controllability of a shape by etching.

This embodiment can be combined with the other embodiments as appropriate.

Embodiment 4

In this embodiment, electronic devices of one embodiment of the present invention will be described with reference to drawings.

Examples of electronic devices include a television set, a monitor of a computer or the like, a digital camera, a digital video camera, a digital photo frame, a mobile phone (also referred to as a cellular phone or a mobile phone device), a portable game machine, a portable information terminal, an audio reproducing device, a large game machine such as a pinball machine, a biometric authentication device, and a testing device.

The electronic devices of one embodiment of the present invention include the light-emitting apparatus of one embodiment of the present invention in its display portion and thus has high emission efficiency and high reliability.

The display portion of the electronic device in this embodiment can display a video with a resolution of, for example, full high definition, 4K2K, 8K4K, 16K8K, or higher. As a screen size of the display portion, the diagonal size can be greater than or equal to 20 inches, greater than or equal to 30 inches, greater than or equal to 50 inches, greater than or equal to 60 inches, or greater than or equal to 70 inches.

The electronic device of one embodiment of the present invention has flexibility and therefore can be incorporated along a curved surface of an inside or outside wall of a house or a building or a curved surface of an interior or an exterior of an automobile.

The electronic device of one embodiment of the present invention may include a secondary battery. It is preferable that the secondary battery be capable of being charged by contactless power transmission.

Examples of the secondary battery include a lithium ion secondary battery such as a lithium polymer battery using a gel electrolyte (a lithium ion polymer battery), a nickel-hydride battery, a nickel-cadmium battery, an organic radical battery, a lead-acid battery, an air secondary battery, a nickel-zinc battery, and a silver-zinc battery.

The electronic device of one embodiment of the present invention may include an antenna. When a signal is received by the antenna, the electronic device can display a video, information, or the like on a display portion. When the electronic device includes the antenna and a secondary battery, the antenna may be used for contactless power transmission.

The electronic device of this embodiment may include a sensor (a sensor having a function of measuring force, displacement, position, speed, acceleration, angular velocity, rotational frequency, distance, light, liquid, magnetism, temperature, a chemical substance, sound, time, hardness, electric field, current, voltage, electric power, radiation, flow rate, humidity, gradient, oscillation, a smell, or infrared rays).

The electronic device of this embodiment can have a variety of functions. For example, the electronic device can have a function of displaying a variety of kinds of information (a still image, a moving image, a text image, and the like) on the display portion, a touch panel function, a function of displaying a calendar, date, time, and the like, a function of executing a variety of software (programs), a wireless communication function, and a function of reading out a program or data stored in a recording medium.

Figure 6A:
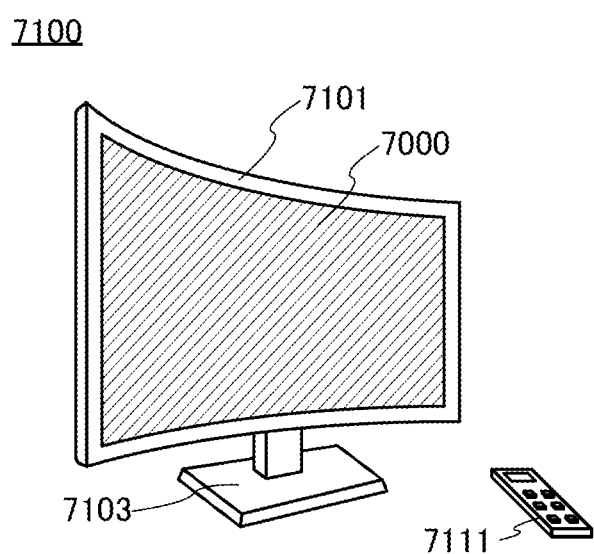
FIG. 6A, FIG. 6B, FIG. 6C, and FIG. 6D are diagrams illustrating examples of electronic devices.

FIG. 6A shows an example of a television device. In a television device 7100, a display portion 7000 is incorporated in a housing 7101. Here, a structure in which the housing 7101 is supported by a stand 7103 is illustrated.

The light-emitting apparatus of one embodiment of the present invention can be used for the display portion 7000.

The television device 7100 illustrated in FIG. 6A can be operated with an operation switch provided in the housing 7101 or a separate remote controller 7111; or the display portion 7000 may include a touch sensor, and the television device 7100 can be operated by touching the display portion 7000 with a finger or the like. The remote controller 7111 may include a display portion for displaying information output from the remote controller 7111. With a touch panel or operation keys provided in the remote controller 7111, channels and volume can be controlled, and videos displayed on the display portion 7000 can be controlled.

Note that the television device 7100 is provided with a receiver, a modem, and the like. A general television broadcast can be received with the receiver. When the television device is connected to a communication network with or without wires via the modem, one-way (from a transmitter to a receiver) or two-way (between a transmitter and a receiver or between receivers, for example) information communication can be performed.

Figure 6B:
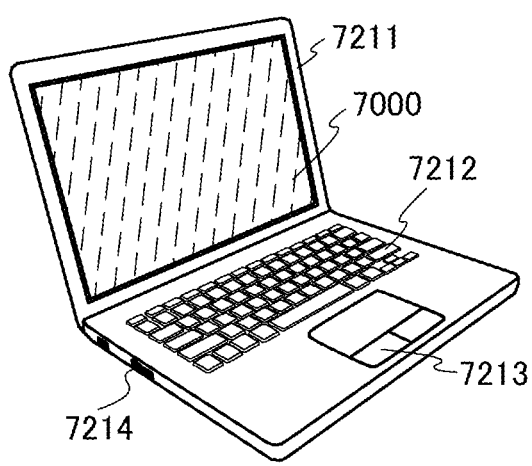

FIG. 6B shows an example of a laptop personal computer. A laptop personal computer 7200 includes a housing 7211, a keyboard 7212, a pointing device 7213, an external connection port 7214, and the like. The display portion 7000 is incorporated in the housing 7211.

The light-emitting apparatus of one embodiment of the present invention can be used for the display portion 7000.

Figure 6C:
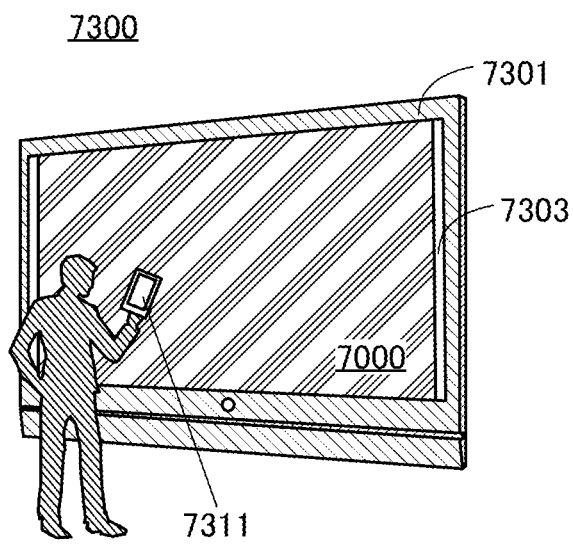
Figure 6D:
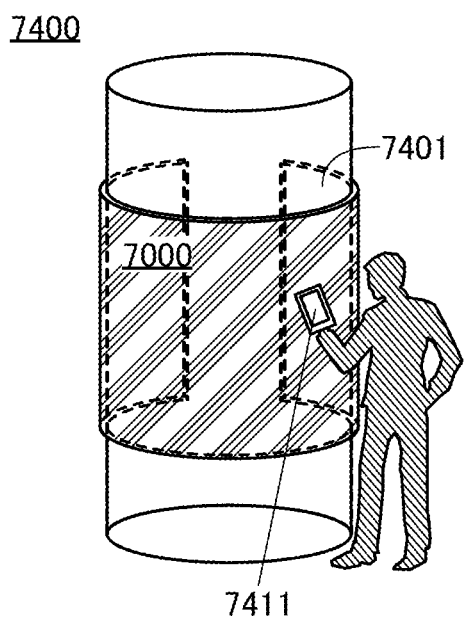

FIG. 6C and FIG. 6D show examples of digital signage.

Digital signage 7300 illustrated in FIG. 6C includes a housing 7301, the display portion 7000, a speaker 7303, and the like. Furthermore, an LED lamp, operation keys (including a power switch or an operation switch), a connection terminal, a variety of sensors, a microphone, and the like can be included.

FIG. 6D illustrates digital signage 7400 mounted on a cylindrical pillar 7401. The digital signage 7400 includes the display portion 7000 provided along a curved surface of the pillar 7401.

The light-emitting apparatus of one embodiment of the present invention can be used for the display portion 7000 in FIG. 6C and FIG. 6D.

A larger area of the display portion 7000 can increase the amount of information that can be provided at a time. The larger display portion 7000 attracts more attention, so that the effectiveness of the advertisement can be increased, for example.

The use of a touch panel in the display portion 7000 is preferable because in addition to display of a still image or a moving image on the display portion 7000, intuitive operation by a user is possible. For an application for providing information such as route information or traffic information, usability can be enhanced by intuitive operation.

As illustrated in FIG. 6C and FIG. 6D, it is preferable that the digital signage 7300 or the digital signage 7400 be capable of working with an information terminal 7311 or an information terminal 7411 such as a smartphone a user has through wireless communication. For example, information of an advertisement displayed on the display portion 7000 can be displayed on a screen of the information terminal 7311 or the information terminal 7411. By operation of the information terminal 7311 or the information terminal 7411, display on the display portion 7000 can be switched.

It is possible to make the digital signage 7300 or the digital signage 7400 execute a game with the use of the screen of the information terminal 7311 or the information terminal 7411 as an operation means (controller). Thus, an unspecified number of users can join in and enjoy the game concurrently.

FIG. 7A to FIG. 7F show examples of a portable information terminal including a flexible display portion 7001.

The display portion 7001 is manufactured using the light-emitting apparatus of one embodiment of the present invention. For example, a light-emitting apparatus that can be bent with a radius of curvature greater than or equal to 0.01 mm and less than or equal to 150 mm can be used. The display portion 7001 may include a touch sensor so that the portable information terminal can be operated by touching the display portion 7001 with a finger or the like.

Figure 7A:
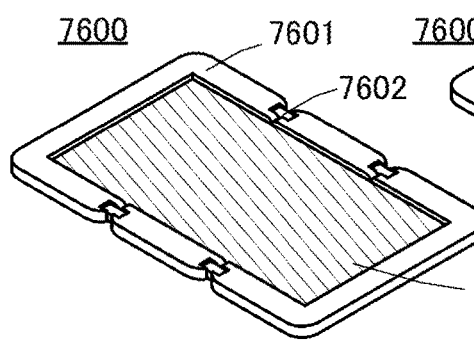
FIG. 7A, FIG. 7B, FIG. 7C, FIG. 7D, FIG. 7E, and FIG. 7F are diagrams illustrating examples of electronic devices.
Figure 7B:
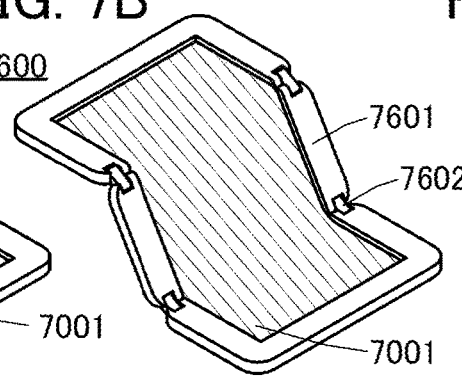
Figure 7C:
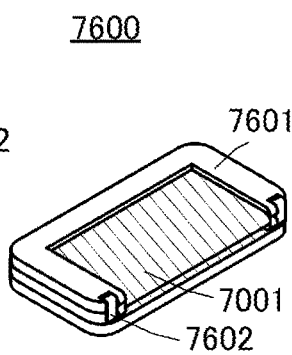

FIG. 7A to FIG. 7C show an example of a foldable portable information terminal. FIG. 7A illustrates an opened state, FIG. 7B illustrates a state in the middle of change from one of an opened state and a folded state to the other, and FIG. 7C illustrates a folded state of a portable information terminal 7600. The portable information terminal 7600 has excellent portability when in a folded state. The portable information terminal 7600 has excellent browsability when in an opened state because of its seamless large display region.

The display portion 7001 is supported by three housings 7601 joined together by hinges 7602. By folding a space between two housings 7601 with the hinges 7602, the portable information terminal 7600 can be reversibly changed in shape from an opened state to a folded state.

Figure 7D:
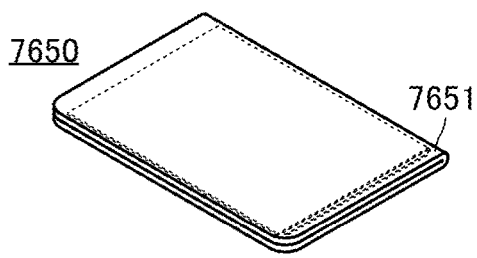
Figure 7E:
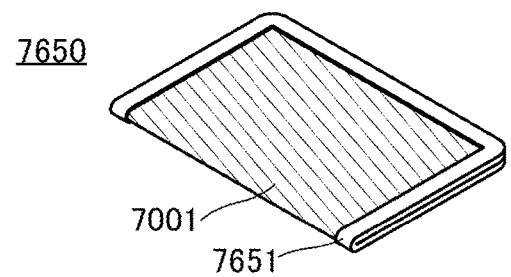

FIG. 7D and FIG. 7E show an example of a foldable portable information terminal. FIG. 7D illustrates a portable information terminal 7650 that is folded so that the display portion 7001 is on the inside; FIG. 7E illustrates the portable information terminal 7650 that is folded so that the display portion 7001 is on the outside. The portable information terminal 7650 includes the display portion 7001 and a non-display portion 7651. Contamination of or damage to the display portion 7001 can be suppressed by folding the portable information terminal 7650 to place the display portion 7001 on the inside when the portable information terminal 7650 is not used.

Figure 7F:
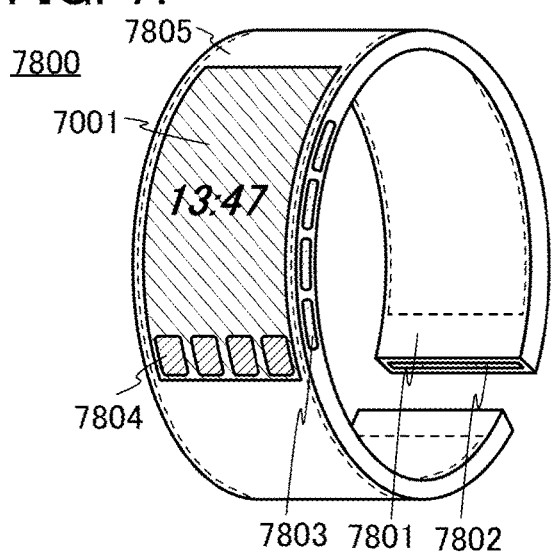

FIG. 7F shows an example of a wrist-watch-type portable information terminal. A portable information terminal 7800 includes a band 7801, the display portion 7001, an input-output terminal 7802, operation buttons 7803, and the like. The band 7801 has a function of a housing. A flexible battery 7805 can be mounted on the portable information terminal 7800. The battery 7805 may be placed to overlap with the display portion 7001 or the band 7801, for example.

The band 7801, the display portion 7001, and the battery 7805 have flexibility. Thus, the portable information terminal 7800 can be easily curved to have a desired shape.

The operation button 7803 can give a variety of functions such as time setting, on/off of the power, on/off of wireless communication, setting and cancellation of silent mode, and setting and cancellation of power saving mode. For example, the functions of the operation button 7803 can be set freely by the operating system incorporated in the portable information terminal 7800.

By touching an icon 7804 displayed on the display portion 7001 with a finger or the like, application can be started.

The portable information terminal 7800 can execute near field communication conformable to a communication standard. For example, mutual communication between the portable information terminal and a headset capable of wireless communication can be performed, and thus hands-free calling is possible.

The portable information terminal 7800 may include the input-output terminal 7802. In the case where the input-output terminal 7802 is included, data can be directly transmitted to and received from another information terminal via a connector. Charging through the input-output terminal 7802 is also possible. Note that charging of the portable information terminal described as an example in this embodiment can be performed by non-contact power transmission without using the input-output terminal.

Figure 8A:
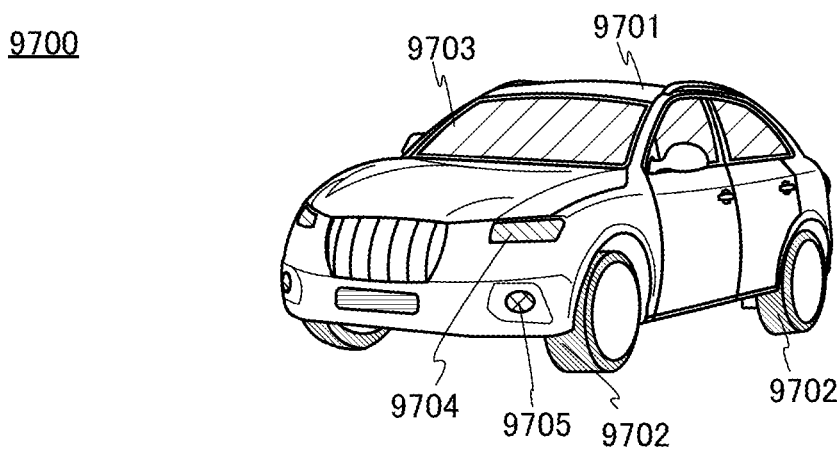
FIG. 8A is a diagram illustrating the appearance of an automobile.
Figure 8B:
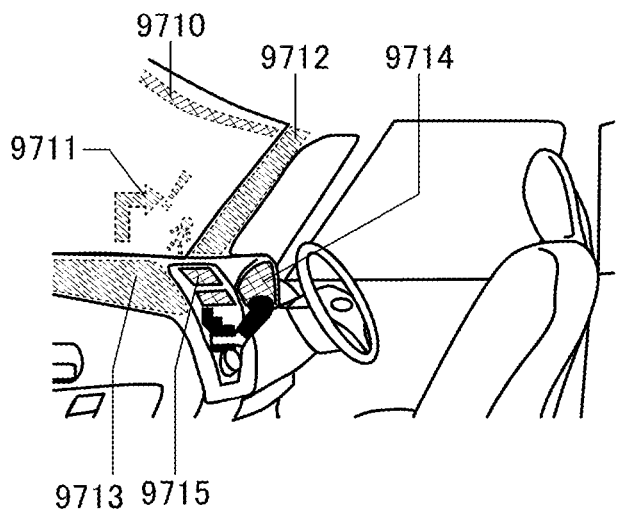
FIG. 8B and FIG. 8C are diagrams illustrating the interior of an automobile.

FIG. 8A is an external view of an automobile 9700. FIG. 8B illustrates a driver's seat of the automobile 9700. The automobile 9700 includes a car body 9701, wheels 9702, a windshield 9703, lights 9704, fog lamps 9705, and the like. The light-emitting apparatus of one embodiment of the present invention can be used in a display portion of the automobile 9700, for example.

For example, the light-emitting apparatus of one embodiment of the present invention can be provided for a display portion 9710 to a display portion 9715 illustrated in FIG. 8B; or the light-emitting apparatus of one embodiment of the present invention may be used in the lights 9704 or the fog lamps 9705.

The display portion 9710 and the display portion 9711 are display devices provided in an automobile windshield. The light-emitting apparatus of one embodiment of the present invention can be a see-through device, through which the opposite side can be seen, by using a light-transmitting conductive material for forming its electrodes and wirings. Such a display portion 9710 or 9711 in a see-through state does not hinder driver's vision during driving of the automobile 9700. Therefore, the light-emitting apparatus of one embodiment of the present invention can be provided in the windshield of the automobile 9700. In the case where a transistor for driving the light-emitting apparatus is provided, a transistor having a light-transmitting property, such as an organic transistor using an organic semiconductor material or a transistor using an oxide semiconductor, is preferably used.

The display portion 9712 is a display device provided on a pillar portion. For example, the display portion 9712 can compensate for the view hindered by the pillar by displaying an image taken by an imaging means provided on the car body. The display portion 9713 is a display device provided on a dashboard. For example, the display portion 9713 can compensate for the view hindered by the dashboard by displaying an image taken by an imaging means provided on the car body. That is, by displaying an image taken by an imaging means provided on the outside of the automobile, blind areas can be eliminated and safety can be increased. Display of an image that complements the area that cannot be seen makes it possible to confirm safety more naturally and comfortably.

Figure 8C:
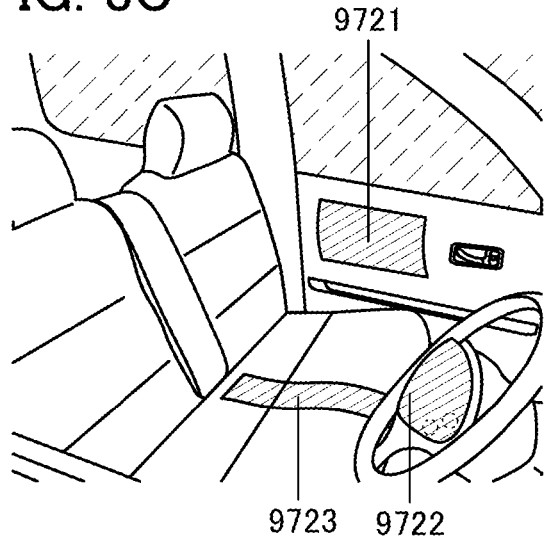

FIG. 8C illustrates the inside of a car in which a bench seat is used as a driver seat and a front passenger seat. A display portion 9721 is a display device provided in a door portion. For example, the display portion 9721 can compensate for the view hindered by the door by displaying an image taken by an imaging means provided in the car body. A display portion 9722 is a display device provided in a steering wheel. A display portion 9723 is a display device provided in the middle of a seating face of the bench seat. Provided on the seating surface, backrest, or the like, the display device can be used as a seat heater with heat generation of the display device as a heat source.

The display portion 9714, the display portion 9715, and the display portion 9722 can provide a variety of kinds of information by displaying navigation data, a speedometer, a tachometer, a mileage, a fuel meter, a gearshift indicator, air-condition setting, and the like. The content, layout, or the like of the display on the display portions can be changed freely by a user as appropriate. The above information can also be displayed on the display portion 9710 to the display portion 9713, the display portion 9721, and the display portion 9723. The display portion 9710 to the display portion 9715 and the display portion 9721 to the display portion 9723 can also be used as lighting devices. The display portion 9710 to the display portion 9715 and the display portion 9721 to the display portion 9723 can also be used as heating devices.

The electronic devices of one embodiment of the present invention include the light-emitting apparatus of one embodiment of the present invention in its light source and thus has high emission efficiency and high reliability. For example, the light-emitting apparatus of one embodiment of the present invention can be used for a light source that emits visible light or near-infrared light. The light-emitting apparatus of one embodiment of the present invention can also be used as a light source of a lighting device.

Figure 9A:
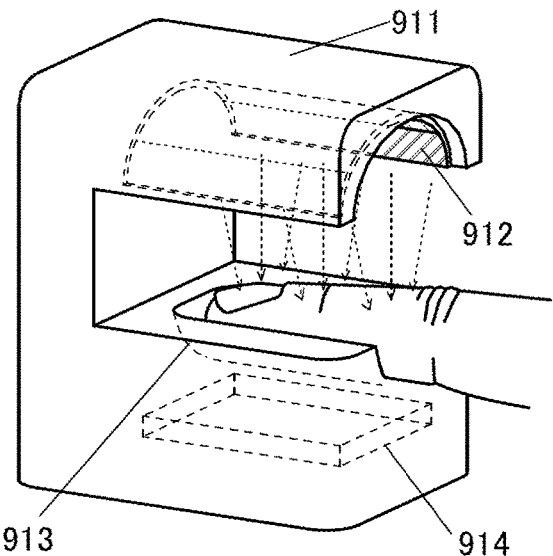
FIG. 9A and FIG. 9C are diagrams illustrating examples of biometric authentication apparatuses.

FIG. 9A illustrates a biometric authentication apparatus for sensing a finger vein which includes a housing 911, a light source 912, a sensing stage 913, and the like. By putting a finger on the sensing stage 913, an image of a vein pattern can be captured. The light source 912 that emits near-infrared light is provided above the sensing stage 913, and an imaging device 914 is provided under the sensing stage 913. The sensing stage 913 is formed of a material that transmits near-infrared light, and near-infrared light that is emitted from the light source 912 and passes through the finger can be captured by the imaging device 914. Note that an optical system may be provided between the sensing stage 913 and the imaging device 914. The structure of the apparatus described above can also be applied to a biometric authentication apparatus for sensing a palm vein.

The light-emitting apparatus of one embodiment of the present invention can be used for the light source 912. The light-emitting apparatus of one embodiment of the present invention can be provided to be curved and can emit light uniformly toward a target. In particular, the light-emitting apparatus preferably emits near-infrared light with the maximum peak intensity at a wavelength from 700 nm to 1200 nm. An image is formed from received light that has passed through the finger, palm, or the like, whereby the position of the vein can be detected. This action can be utilized for biometric identification. When combined with the global shutter system, highly accurate sensing becomes possible even while an object is moving.

Figure 9B:
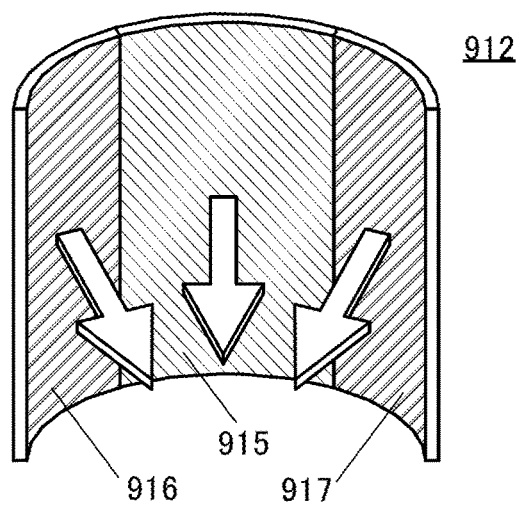
FIG. 9B is a diagram illustrating an example of a light source.

The light source 912 can include a plurality of light-emitting portions, such as light-emitting portions 915, 916, and 917 illustrated in FIG. 9B. The light-emitting portions 915, 916, and 917 may emit different wavelength light, and can emit light at different timings. Thus, by changing wavelengths and angles of light to be delivered, different images can be taken successively; hence, high level of security can be achieved using a plurality of images for the authentication.

Figure 9C:
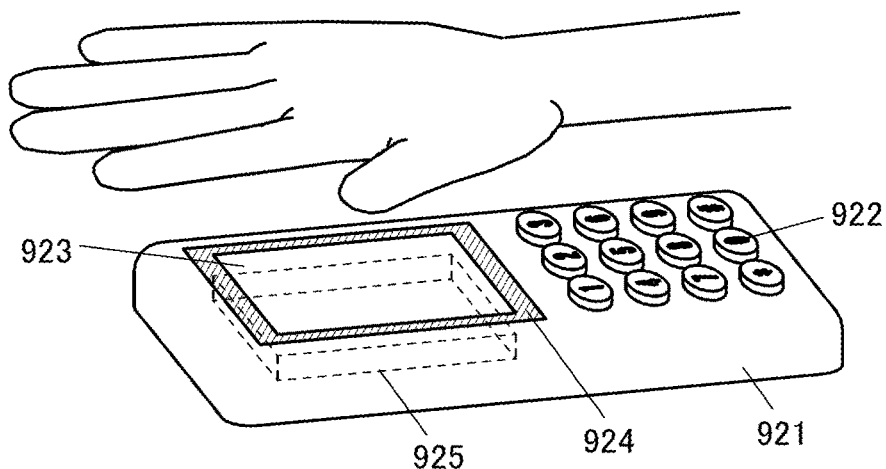

FIG. 9C illustrates a biometric authentication apparatus for sensing a palm vein which includes a housing 921, operation buttons 922, a sensing portion 923, a light source 924 that emits near-infrared light, and the like. By holding a hand over the sensing portion 923, a palm vein pattern can be recognized. A security code or the like can be input with the operation buttons. The light source 924 is provided around the sensing portion 923 and irradiates a target (a hand) with light. Then, light reflected by the target enters the sensing portion 923. The light-emitting apparatus of one embodiment of the present invention can be used for the light source 924. An imaging device 925 is provided directly under the sensing portion 923 and can capture an image of the target (an image of the whole hand). Note that an optical system may be provided between the sensing portion 923 and the imaging device 925. The structure of the apparatus described above can also be applied to a biometric authentication apparatus for sensing a finger vein.

Figure 9D:
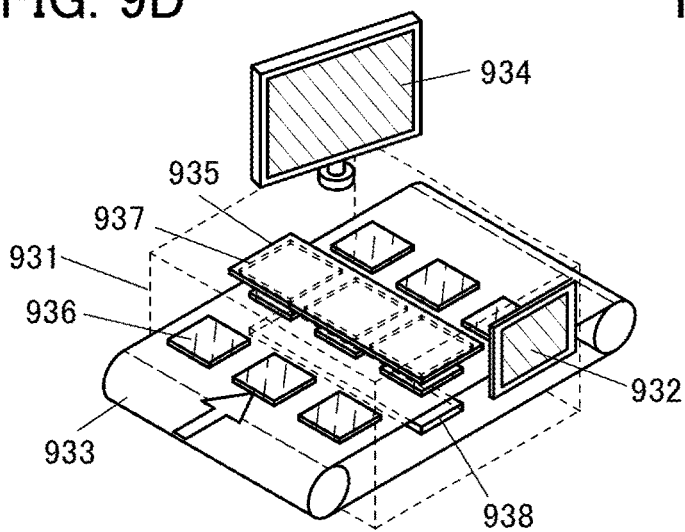
FIG. 9D is a diagram illustrating an example of a non-destructive testing apparatus.

FIG. 9D illustrates a non-destructive testing apparatus that includes a housing 931, an operation panel 932, a transport mechanism 933, a monitor 934, a sensing unit 935, a light source 938 that emits near-infrared light, and the like. The light-emitting apparatus of one embodiment of the present invention can be used for the light source 938. Test specimens 936 are transported by the transport mechanism 933 to be located directly beneath the sensing unit 935. The test specimen 936 is irradiated with near-infrared light from the light source 938, and the light passing therethrough is captured by an imaging device 937 provided in the sensing unit 935. The captured image is displayed on the monitor 934. After that, the test specimens 936 are transported to the exit of the housing 931, and defective pieces are sorted and collected. Imaging with the use of near-infrared light enables non-destructive and high-speed sensing of defective elements inside a non-test specimen, such as defects and foreign substances.

Figure 9E:
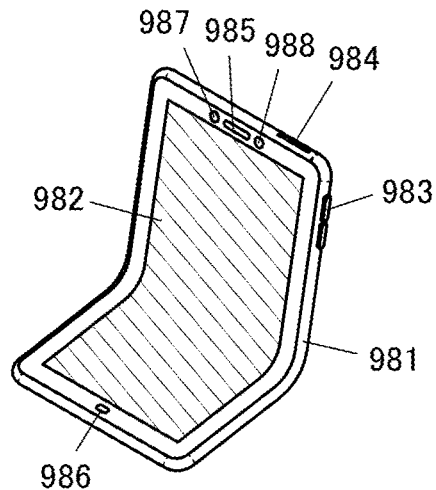
FIG. 9E is a diagram illustrating an example of a mobile phone.

FIG. 9E illustrates a mobile phone that includes a housing 981, a display portion 982, an operation button 983, an external connection port 984, a speaker 985, a microphone 986, a first camera 987, a second camera 988, and the like. The display portion 982 of the mobile phone includes a touch sensor. The housing 981 and the display portion 982 have flexibility. All operations including making a call and inputting text can be performed by touch on the display portion 982 with a finger, a stylus, or the like. The first camera 987 can take a visible light image, and the second camera 988 can take an infrared light image (a near-infrared light image). The mobile phone or the display portion 982 illustrated in FIG. 9E may include the light-emitting apparatus of one embodiment of the present invention.

This embodiment can be combined with the other embodiments as appropriate.

Example 1

Synthesis Example 1

In this example, a method of synthesizing an organic compound of one embodiment of the present invention will be described. In this example, the description is made on a method of synthesizing 10-[(3'-dibenzothiophen-4-yl)biphenyl-3-yl]naphtho[1',2':4,5]furo[2,3-b]quinoxaline (abbreviation: 10mDBtBPNfqn), which is represented by Structural Formula (100) in Embodiment 1.

[Chemical Formula 28]

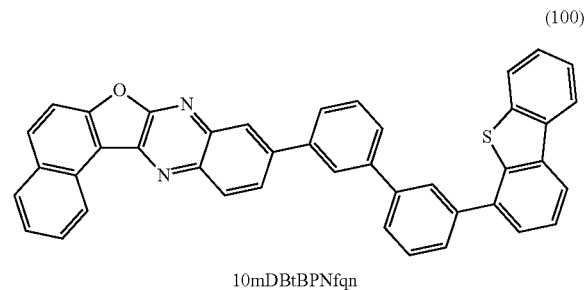

10mDBtBPNfqn

<Step 1; Synthesis of 7-chloro-3-(2-methoxynaphthalen-1-yl)quinoxalin-2-amine>

First, into a three-neck flask equipped with a reflux pipe were put 2.49 g of 3,7-dichloroquinoxalin-2-amine, 2.38 g of 2-methoxynaphthalen-1-boronic acid, 3.90 g of cesium carbonate, 46 mL of 1,4-dioxane, and 23 mL of water, and the air in the flask was replaced with nitrogen. After the mixture in the flask was degassed by being stirred under reduced pressure, 1.38 g of tetrakis(triphenylphosphine)palladium(0) (abbreviation: Pd(PPh$_3$)$_4$) was added, and stirring was performed at 80° C. for 6 hours for reaction.

The solution after the reaction was subjected to extraction process with dichloromethane to give a residue. After that, the obtained residue was purified by silica gel column chromatography using a developing solvent in which dichloromethane:ethyl acetate=50:1, whereby the quinoxaline derivative that was the object was obtained (a yellow solid, yield: 2.89 g, 70%). The synthesis scheme of Step 1 is shown in (a-1).

[Chemical Formula 29]

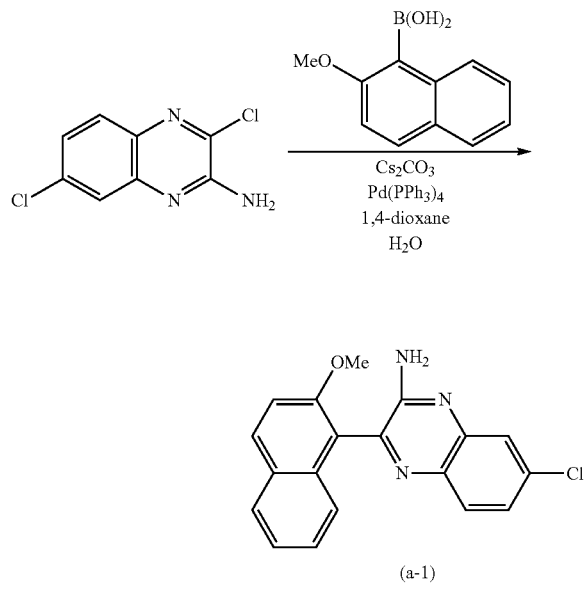

<Step 2; Synthesis of 10-chloro-naphtho[1',2':4,5]furo[2,3-b]quinoxaline>

Next, into a three-neck flask were put 2.89 g of 7-chloro-3-(2-methoxynaphthalen-1-yl)quinoxalin-2-amine obtained in Step 1, 90 mL of dehydrated tetrahydrofuran, and 90 mL of a glacial acetic acid, and the air in the flask was replaced with nitrogen. After the flask was cooled down to −10° C., 3.0 mL of tert-butyl nitrite was dripped, and stirring was performed at −10° C. for 18 hours and at 0° C. for 1 hour. After a predetermined time elapsed, 400 mL of water was added to the obtained suspension and suction filtration was performed, whereby the quinoxaline derivative that was the object was obtained (a yellowish white solid, 1.63 g, in a yield of 64%).

The synthesis scheme of Step 2 is shown in (a-2).

[Chemical Formula 30]

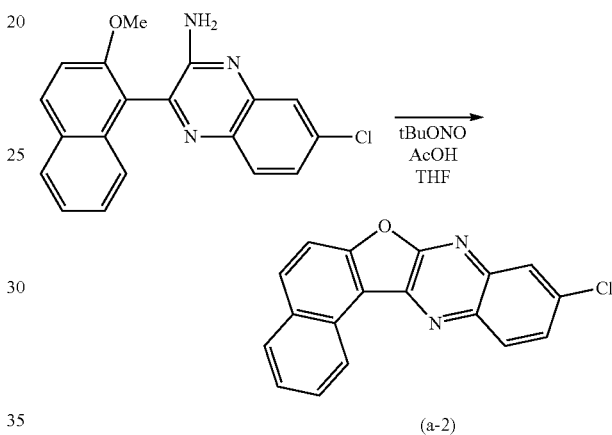

<Step 3; Synthesis of 10mDBtBPNfqn>

Next, into a three-neck flask were put 1.63 g of 10-chloronaphtho[1',2':4,5]furo[2,3-b]quinoxaline obtained in Step 2, 3.29 g of 3'-(4-dibenzothiophene)-1,1'-biphenyl-3-boronic acid, 5.48 g of tripotassium phosphate, 1.42 g of tert-butyl alcohol, and 60 mL of diethylene glycol dimethyl ether (abbreviation: diglyme), and the air in the flask was replaced with nitrogen. The mixture in the flask was degassed by being stirred under reduced pressure, 0.10 g of palladium(II) acetate (abbreviation: Pd(OAc)$_2$) and 0.32 g of di(1-adamantyl)-n-butylphosphine (abbreviation: CataCXium A) were added thereto, and then stirring was performed at 140° C. for 31.5 hours for reaction.

After a predetermined time elapsed, the obtained suspension was subjected to suction filtration, followed by washing with water and ethanol. The obtained solid was dissolved in toluene, and the mixture was filtered through a filter aid in which Celite, alumina, and Celite were stacked in this order and was recrystallized with toluene, whereby a substance that was the object was obtained (a yellow solid, 2.19 g, in a yield of 69%).

By a train sublimation method, 2.19 g of the obtained yellow solid was purified by sublimation. The conditions of the purification by sublimation were such that the solid was heated under a pressure of 2.7 Pa at 340° C. while the argon gas flowed at a flow rate of 15 mL/min. After the purification by sublimation, 1.48 g of a yellow solid that was the object was obtained in a yield of 68%. The synthesis scheme of Step 3 is shown in (a-3).

[Chemical Formula 31]

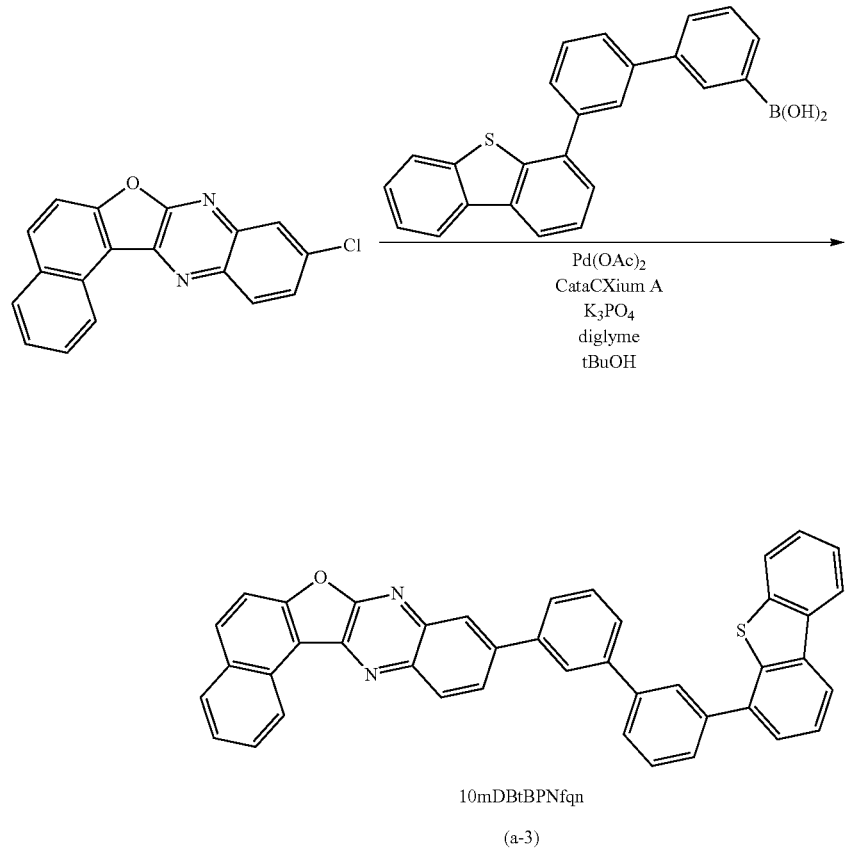

10mDBtBPNfqn (a-3)

Figure 10:
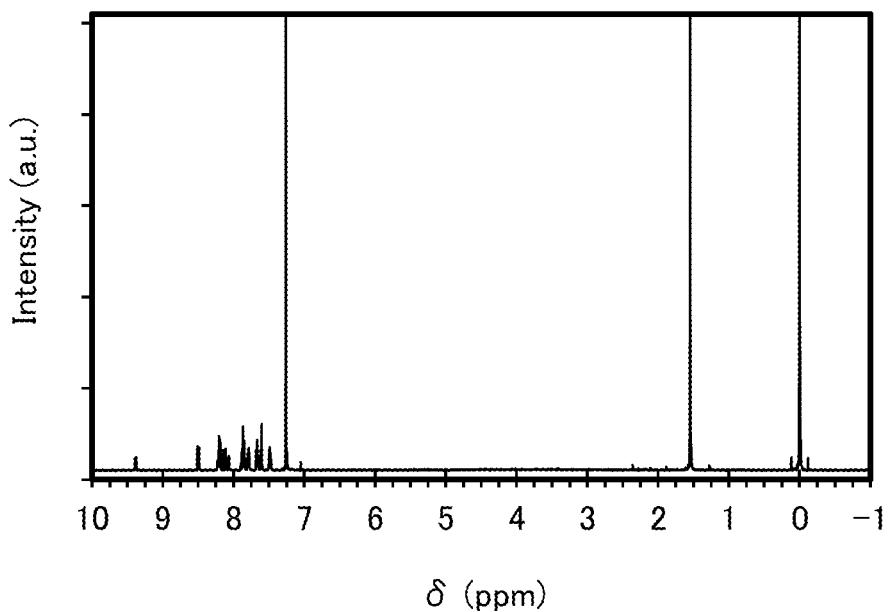
FIG. 10 is a chart of an organic compound represented by Structural Formula (100).

Analysis results by nuclear magnetic resonance spectroscopy ($^{1}$H-NMR) of the yellow solid obtained in Step 3 are shown below. FIG. 10 is the $^{1}$H-NMR chart. The results revealed that 10mDBtBPNfqn, which is represented by Structural Formula (100), was obtained in this example.

$^{1}$H-NMR. δ (CDCl$_{3}$): 7.47-7.50 (m, 2H), 7.60-7.62 (m, 2H), 7.67 (t, 3H), 7.78-7.80 (m, 3H), 7.85-7.90 (m, 4H), 8.07 (d, 1H), 8.13 (d, 2H), 8.19-8.23 (m, 4H), 8.49-8.51 (m, 2H), 9.39 (d, 1H).

Figure 11A:
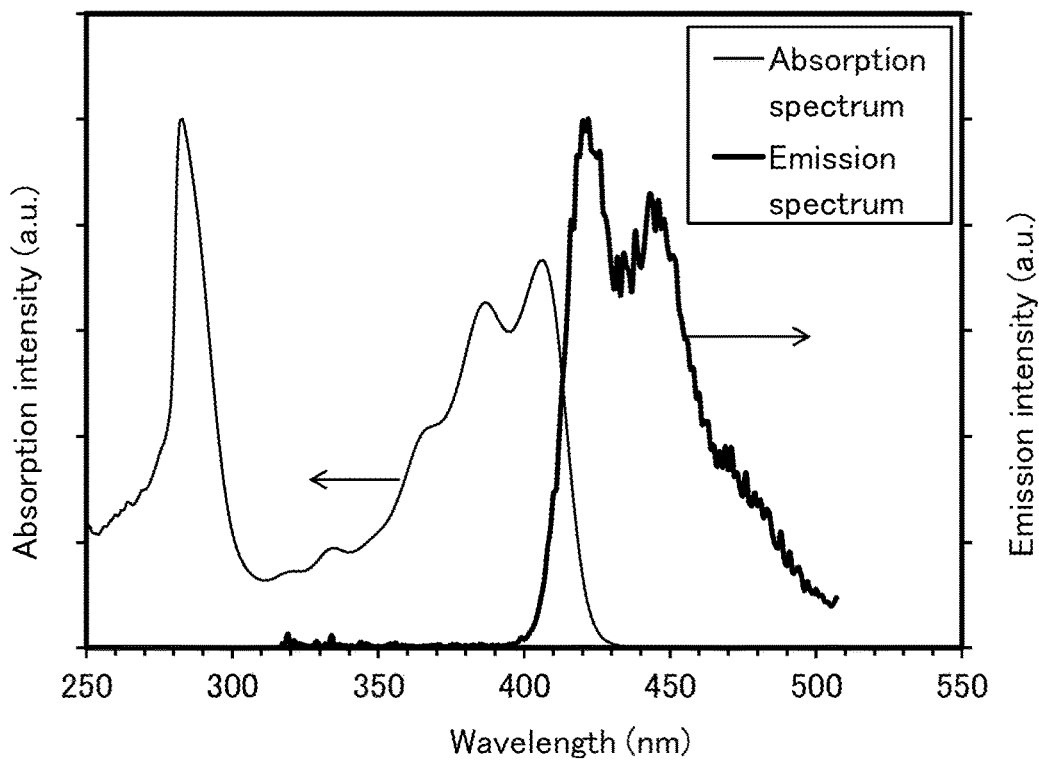
FIG. 11A and FIG. 11B are ultraviolet-visible absorption and emission spectra of the organic compound represented by Structural Formula (100).

Next, FIG. 11A shows an ultraviolet-visible absorption spectrum (hereinafter, simply referred to as "absorption spectrum") and an emission spectrum of 10mDBtBPNfqn in a toluene solution. The horizontal axis represents the wavelength, and the vertical axes represent the absorption intensity and the emission intensity. Note that absorption spectrum and the emission spectrum were both measured at room temperature.

The absorption spectrum was measured using an ultraviolet-visible spectrophotometer (V550, produced by JASCO Corporation). The absorption spectrum of 10mDBtBPNfqn in the toluene solution was obtained by subtracting absorption spectra of toluene put in a quartz cell from an absorption spectrum of the toluene solution of 10mDBtBPNfqn put in the quartz cell. The emission spectrum was measured using a fluorescence spectrophotometer (FS920 manufactured by Hamamatsu Photonics K.K.). The emission spectrum of 10mDBtBPNfqn in the toluene solution was measured with the toluene solution of 10mDBtBPNfqn put in a quartz cell.

From FIG. 11A, for the toluene solution of 10mDBtBPNfqn, absorption peaks were found at around 387 nm and around 406 nm and emission wavelength peaks were found at around 422 nm and around 443 nm (excitation wavelength: 292 nm).

Figure 11B:
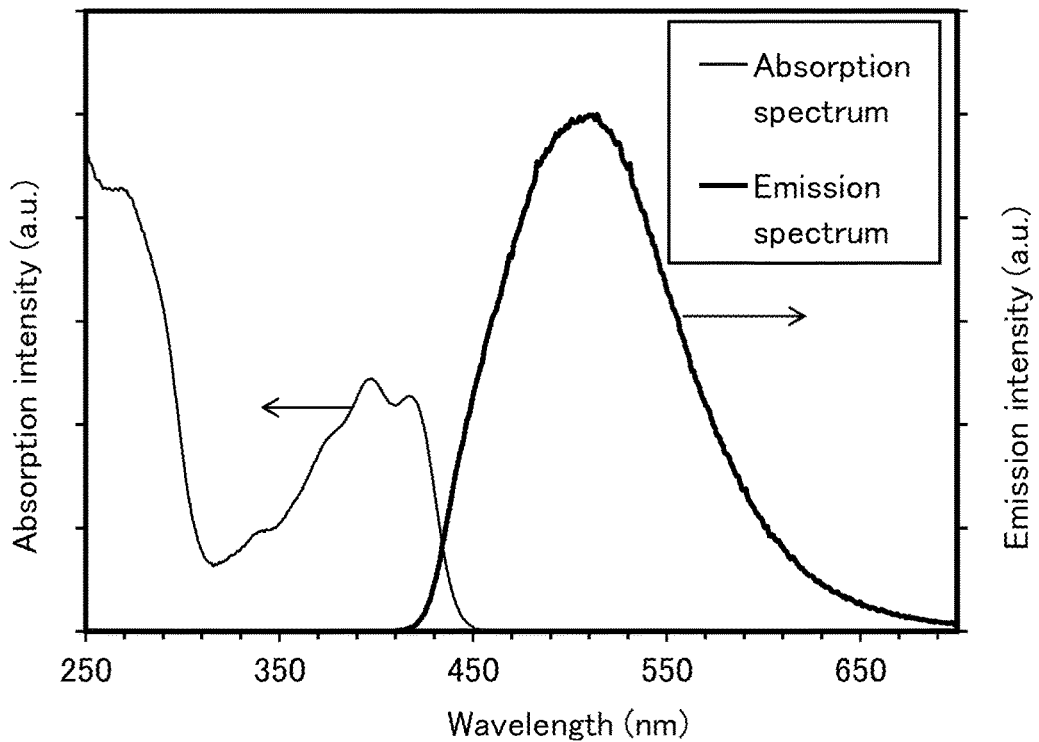

Next, absorption and emission spectra of 10mDBtBPNfqn in a solid thin film were measured. The solid thin film was fabricated over a quartz substrate by a vacuum evaporation method. The absorption spectrum of the thin film was calculated using an absorbance ($-\log_{10}$[% T/(100−% R)] obtained from a transmittance and a reflectance of the substrate and the thin film. Note that % T represents transmittance and % R represents reflectance. The absorption spectrum was measured using an ultraviolet-visible spectrophotometer (U-4100, manufactured by Hitachi High-Technologies Corporation). For the measurement of the emission spectrum, a fluorescence spectrophotometer (FS920 manufactured by Hamamatsu Photonics K.K.) was used. Note that absorption spectrum and the emission spectrum were both measured at room temperature. FIG. 11B shows the obtained measurement results of the absorption spectrum and emission spectrum of the solid thin film. The horizontal axis represents the wavelength, and the vertical axes represent the absorption intensity and the emission intensity.

From FIG. 11B, for the solid thin film of 10mDBtBPNfqn, absorption peaks were found at around 397 nm and around 418 nm and an emission wavelength peak was found at around 514 nm (excitation wavelength: 400 nm).

The organic compound of one embodiment of the present invention, 10mDBtBPNfqn, is found to be a host material suitably used with a phosphorescent material that emits red light and light with energy at a wavelength longer than that of red light. Furthermore, 10mDBtBPNfqn can be used as a host material used with a substance that emits light in the visible region (such as a fluorescent material, a delayed fluorescent material, or a phosphorescent material) or can be used as a light-emitting substance.

Differential scanning calorimetry of 10mDBtBPNfqn was performed. For the measurements, a differential scanning calorimeter (Pyris 1, manufactured by PerkinElmer Japan Co., Ltd.) was used. One cycle was as follows: the temperature was increased in the range of −10° C. to 350° C. at a rate of 40° C./min, then kept at 350° C. for 3 minutes, and decreased in the range of 350° C. to −10° C. at a rate of 100° C./min. Note that in this example, 3-cycle measurements were performed. The result at the time of the temperature increase in the third cycle shows that the glass transition temperature (Tg) was 126° C. Thus, 10mDBtBPNfqn synthesized in this example is a material having high heat resistance.

Since the Tg of 10mDBtBPNfqn is 126° C., the heat resistance of a light-emitting device can be improved.

The material, 10mDBtBPNfqn, is an example in which $Ar^1$ in General Formula (G0) is an unsubstituted naphthalene ring. Since $Ar^1$ is a naphthalene ring, the $T_1$ level can be made low and the LUMO level can be made deep, which probably enabled the synthesis of the host material suitable for a material that emits light with energy at a wavelength longer than or equal to that of red light.

The material, 10mDBtBPNfqn, is an example in which the organic compound of one embodiment of the present invention includes a dibenzothiophene skeleton as a hole-transport skeleton or a fused ring. A dibenzothiophene ring probably enabled the synthesis of the organic compound having high chemical stability and high heat resistance.

Example 2

In this example, the results of fabricating a light-emitting device of one embodiment of the present invention will be described. Specifically, the description is made on a structure, a fabrication method, and characteristics of Light-emitting Device 1 using 10-[(3'-dibenzothiophen-4-yl)biphenyl-3-yl]naphtho[1',2':4,5]furo[2,3-b]quinoxaline (abbreviation: 10mDBtBPNfqn) (Structural Formula (100)), which is described in Example 1, in a light-emitting layer.

Figure 12:
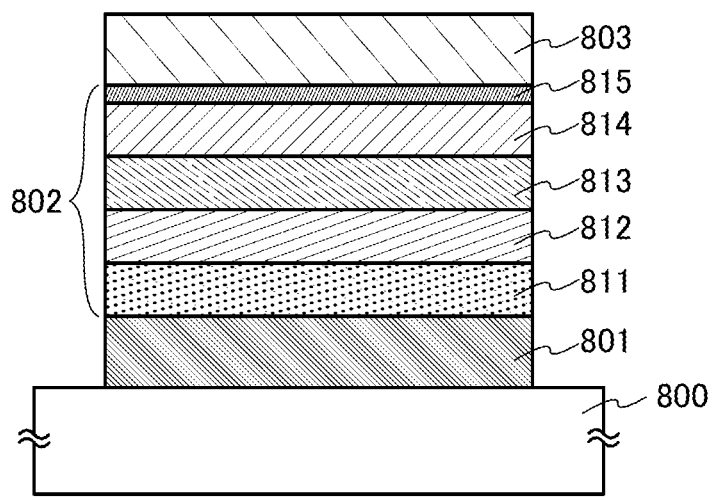
FIG. 12 is a cross-sectional view illustrating a light-emitting device of Example.

FIG. 12 illustrates the structure of Light-emitting Device 1 used in this example, and Table 1 shows specific components. The chemical formulae of the materials used in this example are shown below.

TABLE 1

| | First electrode 801 | Hole-injection layer 811 | Hole-transport layer 812 | Light-emitting layer 813 | Electron-transport layer 814 | Electron-injection layer 815 | Second electrode 803 |
| --- | --- | --- | --- | --- | --- | --- | --- |
| Light-emitting Device 1 | ITSO (70 nm) | DBT3P-II:MoOx (2:1 80 nm) | PCBBiF (20 nm) | * | 10mDBtBPNfqn (30 nm) | NBphen (15 nm) | LiF (1 nm) | Al (200 nm) |

* 10mDBtBPNfqn:PCBBiF:[Ir(dpq)$_2$(acac)] (0.8:0.2:0.1 40 nm)

[Chemical Formula 32]

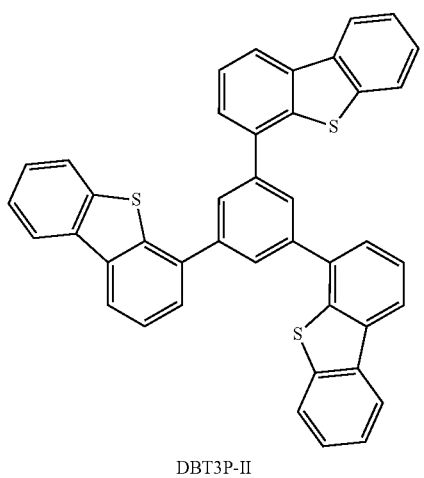

DBT3P-II

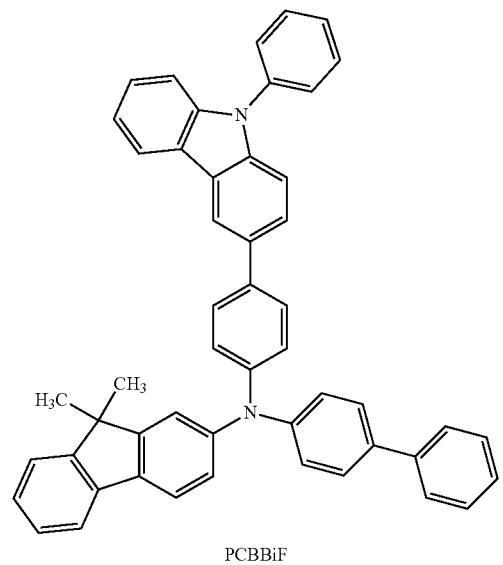

PCBBiF

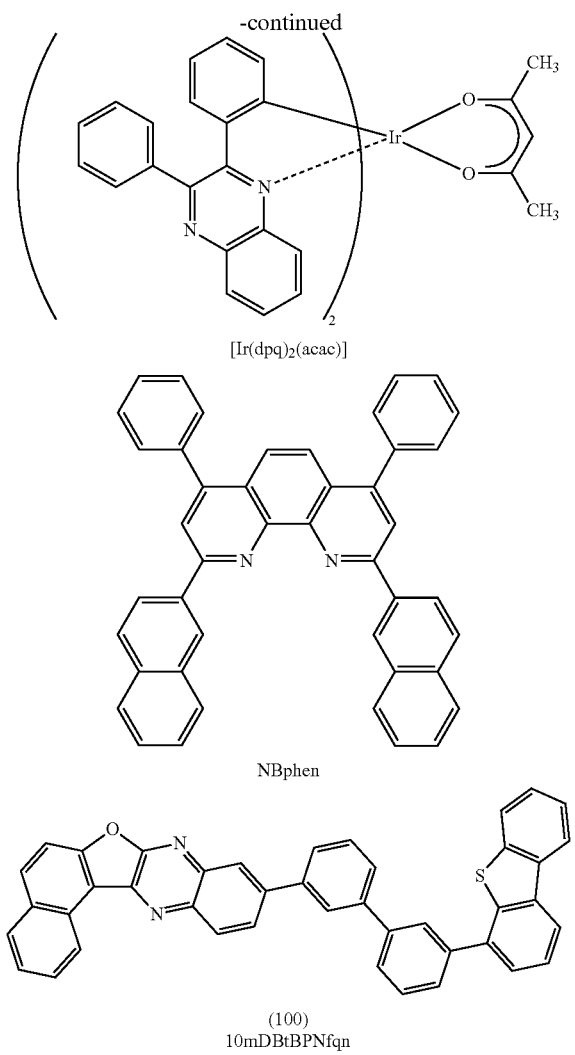

[Ir(dpq)₂(acac)]

NBphen (100)
10mDBtBPNfqn

<<Fabrication of Light-Emitting Device 1>>

Light-emitting Device 1 described in this example has a structure in which a first electrode 801 is formed over a substrate 800; a hole-injection layer 811, a hole-transport layer 812, a light-emitting layer 813, an electron-transport layer 814, and an electron-injection layer 815 are stacked in this order over the first electrode 801; and a second electrode 803 is stacked over the electron-injection layer 815, as illustrated in FIG. 12.

First, the first electrode 801 was formed over the substrate 800. The electrode area was set to 4 mm² (2 mm×2 mm). A glass substrate was used as the substrate 800. The first electrode 801 was formed to a thickness of 70 nm using indium tin oxide containing silicon oxide (ITSO) by a sputtering method. In this example, the first electrode 801 functions as an anode.

As pretreatment, a surface of the substrate was washed with water, baking was performed at 200° C. for one hour, and then UV ozone treatment was performed for 370 seconds. After that, the substrate was transferred into a vacuum evaporation apparatus in which the pressure was reduced to approximately $10^{-4}$ Pa, vacuum baking at 170° C. for 30 minutes was performed in a heating chamber in the vacuum evaporation apparatus, and then the substrate was cooled down for approximately 30 minutes.

Next, the hole-injection layer 811 was formed over the first electrode 801. For the formation of the hole-injection layer 811, the pressure in the vacuum evaporation apparatus was reduced to $10^{-4}$ Pa, and then 1,3,5-tri(dibenzothiophen-4-yl)benzene (abbreviation: DBT3P-II) and molybdenum oxide were co-evaporated such that DBT3P-II:molybdenum oxide=2:1 (mass ratio) and the thickness was 80 nm.

Then, the hole-transport layer 812 was formed over the hole-injection layer 811. The hole-transport layer 812 was formed to a thickness of 20 nm by evaporation of N-(1,1'-biphenyl-4-yl)-N-[4-(9-phenyl-9H-carbazol-3-yl)phenyl]-9,9-dimethyl-9H-fluoren-2-amine (abbreviation: PCBBiF).

Next, the light-emitting layer 813 was formed over the hole-transport layer 812. Co-evaporation was performed using 10mDBtBPNfqn, which is an organic compound of one embodiment of the present invention, as a host material, PCBBiF as an assist material, and (acetylacetonato)bis(2,3-diphenylquinoxalinato-N,C²')iridium(III) (abbreviation: [Ir(dpq)₂(acac)]) as a guest material (phosphorescent material) such that the weight ratio was 10mDBtBPNfqn:PCBBiF:[Ir(dpq)₂(acac)]=0.8:0.2:0.1. Note that the thickness was set to 40 nm.

Next, the electron-transport layer 814 was formed over the light-emitting layer 813. The electron-transport layer 814 was formed by sequential deposition by evaporation so that the thickness of 10mDBtBPNfqn was 30 nm and the thickness of 2,9-bis(naphthalen-2-yl)-4,7-diphenyl-1,10-phenanthroline (abbreviation: NBphen) was 15 nm.

Then, the electron-injection layer 815 was formed over the electron-transport layer 814. The electron-injection layer 815 was formed to a thickness of 1 nm by evaporation of lithium fluoride (LiF).

Next, the second electrode 803 was formed over the electron-injection layer 815. The second electrode 803 was formed to a thickness of 200 nm by an evaporation method using aluminum. In this example, the second electrode 803 functions as a cathode.

Through the above steps, the light-emitting device in which an EL layer was provided between the pair of electrodes over the substrate 800 were fabricated. The hole-injection layer 811, the hole-transport layer 812, the light-emitting layer 813, the electron-transport layer 814, and the electron-injection layer 815 described in the above steps are functional layers forming the EL layer in one embodiment of the present invention. Furthermore, in all the evaporation steps in the above fabrication method, an evaporation method by a resistance-heating method was used.

The light-emitting device fabricated as described above was sealed using a different substrate (not illustrated). At the time of the sealing using the different substrate (not illustrated), the different substrate (not illustrated) on which an adhesive that is solidified by ultraviolet light was applied was fixed onto the substrate 800 in a glove box containing a nitrogen atmosphere, and the substrates were bonded to each other such that the adhesive was attached to the periphery of the light-emitting device formed over the substrate 800. At the time of the sealing, the adhesive was irradiated with 365-nm ultraviolet light at 6 J/cm² to be solidified, and the adhesive was subjected to heat treatment at 80° C. for one hour to be stabilized.

<<Operating Characteristics of Light-Emitting Device 1>>

The operating characteristics of Light-emitting Device 1 were measured. Note that the measurement was carried out at room temperature (an atmosphere maintained at 25° C.).

Figure 13:
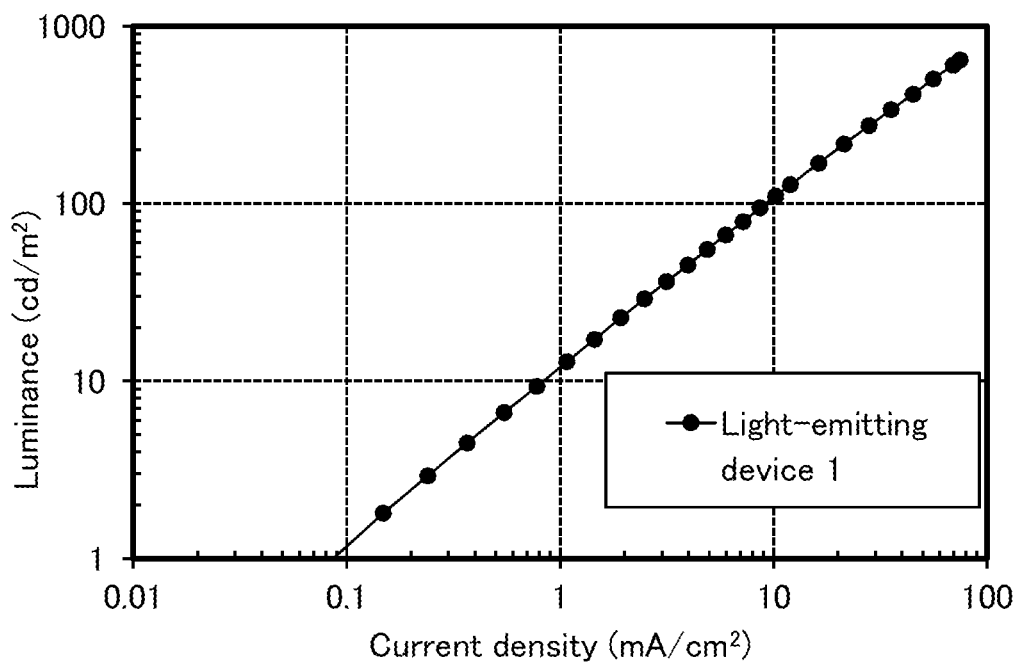
FIG. 13 is a diagram showing current density-luminance characteristics of Light-emitting Device 1.
Figure 14:
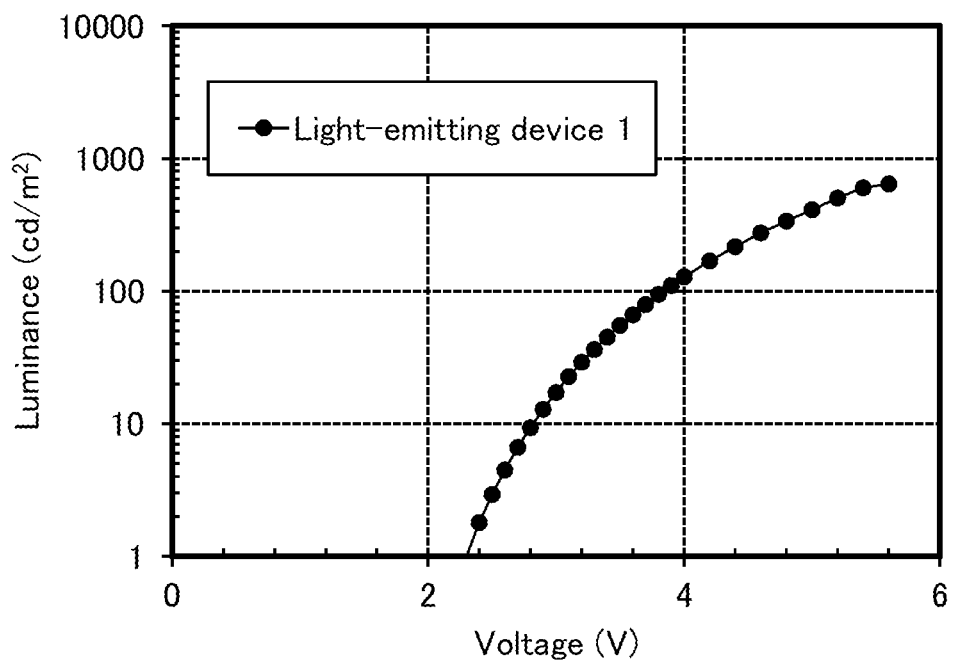
FIG. 14 is a diagram showing voltage-luminance characteristics of Light-emitting Device 1.

FIG. 13 shows the current density—luminance characteristics of Light-emitting Device 1. FIG. 14 shows the voltage—luminance characteristics of Light-emitting Device 1.

Figure 15:
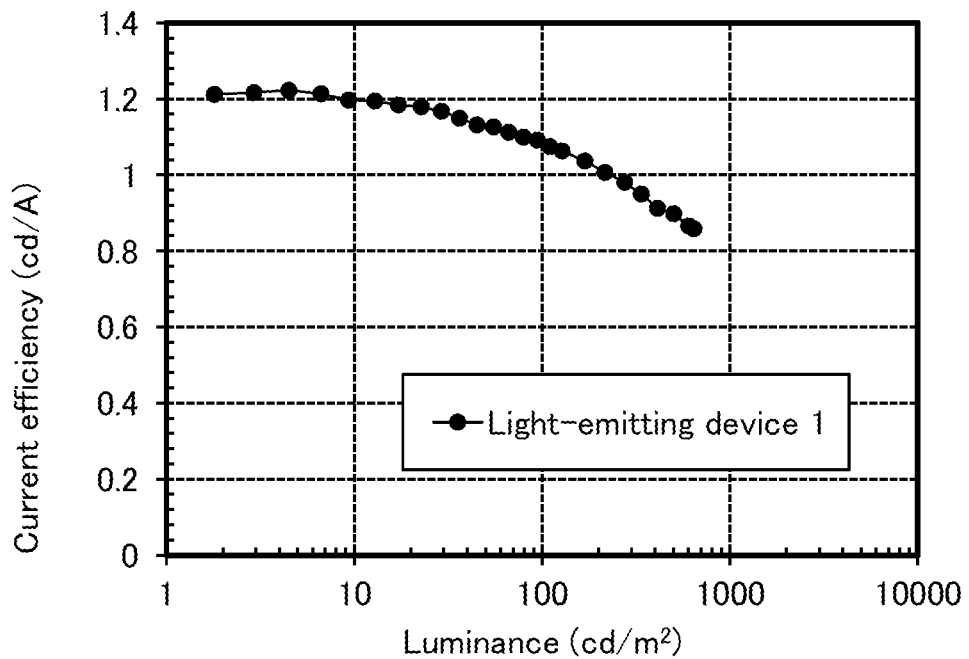
FIG. 15 is a diagram showing luminance-current efficiency characteristics of Light-emitting Device 1.
Figure 16:
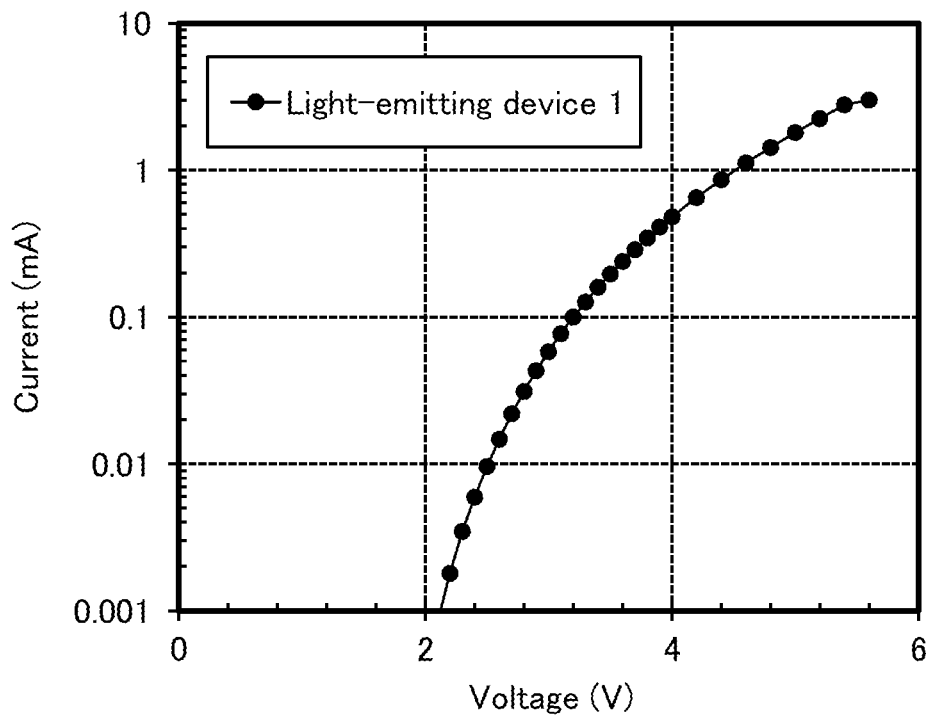
FIG. 16 is a diagram showing voltage-current characteristics of Light-emitting Device 1.
Figure 17:
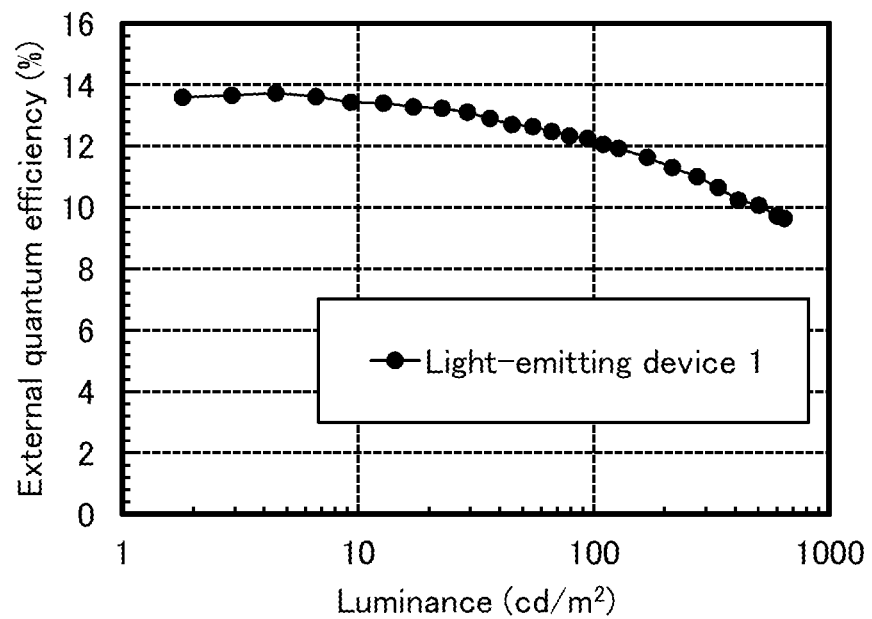
FIG. 17 is a diagram showing luminance-external quantum efficiency characteristics of Light-emitting Device 1.

FIG. 15 shows the luminance—current efficiency characteristics of Light-emitting Device 1. FIG. 16 shows the voltage—current characteristics of Light-emitting Device 1. FIG. 17 shows the luminance—external quantum efficiency characteristics of Light-emitting Device 1.

Table 2 lists the initial values of main characteristics of Light-emitting Device 1 at around 600 cd/m².

TABLE 2

| | Voltage (V) | Current (mA) | Current density (mA/cm²) | Chromaticity (x, y) | Luminance (cd/m²) | Current efficiency (cd/A) | Power efficiency (lm/W) | External quantum efficiency (%) |
|---|---|---|---|---|---|---|---|---|
| Light-emitting Device 1 | 5.4 | 2.8 | 70 | (0.75, 0.25) | 600 | 0.87 | 0.50 | 9.7 |

As shown in FIG. 13 to FIG. 17 and Table 2, Device 1 has high emission efficiency.

Figure 18:
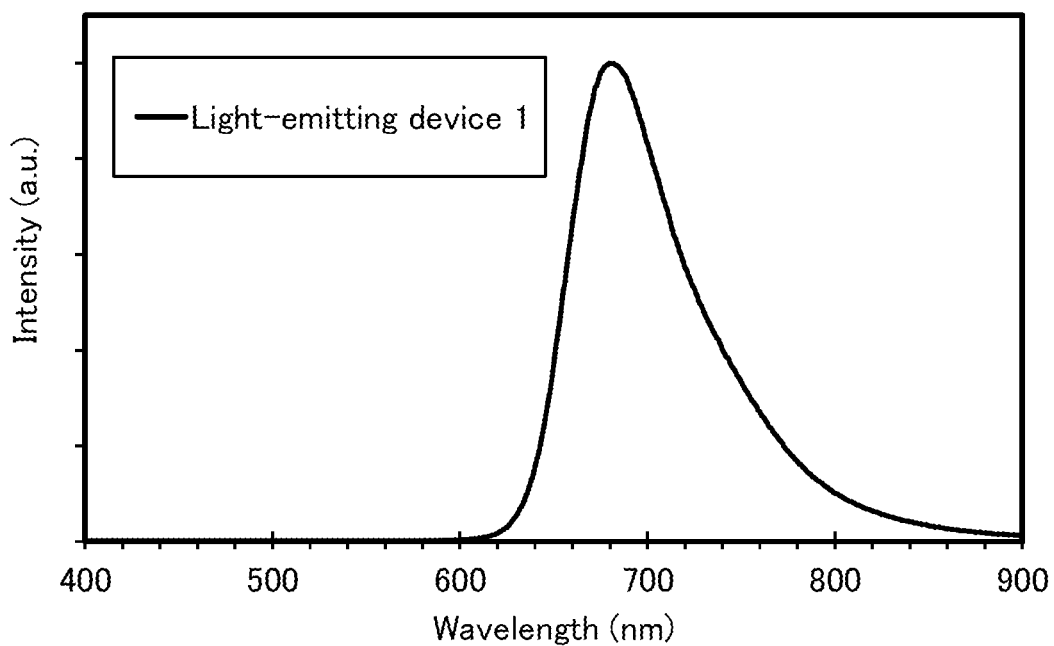
FIG. 18 is a diagram showing an emission spectrum of Light-emitting Device 1.

FIG. 18 shows an emission spectrum when current at a current density of 2.5 mA/cm² was supplied to Light-emitting Device 1. As shown in FIG. 18, Light-emitting Device 1 exhibited an emission spectrum having a maximum peak at around 680 nm, which was derived from light emitted from [Ir(dpq)₂(acac)] included in the light-emitting layer 813.

Next, a reliability test was performed on Light-emitting Device 1. Results of the reliability test are shown in FIG. 19.

Figure 19:
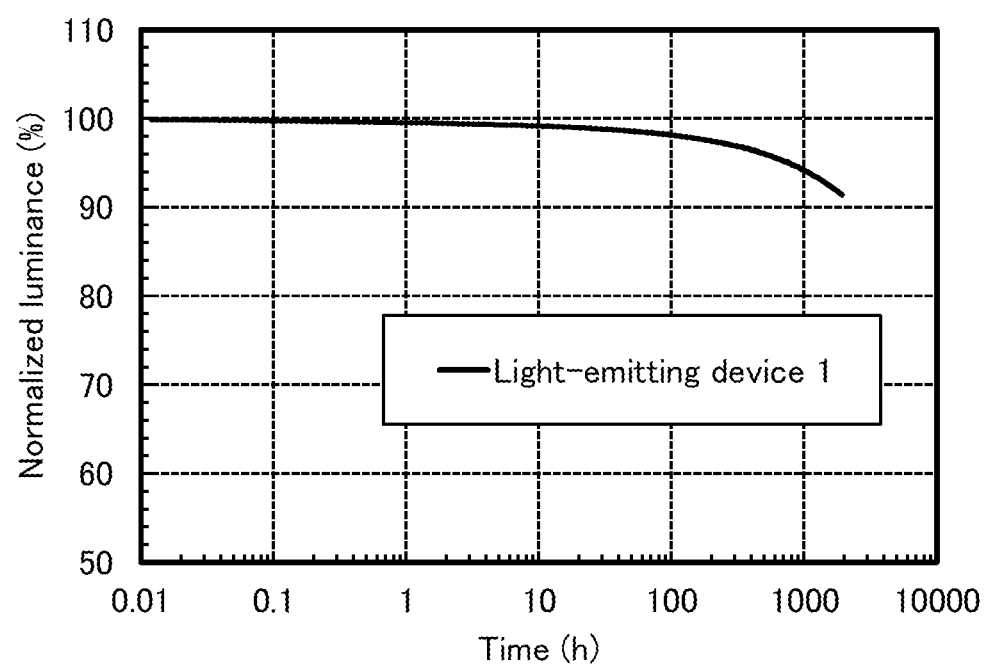
FIG. 19 is a diagram showing reliability test results of Light-emitting Device 1.

In FIG. 19, the vertical axis represents normalized luminance (%) with an initial luminance of 100%, and the horizontal axis represents driving time (h). In the reliability test, Light-emitting Device 1 was driven at a current density of 75 mA/cm².

The results of the reliability test showed that Light-emitting Device 1 has high reliability. This can be regarded as the effect of using 10mDBtBPNfqn (Structural Formula (100)), which is the organic compound of one embodiment of the present invention, in the light-emitting layer of Light-emitting Device 1.

In Light-emitting Device 1, 10mDBtBPNfqn and PCBBiF used in the light-emitting layer form an exciplex when combined. The organic compound of one embodiment of the present invention that includes the dibenzothiophene skeleton as the hole-transport skeleton is considered to have a deep HOMO level or a low hole-transport property or promote the formation of an exciplex, which was suggested to increase the reliability of the light-emitting device.

Example 3

In this example, the results of fabricating a light-emitting device of one embodiment of the present invention will be described. Specifically, the results of measuring characteristics of Light-emitting Device 2 and Light-emitting Device 3 using 10-[(3'-dibenzothiophen-4-yl)biphenyl-3-yl]naphtho[1',2':4,5]furo[2,3-b]quinoxaline (abbreviation: 10mDBtBPNfqn) (Structural Formula (100)) described in Example 1 in light-emitting layers, which were fabricated.

Table 3 shows specific components of Light-emitting Devices 2 and 3 used in this example. Note that Light-emitting Devices 2 and 3 have the same structure as Light-emitting Device 1 (FIG. 12); thus, Example 2 can be referred to for the fabrication method. The chemical formulae of the materials used in this example are shown below.

TABLE 3

| | First electrode 801 | Hole-injection layer 811 | Hole-transport layer 812 | Light-emitting layer 813 | Electron-transport layer 814 | Electron-injection layer 815 | Second electrode 803 |
|---|---|---|---|---|---|---|---|
| Light-emitting Device 2 | ITSO (70 nm) | DBT3P-I:LMoOx (2:1 75 nm) | PCBBiF (20 nm) | * | 10mDBtBPNfqn (30 nm) | NBphen (15 nm) | LiF (1 nm) / Al (200 nm) |
| Light-emitting Device 3 | ITSO (70 nm) | DBT3P-I:LMoOx (2:1 75 nm) | PCBBiF (20 nm) | ** | 10mDBtBPNfqn (30 nm) | NBphen (15 nm) | LiF (1 nm) / Al (200 nm) |

\* 10mDBtBPNfqn:PCBiF:[Ir(dmdppr-m5CP)₂(dpm)] (0.8:0.2:0.1 40 nm)
\*\* 10mDBtBPNfqn:FrBBiF-II:[Ir(dmdppr-m5CP)₂(dpm)] (0.8:0.2:0.1 40 nm)

[Chemical Formula 33]

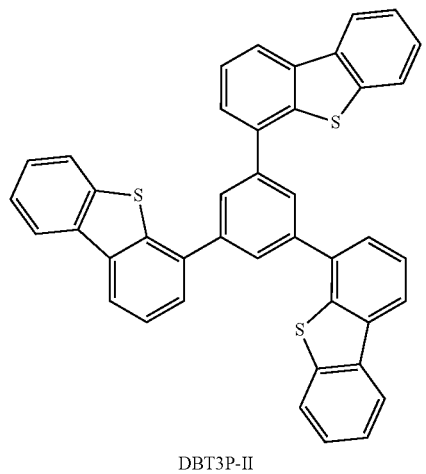

DBT3P-II

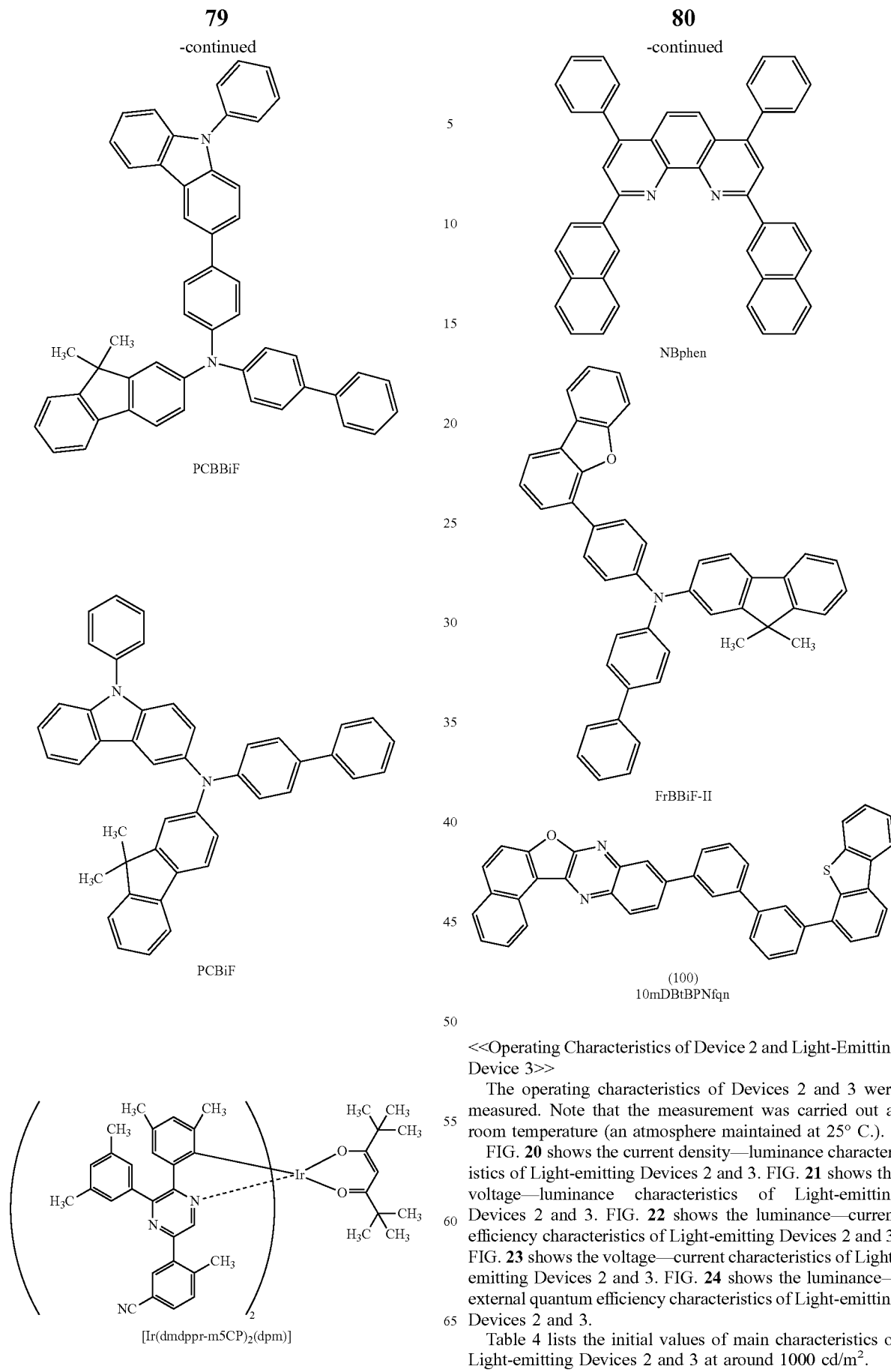

<<Operating Characteristics of Device 2 and Light-Emitting Device 3>>

The operating characteristics of Devices 2 and 3 were measured. Note that the measurement was carried out at room temperature (an atmosphere maintained at 25° C.).

Figure 20:
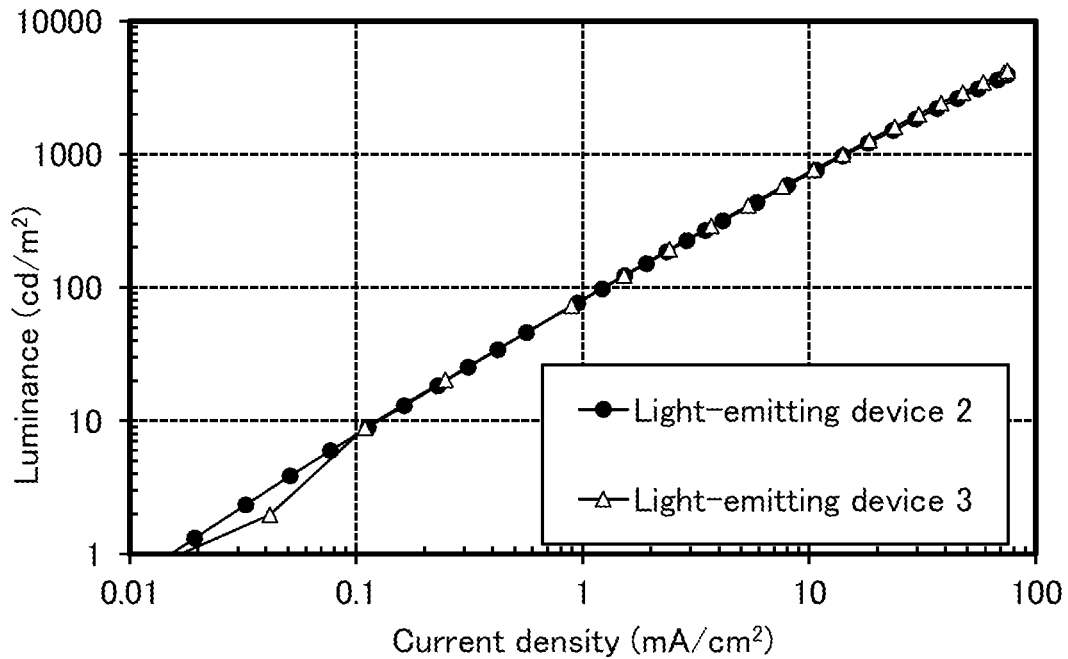
FIG. 20 is a diagram showing current density-luminance characteristics of Light-emitting Devices 2 and 3.
Figure 21:
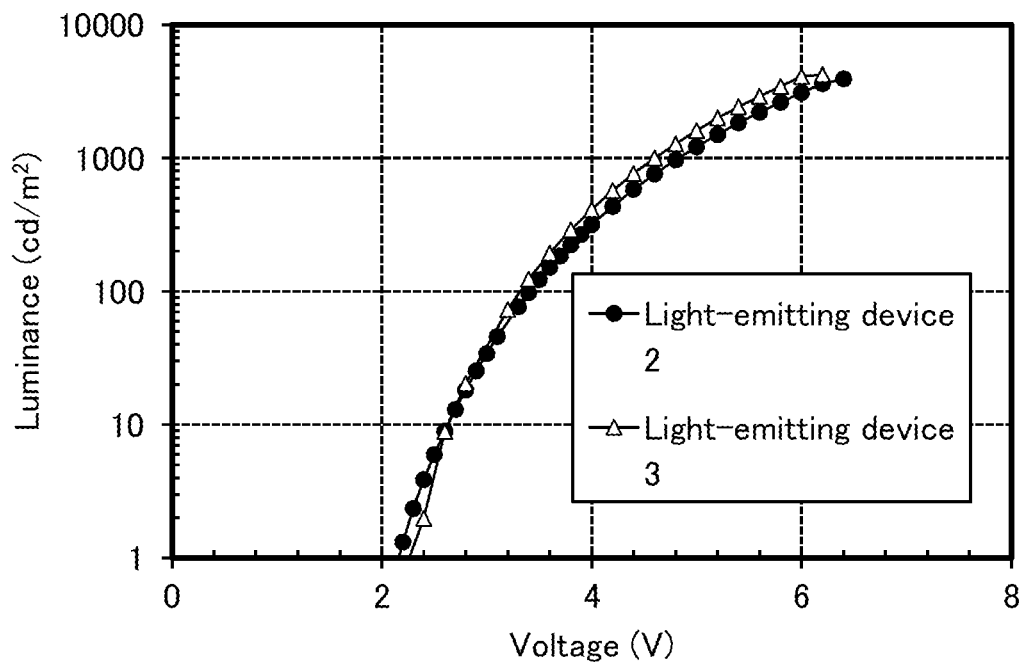
FIG. 21 is a diagram showing voltage-luminance characteristics of Light-emitting Devices 2 and 3.
Figure 22:
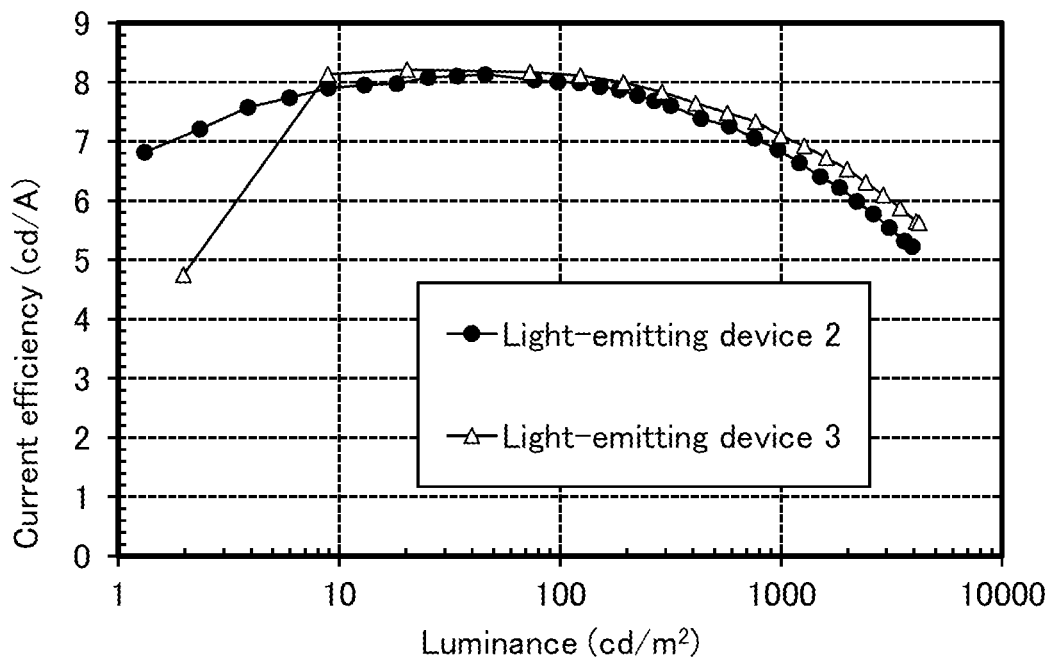
FIG. 22 is a diagram showing luminance-current efficiency characteristics of Light-emitting Devices 2 and 3.
Figure 23:
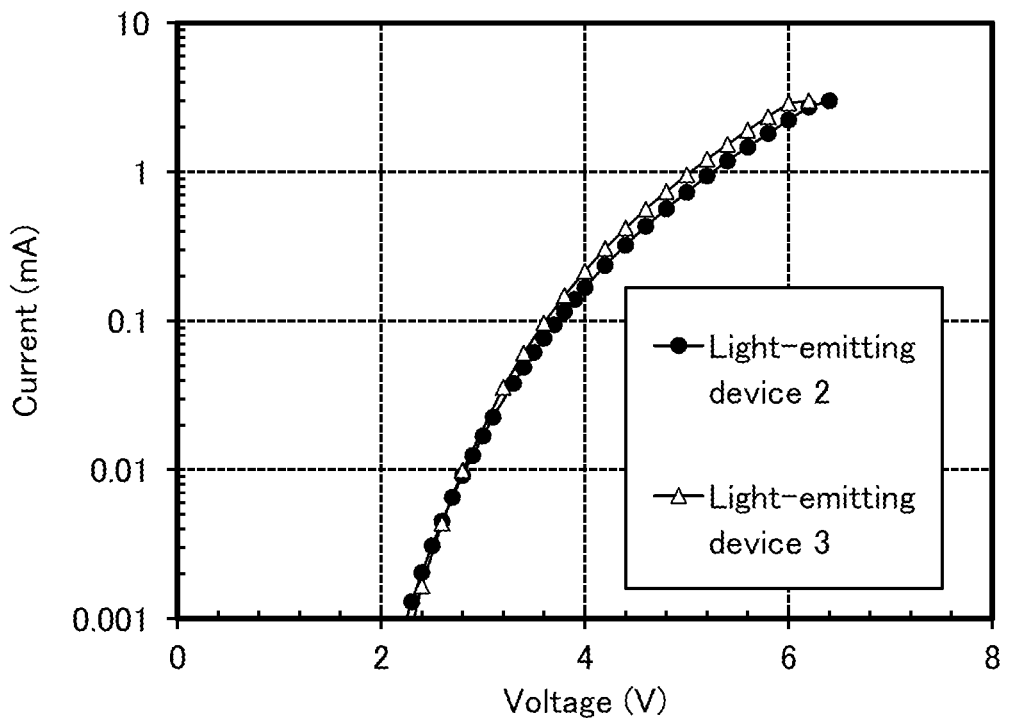
FIG. 23 is a diagram showing voltage-current characteristics of Light-emitting Devices 2 and 3.
Figure 24:
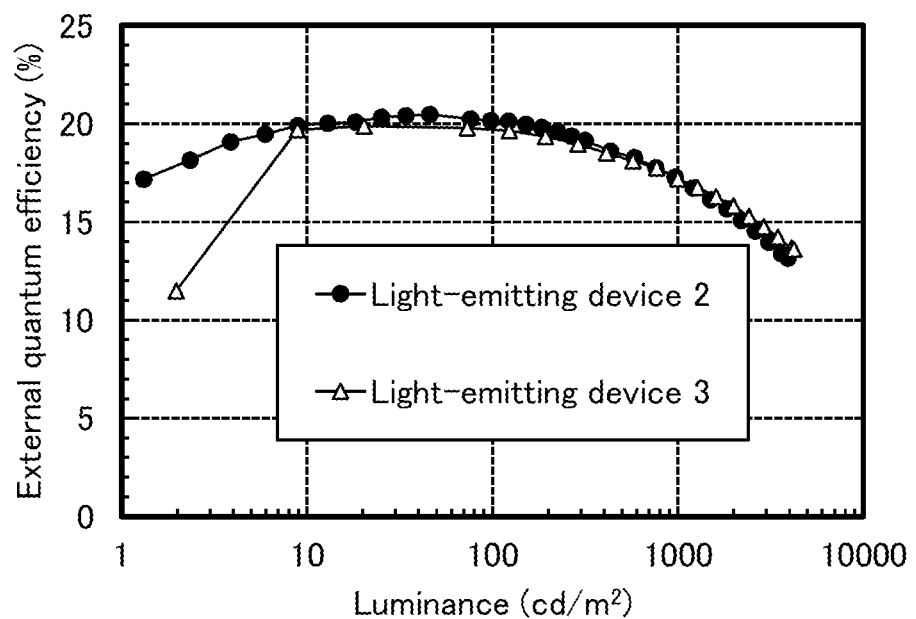
FIG. 24 is a diagram showing luminance-external quantum efficiency of Light-emitting Devices 2 and 3.

FIG. 20 shows the current density—luminance characteristics of Light-emitting Devices 2 and 3. FIG. 21 shows the voltage—luminance characteristics of Light-emitting Devices 2 and 3. FIG. 22 shows the luminance—current efficiency characteristics of Light-emitting Devices 2 and 3. FIG. 23 shows the voltage—current characteristics of Light-emitting Devices 2 and 3. FIG. 24 shows the luminance—external quantum efficiency characteristics of Light-emitting Devices 2 and 3.

Table 4 lists the initial values of main characteristics of Light-emitting Devices 2 and 3 at around 1000 cd/m$^2$.

TABLE 4

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting Device 2 | 4.8 | 0.56 | 14 | (0.71, 0.29) | 970 | 6.9 | 4.5 | 17 |
| Light-emitting Device 3 | 4.6 | 0.56 | 14 | (0.71, 0.29) | 1000 | 7.1 | 4.8 | 17 |

As shown in FIG. 20 to FIG. 24 and Table 4, Devices 2 and 3 have high emission efficiency.

Figure 25:
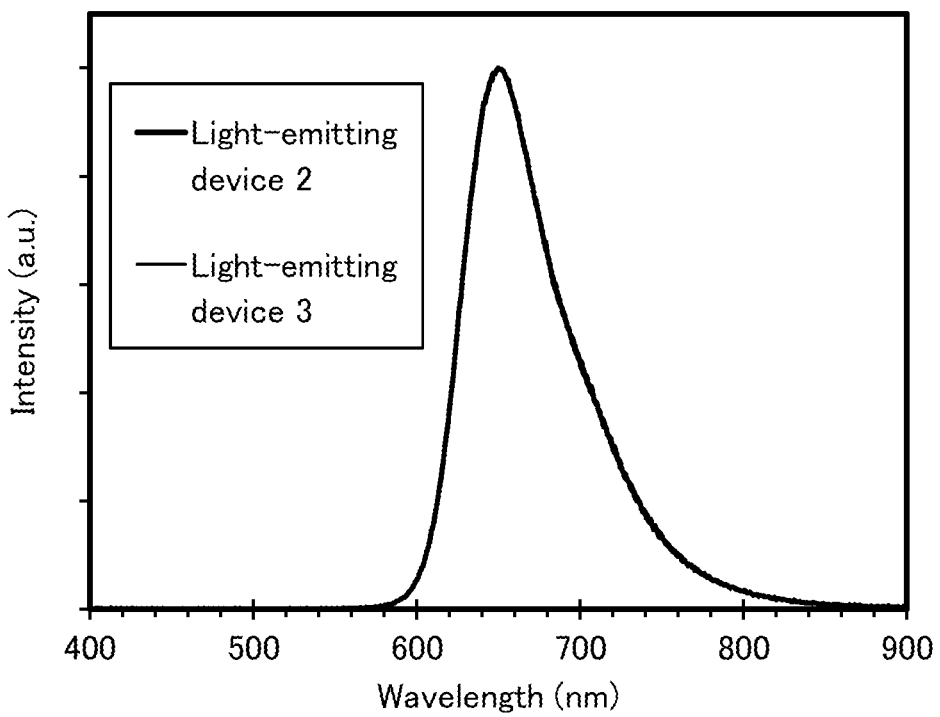
FIG. 25 is a diagram showing emission spectra of Light-emitting Devices 2 and 3.

FIG. 25 shows emission spectra of Light-emitting Devices 2 and 3 to which current flows at a current density of 2.5 mA/cm$^2$. Light-emitting Devices 2 and 3 exhibit the emission spectra having maximum peaks at around 650 nm, which are derived from light emitted from bis{4,6-dimethyl-2-[5-(5-cyano-2-methylphenyl)-3-(3,5-dimethylphenyl)-2-pyrazinyl-κN]phenyl-κC}(2,2,6,6-tetramethyl-3,5-heptane-dionato-κ2O,O')iridium(III) (abbreviation: [Ir(dmdppr-m5CP)$_2$(dpm)] included in the light-emitting layer 813. Specifically, Light-emitting Device 2 has a maximum peak at around 650 nm and Light-emitting Device 3 has a maximum peak at around 649 nm.

Figure 26:
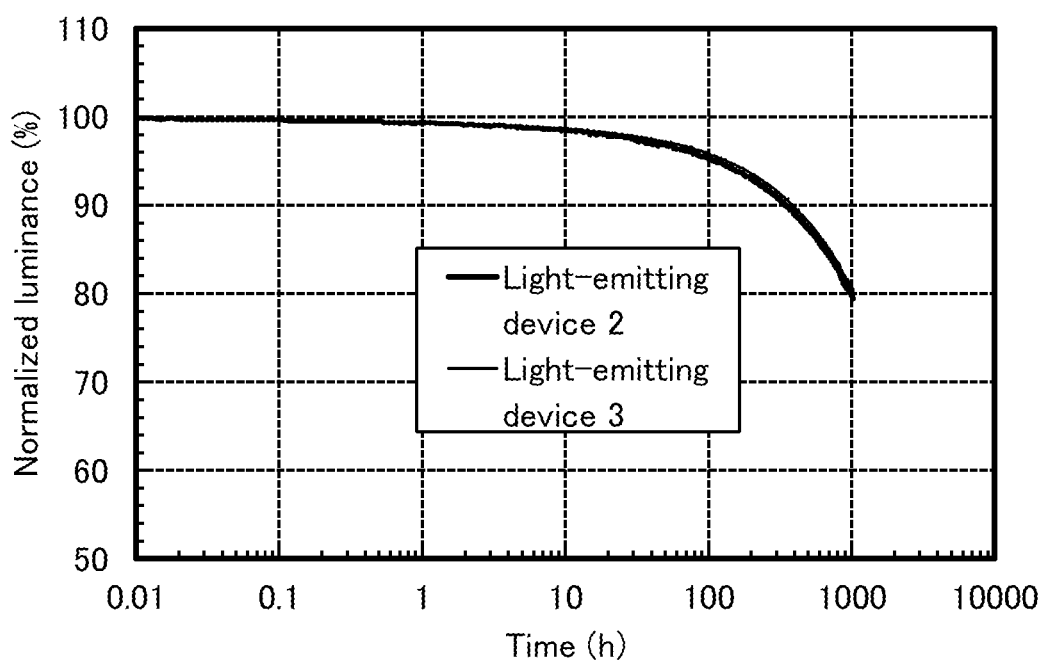
FIG. 26 is a diagram showing reliability test results of Light-emitting Devices 2 and 3.

Next, reliability tests were performed on Light-emitting Devices 2 and 3. Results of the reliability test are shown in FIG. 26. In FIG. 26, the vertical axis represents normalized luminance (%) with an initial luminance of 100%, and the horizontal axis represents driving time (h) of the elements. In the reliability tests, Light-emitting Devices 2 and 3 were driven at a current density of 75 mA/cm$^2$.

The results of the reliability test showed that Light-emitting Devices 2 and 3 have high reliability.

In this example, N-(4-biphenyl)-N-(9,9-dimethyl-9H-fluoren-2-yl)-9-phenyl-9H-carbazol-3-amine (abbreviation: PCBiF) was used for the light-emitting layer 813 in Light-emitting Device 2, and N-(1,1'-biphenyl-4-yl)-N-[4-(dibenzofuran-4-yl)phenyl]-9,9-dimethyl-9H-fluoren-2-amine (abbreviation: FrBBiF-II) was used for the light-emitting layer 813 in Light-emitting Device 3. The HOMO level of PCBiF is −5.26 eV, and the HOMO level of FrBBiF-II is −5.42 eV It is found that, in combination with either PCBiF or FrBBiF-II, a light-emitting device having favorable characteristics can be fabricated with the use of 10mDBtBPNfqn, which is an organic compound of one embodiment of the present invention for the light-emitting layer 813. Hence, the material (assist material) that can be used in combination with 10mDBtBPNfqn may have a wide range of preferred HOMO levels, and the assist material can be chosen from a wide range.

Example 4

This example shows calculation results to determine whether the substitution position of the hole-transport skeleton or the fused ring (the substitution position of R$^1$ or R$^2$) in General Formula (G0) changes the LUMO level and the T$_1$ level or not.

In this example, calculations were performed for the organic compounds represented by Structural Formulae (C1) to (C4).

[Chemical Formula 34]

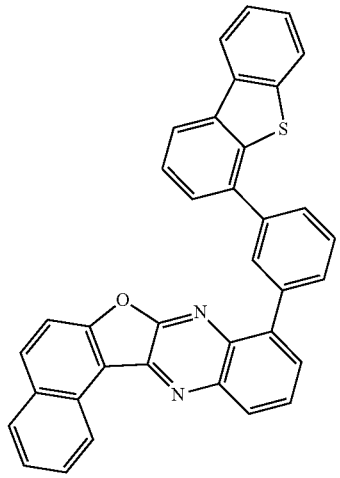
(C1)

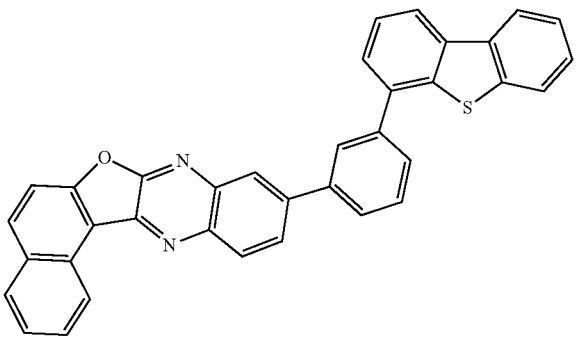
(C2)

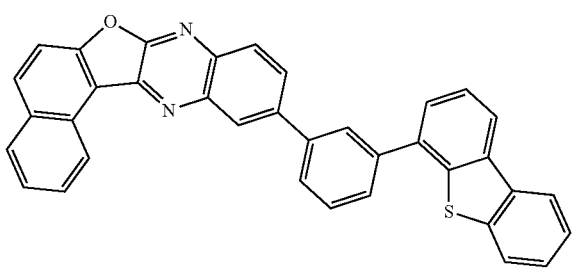
(C3)

(C4)

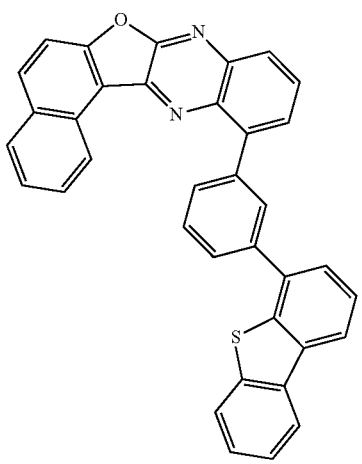

For molecular orbital calculations, Gaussian 09 was used as the quantum chemistry computational program. Structural optimization was performed on the singlet ground state ($S_0$) and the lowest triplet excited state ($T_1$) of each molecule using 6-311G as a basis and B3LYP as a functional.

Table 5 shows the values of the LUMO levels and the $T_1$ levels (wavelengths) obtained by the calculations.

TABLE 5

| Structural Formula | LUMO (eV) | $T_1$ level (wavelength) (nm) |
|---|---|---|
| C1 | −2.51 | 602 |
| C2 | −2.54 | 617 |
| C3 | −2.53 | 596 |
| C4 | −2.54 | 610 |

As shown in Table 5, the organic compounds represented by Structural Formulae (C1) to (C4) each have a deep LUMO level and a $T_1$ level (wavelength) of around 600 nm. In particular, Structural Formula (C2) is found to have the deepest LUMO level and the lowest $T_1$ level (the longest wavelength).

The results in this example indicate that the organic compound of one embodiment of the present invention has a deep LUMO level and a low $T_1$ level and thus is suitable for a light-emitting device (a light-emitting device emitting red or near-infrared light, in particular).

Example 5

Synthesis Example 2

In this example, a method of synthesizing an organic compound of one embodiment of the present invention will be described. In this example, the description is made on a method of synthesizing 12-[(3'-dibenzothiophen-4-yl)biphenyl-3-yl]phenanthro[9',10':4,5]furo[2,3-b]quinoxaline (abbreviation: 12mDBtBPPnfqn), which is represented by Structural Formula (113) in Embodiment 1.

[Chemical Formula 35]

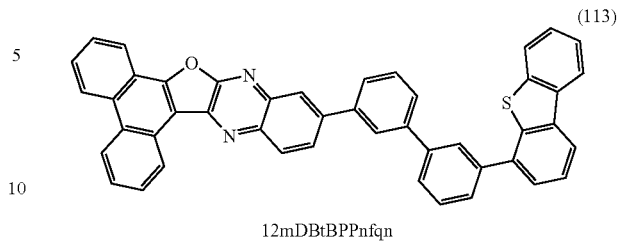

12mDBtBPPnfqn (113)

<Step 1; 7-chloro-3-(10-methoxyphenanthren-9-yl)quinoxalin-2-amine>

First, into a three-neck flask equipped with a reflux pipe were put 2.70 g of 3,7-dichloro quinoxalin-2-amine, 3.27 g of 10-methoxyphenanthrene-9-boronic acid, 4.22 g of cesium carbonate, 50 mL of 1,4-dioxane, and 25 mL of water, and the air in the flask was replaced with nitrogen. After the mixture in the flask was degassed by being stirred under reduced pressure, 0.75 g of tetrakis(triphenylphosphine)palladium(0) (abbreviation: Pd(PPh$_3$)$_4$) was added, and stirring was performed at 80° C. for 11 hours for reaction.

After a predetermined time elapsed, the precipitated solid was subjected to suction filtration, followed by washing with water and ethanol. After that, purification by silica gel column chromatography using dichloromethane as a developing solvent was performed, whereby the quinoxaline derivative that was the object was obtained (a yellow solid, yield: 3.30 g, 68%). The synthesis scheme of Step 1 is shown in (b-1).

[Chemical Formula 36]

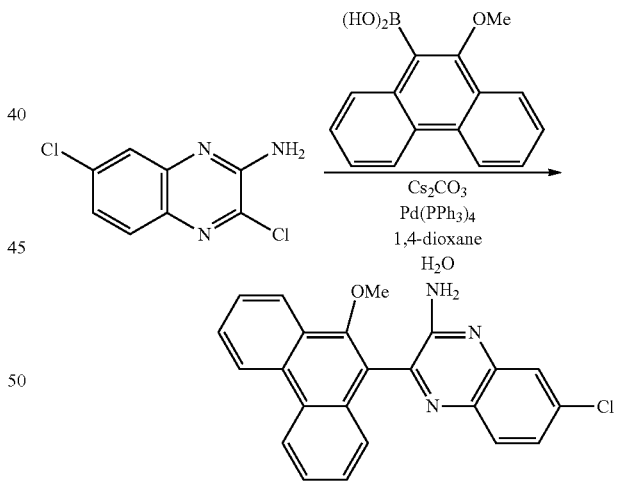

(b-1)

<Step 2; Synthesis of 12-chlorophenanthro[9',10':4,5]furo[2,3-b]quinoxaline>

Next, into a three-neck flask were put 3.29 g of 7-chloro-3-(10-methoxy phenanthrene-9-yl)quinoxalin-2-amine obtained in Step 1, 100 mL of dehydrated tetrahydrofuran, and 100 mL of a glacial acetic acid, and the air in the flask was replaced with nitrogen. After the flask was cooled down to −10° C., 3.1 mL of tert-butyl nitrite was dripped, and stirring was performed at −10° C. for 1 hour and at 0° C. for 24 hours. After a predetermined time elapsed, 400 mL of water was added to the obtained suspension and suction filtration was performed, whereby the quinoxaline derivative that was the object obtained (yellow solid, 2.52 g, in a yield of 82%). The synthesis scheme of Step 2 is shown in Formula (b-2).

[Chemical Formula 37]

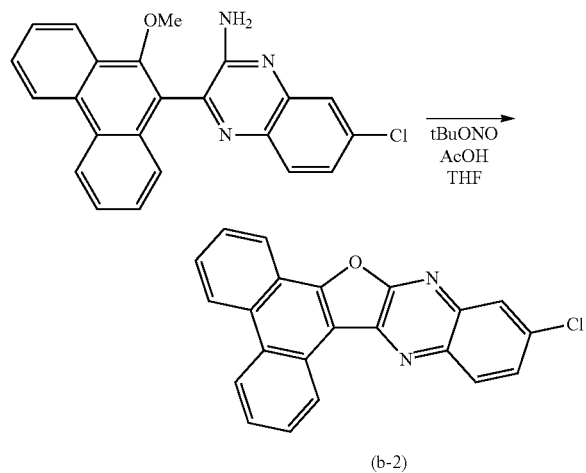

(b-2)

<Step 3; Synthesis of 12mDBtBPPnfqn>

Into a three-neck flask were put 1.19 g of 12-chlorophenanthro[9',10':4,5]furo[2,3-b]quinoxaline obtained in Step 2, 1.58 g of 3'-(4-dibenzothiophene)-1,1'-biphenyl-3-boronic acid, 2.19 g of tripotassium phosphate, 0.76 g of tert-butyl alcohol, and 27 mL of diethylene glycol dimethyl ether (abbreviation: diglyme), and the air in the flask was replaced with nitrogen. The mixture in the flask was degassed by being stirred under reduced pressure, 15 mg of palladium(II) acetate (abbreviation: Pd(OAc)$_2$) and 48 mg of di(1-adamantyl)-n-butylphosphine (abbreviation: CataCXium A) were added thereto, and then stirring was performed at 150° C. for 15 hours for reaction.

After a predetermined time elapsed, the obtained suspension was subjected to suction filtration, followed by washing with water and ethanol. The obtained solid was dissolved in toluene, and the mixture was filtered through a filter aid in which Celite, alumina, and Celite were stacked in this order and was recrystallized with toluene, whereby a substance that was the object was obtained (a yellow solid, 1.25 g, in a yield of 56%).

By a train sublimation method, 1.24 g of the obtained yellow solid was purified by sublimation. The conditions of the purification by sublimation were such that the solid was heated under a pressure of 2.6 Pa at 380° C. while the argon gas flowed at a flow rate of 10 mL/min. After the purification by sublimation, 0.85 g of a yellow solid that was the object was obtained in a yield of 69%. The synthesis scheme of Step 3 is shown in (b-3).

[Chemical Formula 38]

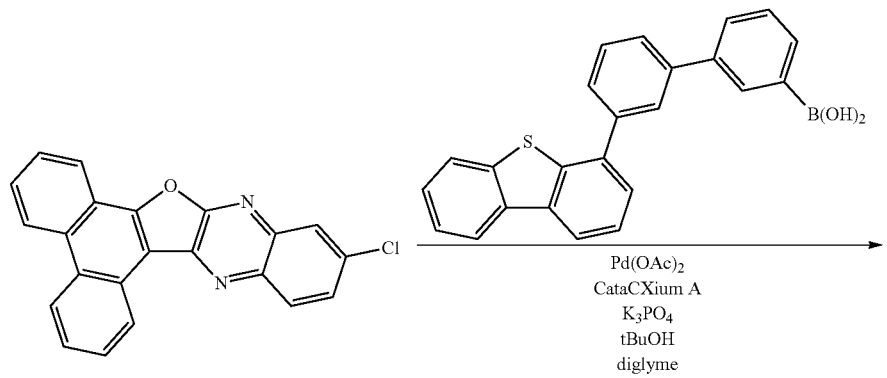

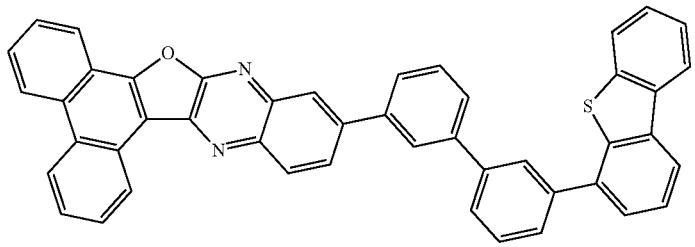

12mDBtBPPnfqn (b-3)

Figure 27:
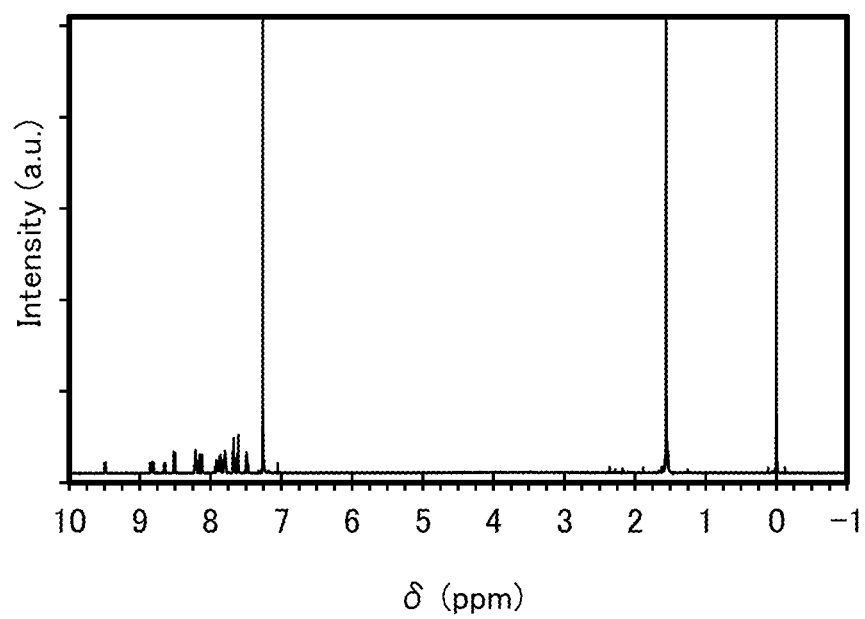
FIG. 27 is a chart of an organic compound represented by Structural Formula (113).

Analysis results by nuclear magnetic resonance spectroscopy ($^1$H-NMR) of the yellow solid obtained in Step 3 are shown below. FIG. 27 is the $^1$H-NMR chart. The results revealed that 12mDBtBPPnfqn, which is represented by Structural Formula (113), was obtained in this example.

$^1$H-NMR. δ (CDCl$_3$): 7.47-7.50 (m, 2H), 7.60-7.69 (m, 4H), 7.78-7.94 (m, 9H), 8.12 (s, 1H), 8.15 (s, 1H), 8.19-8.23 (m, 3H), 8.50-8.52 (m, 2H), 8.65 (d, 1H), 8.81 (d, 1H), 8.85 (d, 1H), 9.49 (s, 1H).

REFERENCE NUMERALS

101: first electrode, 102: second electrode, 103: EL layer, 103a: EL layer, 103b: EL layer, 103c: EL layer, 104: charge-generation layer, 111: hole-injection layer, 112: hole-transport layer, 113: light-emitting layer, 114: electron-transport layer, 115: electron-injection layer, 201: substrate, 202: insulating layer, 202a: insulating layer, 202b: insulating layer, 203B: light-emitting device, 203G: light-emitting device, 203R: light-emitting device, 203W: light-emitting device, 204: insulating layer, 205: substrate, 206B: color filter, 206G: color filter, 206R: color filter, 207: space, 208: adhesive layer, 209: black matrix, 210: transistor, 211: first electrode, 212G: conductive layer, 212R: conductive layer, 213: EL layer, 213B: EL layer, 213G: EL layer, 213R: EL layer, 215: second electrode, 220B: optical distance, 220G: optical distance, 220R: optical distance, 301: first substrate, 302: pixel portion, 303: circuit portion, 304a: circuit portion, 304b: circuit portion, 305: sealant, 306: second substrate, 307: wiring, 308: FPC, 309: transistor, 310: transistor, 311: transistor, 312: transistor, 313: first electrode, 314: insulating layer, 315: EL layer, 316: second electrode, 317: organic EL device, 318: space, 320: transistor, 321: conductive layer, 322a: conductive layer, 322b: conductive layer, 323: conductive layer, 324: insulating layer, 325: insulating layer, 326: insulating layer, 327: semiconductor layer, 327i: channel formation region, 327n: low-resistance region, 328: insulating layer, 330: transistor, 331: conductive layer, 332a: conductive layer, 332b: conductive layer, 333: conductive layer, 334: insulating layer, 335: insulating layer, 337: semiconductor layer, 338: insulating layer, 401: first electrode, 402: EL layer, 403: second electrode, 405: insulating layer, 406: conductive layer, 407: adhesive layer, 416: conductive layer, 420: substrate, 422: adhesive layer, 423: barrier layer, 424: insulating layer, 450: organic EL device, 490a: substrate, 490b: substrate, 490c: barrier layer, 800: substrate, 801: first electrode, 803: second electrode, 811: hole-injection layer, 812: hole-transport layer, 813: light-emitting layer, 814: electron-transport layer, 815: electron-injection layer, 911: housing, 912: light source, 913: sensing stage, 914: imaging device, 915: light-emitting portion, 916: light-emitting portion, 917: light-emitting portion, 921: housing, 922: operation button, 923: sensing portion, 924: light source, 925: imaging device, 931: housing, 932: operation panel, 933: transport mechanism, 934: monitor, 935: sensing unit, 936: test specimen, 937: imaging device, 938: light source, 981: housing, 982: display portion, 983: operation button, 984: external connection port, 985: speaker, 986: microphone, 987: first camera, 988: second camera, 7000: display portion, 7001: display portion, 7100: television, 7101: housing, 7103: stand 7111: remote controller, 7200: laptop, 7211: housing, 7212: keyboard, 7213: pointing device, 7214: external connection port, 7300: digital signage, 7301: housing, 7303: speaker, 7311: information terminal, 7400: digital signage, 7401: pillar, 7411: information terminal, 7600: portable information terminal, 7601: housing, 7602: hinge, 7650: portable information terminal, 7651: non-display portion, 7800: portable information terminal, 7801: band 7802: input-output terminal, 7803: operation button, 7804: icon, 7805: battery, 9700: automobile, 9701: car body, 9702: wheel, 9703: windshield, 9704: light, 9705: fog lamp, 9710: display portion, 9711: display portion, 9712: display portion, 9713: display portion, 9714: display portion, 9715: display portion, 9721: display portion, 9722: display portion, 9723: display portion This application is based on Japanese Patent Application Serial No. 2018-197429 filed on Oct. 19, 2018, the entire contents of which are hereby incorporated herein by reference.

The invention claimed is:

1. An organic compound represented by General Formula (G0):

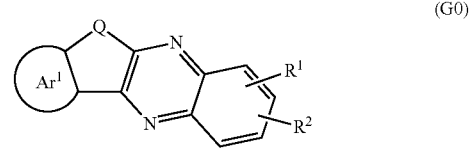

(G0)

$$A^1-(\alpha)_n-*$$

(u1)

wherein in General Formula (G0), Q represents oxygen or sulfur, $Ar^1$ represents a substituted or unsubstituted fused aromatic ring, $R^1$ and $R^2$ each independently represent hydrogen or a group with 1 to 100, inclusive, carbon atoms in total, at least one of $R^1$ and $R^2$ comprises a hole-transport skeleton, and at least one of $R^1$ and $R^2$ represents a structure represented by General Formula (u1), and wherein in General Formula (u1), α represents a substituted or unsubstituted arylene group with 6 to 25, inclusive, carbon atoms, n represents an integer greater than or equal to 0 and less than or equal to 4, $A^1$ represents any one of a substituted or unsubstituted aryl group with 6 to 30, inclusive, carbon atoms and a substituted or unsubstituted heteroaryl group with 3 to 30, inclusive, carbon atoms, and * represents a connection portion in General Formula (G0).

2. The organic compound according to claim 1, wherein the $Ar^1$ represents any one of a substituted or unsubstituted naphthalene ring, a substituted or unsubstituted phenanthrene ring, and a substituted or unsubstituted chrysene ring.

3. The organic compound according to claim 1, wherein the $A^1$ represents any one of General Formula ($A^1$-1) to General Formula ($A^1$-17):
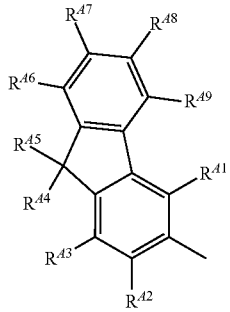
($A^1$-1)
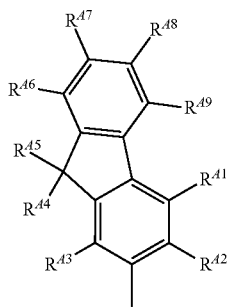
($A^1$-2)
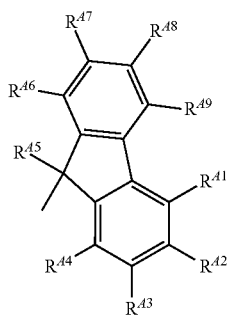
($A^1$-3)
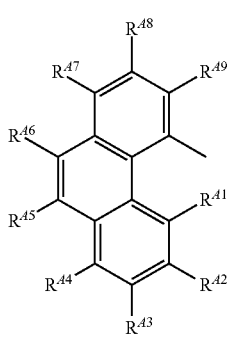
($A^1$-4)
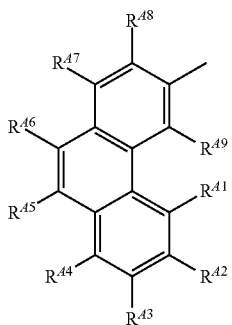
($A^1$-5)
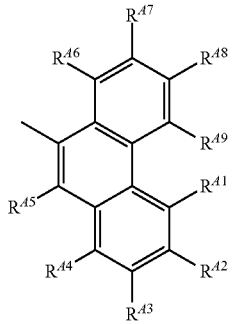
($A^1$-6)
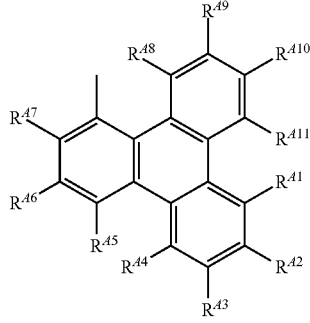
($A^1$-7)
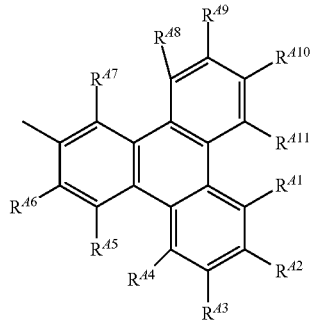
($A^1$-8)
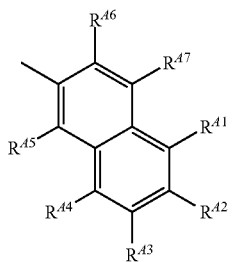
($A^1$-9)

-continued

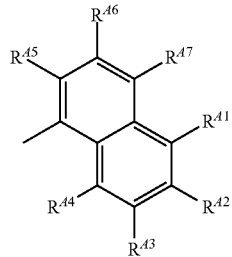
(A¹-10)

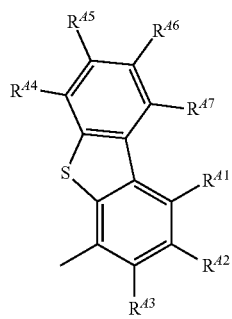
(A¹-11)

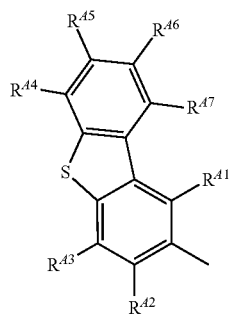
(A¹-12)

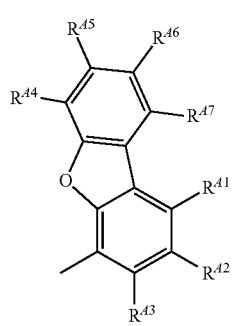
(A¹-13)

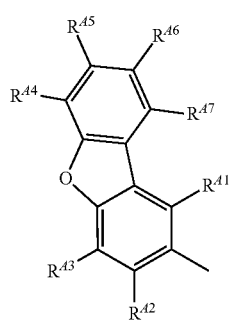
(A¹-14)

-continued

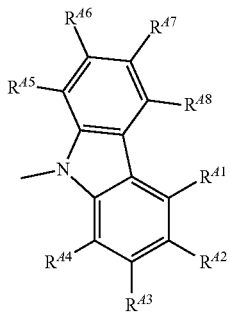
(A¹-15)

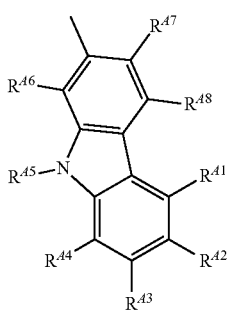
(A¹-16)

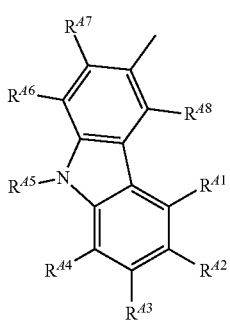
(A¹-17)

wherein $R^{A1}$ to $R^{A11}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, and a substituted or unsubstituted aryl group with 6 to 30, inclusive, carbon atoms.

4. The organic compound according to claim 1,
wherein the α represents any one of General Formula (Ar-1) to General Formula (Ar-14):

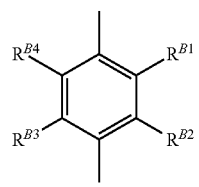
(Ar-1)

-continued
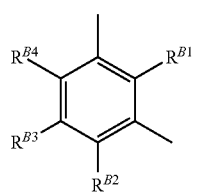
(Ar-2)
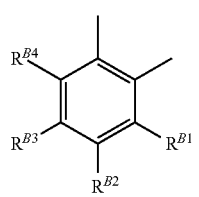
(Ar-3)
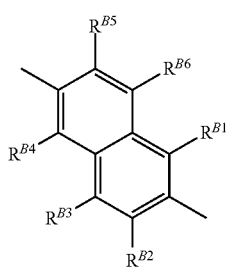
(Ar-4)
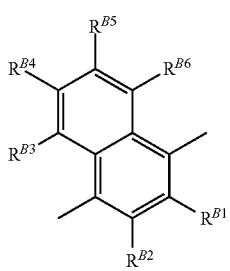
(Ar-5)
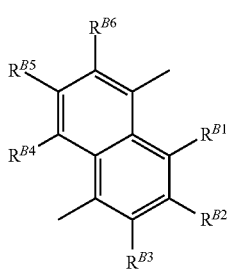
(Ar-6)
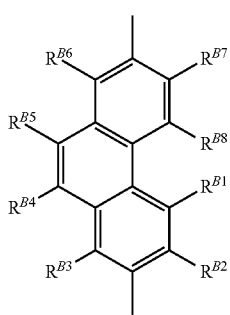
(Ar-7)
-continued
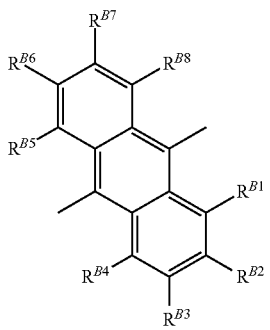
(Ar-8)
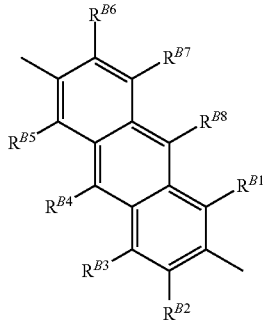
(Ar-9)
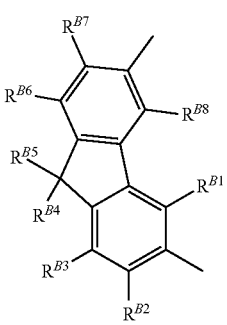
(Ar-10)
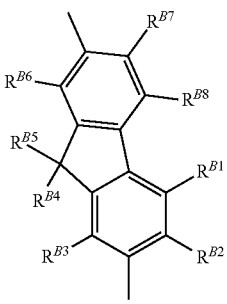
(Ar-11)
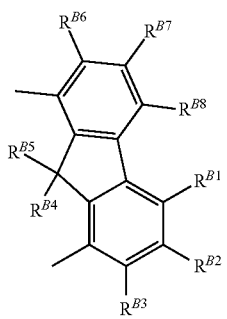
(Ar-12)

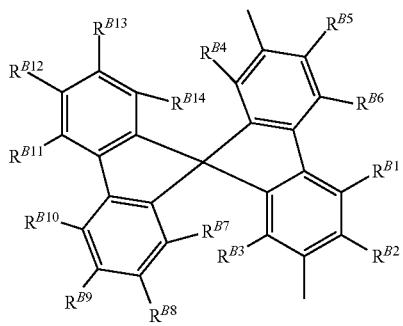

(Ar-13)

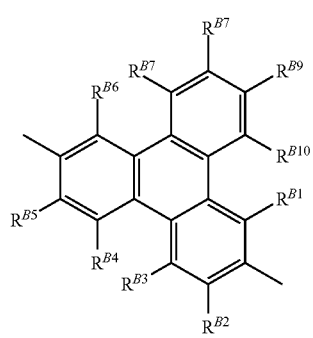

(Ar-14)

wherein $R^{B1}$ to $RB^{14}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, and a substituted or unsubstituted aryl group with 6 to 30, inclusive, carbon atoms.

5. The organic compound according to claim 1,
wherein the $Ar^1$ represents any one of General Formula (t1) to General Formula (t3):

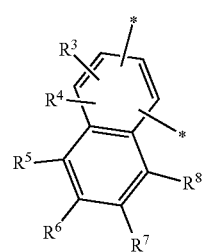

(t1)

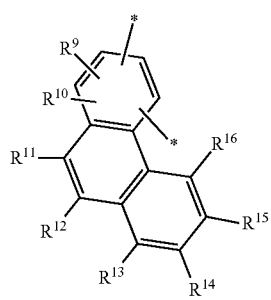

(t2)

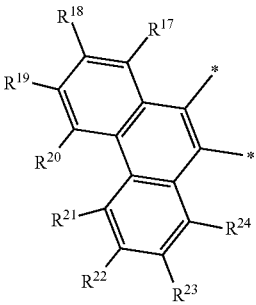

(t3)

wherein $R^3$ to $R^{24}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, a substituted or unsubstituted aryl group with 6 to 30, inclusive, carbon atoms, and * represents a connection portion in General Formula (G0).

6. The organic compound according to claim 1,
wherein the organic compound is represented by General Formula (G1):

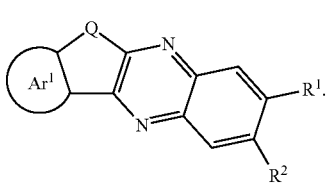

(G1)

7. The organic compound according to claim 1,
wherein the organic compound is represented by any one of General Formula (G1-1) to General Formula (G1-4):

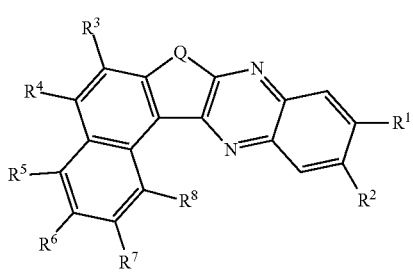

(G1-1)

-continued (G1-2)

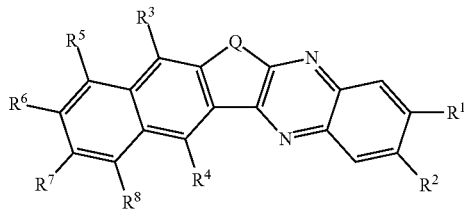

(G1-3)

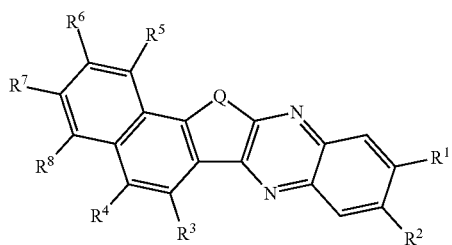

-continued (G1-4)

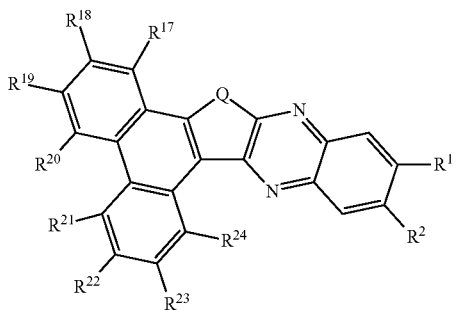

wherein $R^3$ to $R^8$ and $R^{17}$ to $R^{24}$ each independently represent any one of hydrogen, a substituted or unsubstituted alkyl group with 1 to 6, inclusive, carbon atoms, a substituted or unsubstituted cycloalkyl group with 3 to 7, inclusive, carbon atoms, and a substituted or unsubstituted aryl group with 6 to 30, inclusive, carbon atoms.

8. A light-emitting device comprising the organic compound according to claim 1.

9. A light-emitting apparatus comprising:
the light-emitting device according to claim 8; and
at least one of a transistor and a substrate.

* * * * *